US007196181B1

(12) United States Patent
Rapoport

(10) Patent No.: US 7,196,181 B1
(45) Date of Patent: *Mar. 27, 2007

(54) SEQUENCES ENCODING NOVEL HUMAN THYROID PEROXIDASE PROTEINS AND POLYPEPTIDES

(75) Inventor: Basil Rapoport, Santa Monica, CA (US)

(73) Assignee: Quest Diagnostics Investments, Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 745 days.

(21) Appl. No.: 08/482,402

(22) Filed: Jun. 7, 1995

Related U.S. Application Data

(60) Division of application No. 08/196,082, filed on Mar. 3, 1994, now abandoned, and a continuation-in-part of application No. 08/182,117, filed on Jan. 27, 1994, now abandoned, which is a continuation of application No. PCT/US92/07381, filed on Aug. 28, 1992, which is a continuation-in-part of application No. PCT/US92/06283, filed on Jul. 30, 1992, which is a continuation-in-part of application No. 07/750,579, filed on Aug. 28, 1991, now abandoned, which is a continuation-in-part of application No. 07/738,040, filed on Jul. 30, 1991, now abandoned, which is a continuation-in-part of application No. 07/555,955, filed on Jul. 31, 1990, now abandoned, which is a continuation-in-part of application No. 07/472,070, filed on Jan. 30, 1990, now abandoned, which is a continuation-in-part of application No. 07/388,040, filed on Jul. 31, 1989, now abandoned.

(51) Int. Cl.
C12N 15/11 (2006.01)

(52) U.S. Cl. ............... 536/23.1; 536/23.2; 536/23.5

(58) Field of Classification Search ............... 536/23.1, 536/23.2, 23.5; 435/320.1, 325
See application file for complete search history.

(56) References Cited

U.S. PATENT DOCUMENTS

| 4,098,876 A | 7/1978 | Piasio et al. |
| 4,376,110 A | 3/1983 | David et al. |

FOREIGN PATENT DOCUMENTS

| EP | 0139417 | * | 8/1984 |
| EP | 0421139 | | 5/1990 |
| EP | 0 655 502 A1 | | 5/1995 |
| WO | 9102061 | | 2/1991 |
| WO | 9303146 | | 2/1993 |
| WO | 9305072 | | 3/1993 |
| WO | 93/23073 | | 11/1993 |
| WO | 98/20354 | | 5/1998 |

OTHER PUBLICATIONS

Rose et al (cell, 30:753–762), 1982.*
Magnusson et al (OBC, 202:13885–13888), 1989.*
Seto et al(J. Clin.Invest, 80:1205–1208), 1987.*
Libert et al (NAR, 1987, 15:6735), 1987.*
Lee et al (Nature, 294:228–232), 1981.*
Ellis et al (Cell, 1986, 45:721–732), 1986.*
Rapoport (Annual Rev. Med., 42:91–96), 1991.*
Jones, et al., Abstract entitled "High–level expression of recombinant immunoreactive thyroid peroxidase in the High Five insect cell line", Journal of Molecular Endocrinology vol. 17, Issue 2. pp. 165–174 (1996).
"Deciphering the Message in Protein Sequences: Tolerance to Amino Acid Substitutions" by Bowie et al.; *Science*, vol. 247, Mar. 16, 1990, pp. 1306–1310.
"Studies on the Role of Amino Acids 38–45 in the Expression of a Functional Thyrotropin Receptor" by Wadsworth et al.; Molecular Endocrinology 1992, vol. 6 No. 3, pp. 394–398.
"Engineering the Human Thyrotropin Receptor Ectodomain From a Non–Secreted Form to a Secreted, Highly Immunoreactive Glycoprotein that Neutralizes Autoantibodies in Graves' Patients' Sera" by Chazenbalk et al.; *The Journal of Biological Chemistry*, vol. 272, No. 30, Issue of Jul. 25, pp. 18959–18965, 1997.
Finke et al, *Journal of Clinical Endocrinology and Metabolism*, vol. 71(1), pp. 53–59, 1990.
Potocnjak et al, *Science*, vol. 215, pp. 1637–1639, 1982.
Portolano et al, *Biochemical and Biophysical Research Communications*, vol. 179(1), pp. 372–377, 1991.
Banga et al, *Journal of Endocrinology*, vol. 124 (Supp.), Abstract No. 196, 1990.
Ewins et al, *Journal of Endocrinology*, vol. 124 (Supp.), Abstract No. 86, 1990.
Ludgate et al, *Journal of Clinical Endocrinology and Metabolism*, vol. 68(6), pp. 1091–1095, 1989.
Kimura et al, *FEBS Letters*, vol. 250(2), pp. 377–380, 1989.
Wahl et al, *The Journal of Nuclear Medicine*, vol. 24, pp. 316–325, 1983.
Ruf et al, *Clincal Chemistry*, vol. 34(11), pp. 2231–2234, 1988.
Kaufman et al, *Molecular and Cellular Endocrinology*, vol. 78, pp. 107–114, 1991.
Burgess et al, *The Journal of Cell Biology*, vol. 111, pp. 2129–2138, 1990.
Tao et al, *The Journal of Immunology*, vol. 143(8), pp. 2395–2601, 1989.
Gillies et al, *Hum. Antibod. Hybridomas*, vol. 1(1), pp. 47–54, 1990.

(Continued)

*Primary Examiner*—Susan Ungar
(74) *Attorney, Agent, or Firm*—Stout, Uxa, Buyan & Mullins, LLP; Donald E. Stout; Greg S. Hollrigel

(57) ABSTRACT

Disclosed are DNA sequences encoding novel human thyroid peroxidase proteins and polypeptides capable of being secreted from cells, vectors comprising the sequences, and cells transformed with the vectors.

4 Claims, 37 Drawing Sheets

OTHER PUBLICATIONS

Lazar et al, *Molecular and Cellular Biology*, vol. 8(3), pp. 1247–1252, 1988.
Kendler et al, *Chemical Endocrinology*, vol. 33, pp. 751–760, 1990.
Foti et al, *Biochemical and Biophysical Research Communications*, vol. 168(1), pp. 281–287, 1990.
Kaufman et al, *Journal of Clinical Endocrinology and Metabolism*, vol. 70(3), pp. 724–728, 1990.
Magnusson et al, *FEBS Letters*, vol. 208(2), pp. 391–396, 1986.
Magnusson et al, *The Journal of Biological Chemistry*, vol. 262(29), pp. 13885–13888, 1987.
Libert et al, *The EMBO Journal*, vol. 6(13), pp. 4193–4196, 1987.
Magnusson et al, *Molecular Endocrinology*, vol. 1(11), pp. 856–861, 1987.
Kimura et al, *Proc. Natl. Acad, Sci. USA*, vol. 84, pp. 5555–5559, 1987.
Adler et al, *Analytical Biochemistry*, vol. 148, pp. 320–327 (1985).
Bogner et al, *Journal of Clinical Endocrinology and Metabolism*, vol. 59(4), pp. 734–738, 1984.
Clark et al, *Enzyme–Immunoassay*, Chapter 8, pp. 167–170 and 191–194.
Czernocka et al, *FEBS Letters*, vol. 190(1), pp. 147–152, 1985.
Doble et al, *Immunology*, vol. 64, pp. 23–29, 1988.
Elisei et al, *Autoimmunity*, vol. 8, pp. 65–70, 1990.
Hirayu et al, *Journal of Clinical Endocrinology and Metabolism*, vol. 64(3), pp. 578–584, 1987.
Finke et al, *Progress in Thyroid Research*, pp. 437–439, 1991.
Finke et al, *Journal of Clinical Endocrinology and Metabolism*, vol. 73(4), pp. 919–921, 1991.
Jansson et al, *Clin exp. Immunol.*, vol. 63, pp. 80–86, 1986.
Kaufman et al, *The Journal of Clinical Investigation*, vol. 84, pp. 394–403, 1989.
Kohno et al, *Clin exp. Immunol.*, vol. 65, pp. 534–541, 1986.
Kohno et al, *Journal of Clinical Endocrinology and Metabolism*, vol. 67(5), pp. 899–907, 1988.
Libert et al, *Journal of Clinical Endocrinology and Metabolism*, vol. 73(4), pp. 857–860, 1991.
Mariotti et al, *Journal of Clinical Endocrinology and Metabolism*, vol. 65(5), pp. 987–993, 1987.
Nilsson et al, *Molecular and Cellular Endocrinology*, vol. 53, pp. 177–186, 1987.
Ohtaki et al, *Journal of Clinical Endocrinology and Metabolism*, vol. 63(3), pp. 570–576, 1986.
Portmann et al, *Journal of Clinical Endocrinology and Metabolism*, vol. 61(5), pp. 1001–1003, 1985.
Portmann et al, *Journal of Clinical Investigation*, vol. 81, pp. 1217–1224, 1988.
Ruf et al, *Endocrinology*, vol. 125(3), pp. 1211–1218, 1989.
Sanger et al, *Proc. Natl. Acad. Sci. USA*, vol. 74(12), pp. 5463–5467, 1977.
Van Regenmortel et al, *Immunology Letters*, vol. 17, pp. 95–108, 1988.
Yokohama et al, *Journal of Clinical Endocrinology and Metabolism*, vol. 68(4), pp. 766–773, 1989.
Zanelli et al, *Clin exp. Immunol.*, vol. 87, pp. 80–86, 1992.
Magnusson et al, European Thyroid Meeting, Jul. 1986.
Magnusson et al, American Thyroid Association Meeting, Sep. 1987,.
Kimura et al, American Thyroid Assoication Meeting, Sep. 1987.
Magnusson et al, European Thyroid Meeting, Sep. 1988.
Dinsart et al, European Thyroid Meeting, Sep. 1988.
Hata et al, *Biochemical and Biophysical Research Communications*, vol. 164(3), pp. 1268–1273, 1989.
Nagayama et al, *Journal of Clinical Endocrinology and Metabolism*, vol. 71(2), pp. 384–390, 1990.
Hosoya et al, *J. Biochem.*, vol. 98(3), pp. 637–648, 1985.
"Isolation of a Complementary DNA Clone for Thyroid Microsomal Antigen Homology With the Gene for Thyroid Peroxidase" by Seto et al.; *The Journal of Clinical Investigation, Inc.*, vol. 80, Oct. 87, pp. 1205–1208.
"The Molecular Biology of Thyroid Peroxidase: Cloning, Expression and Role as Autoantigen in Autoimmune Thyroid Disease" by McLachlan et al.; *Endocrine Reviews*, vol. 13, No. 2, 1992, pp. 192–206.
"Generation of Recombinant, Enzymatically Active Human Thyroid Peroxidase and its Recognition by Antibodies in the Sera of Patients With Hashimoto's Thyroiditis" by Kaufman et al.; *The Journal of Clinical Investigation, Inc.*, vol. 84, Aug. 89, pp. 394–403.

* cited by examiner

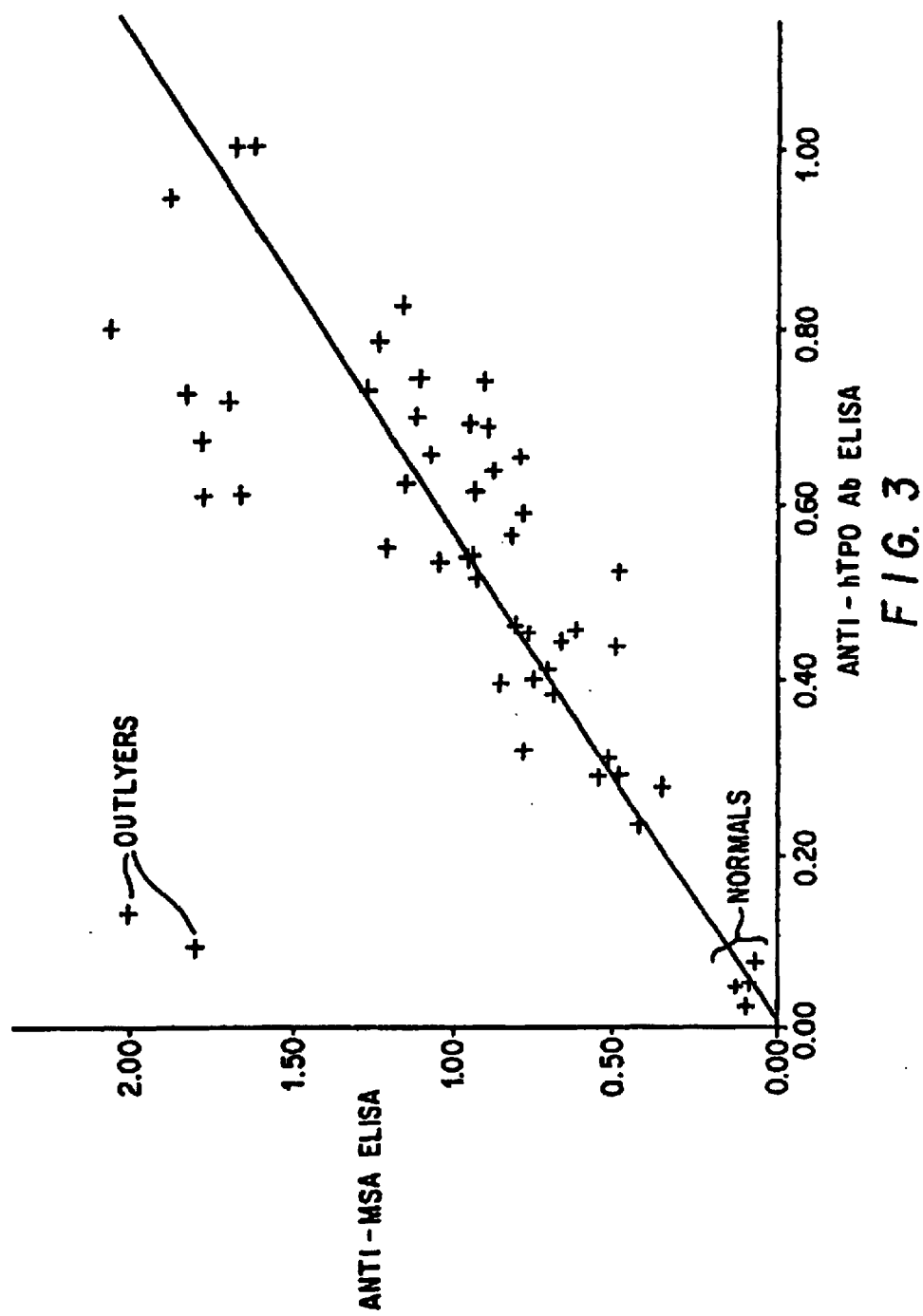

2611                                                        2662

AGG CTC CCT CGG GTG ACT TGG ATC TCC ATG TGG CTG GCT GCT CTG CTG ATC G    pHTPO-BS

<u>Eco RI</u>

Stop        Stop

AGG CTC CCT CGG GTG ACT TGA ATT CCC ATG TAG CTG GCT GCT CTG CTG ATC G    pHTPO(M1)-BS

*FIG. 6*

```
                                    27                                              54
GAG GCA ATT GAG GCG CCC ATT TCA GAA GAG TTA CAG CCG TGA AAA TTA CTC AGC 81                                              108
AGT GCA GTT GGC TGA GAA GAG GAA AAA AGA ATG AGA GCG CTG GCT GTG CTG TCT
                                            MET Arg Ala Leu Ala Val Leu Ser 135                                             162
GTC ACG CTG GTT ATG GCC TGC ACA GAA GCC TTC TTC CCC TTC ATC TCG AGA GGG
Val Thr Leu Val Met Ala Cys Thr Glu Ala Phe Phe Pro Phe Ile Ser Arg Gly 189                                             216
AAA GAA CTC CTT TGG GGA AAG CCT GAG GAG TCT CGT GTC TCT AGC GTC TTG GAG
Lys Glu Leu Leu Trp Gly Lys Pro Glu Glu Ser Arg Val Ser Ser Val Leu Glu 243                                             270
GAA AGC AAG CGC CTG GTG GAC ACC GCC ATG TAC GCC ACG ATG CAG AGA AAC CTC
Glu Ser Lys Arg Leu Val Asp Thr Ala Met Tyr Ala Thr Met Gln Arg Asn Leu 297                                             324
AAG AAA AGA GGA ATC CTT TCT GGA GCT CAG CTT CTG TCT TTT TCC AAA CTT CCT
Lys Lys Arg Gly Ile Leu Ser Gly Ala Gln Leu Leu Ser Phe Ser Lys Leu Pro 351                                             378
GAG CCA ACA AGC GGA GTG ATT GCC CGA GCA GCA GAG ATA ATG GAA ACA TCA ATA
Glu Pro Thr Ser Gly Val Ile Ala Arg Ala Ala Glu Ile Met Glu Thr Ser Ile 405                                             432
CAA GCG ATG AAA AGA AAA GTC AAC CTG AAA ACT CAA CAA TCA CAG CAT CCA ACG
Gln Ala Met Lys Arg Lys Val Asn Leu Lys Thr Gln Gln Ser Gln His Pro Thr 459                                             486
GAT GCT TTA TCA GAA GAT CTG CTG AGC ATC ATT GCA AAC ATG TCT GGA TGT CTC
Asp Ala Leu Ser Glu Asp Leu Leu Ser Ile Ile Ala Asn Met Ser Gly Cys Leu
```

*FIG. 7A*

```
                                513                                         540
        CCT TAC ATG CTG CCC CCA AAA TGC CCA AAC ACT TGC CTG GCG AAC AAA TAC AGG
        Pro Tyr Met Leu Pro Pro Lys Cys Pro Asn Thr Cys Leu Ala Asn Lys Tyr Arg 567                                         594
        CCC ATC ACA GGA GCT TGC AAC AAC AGA GAC CAC CCC AGA TGG GGC GCC TCC AAC
        Pro Ile Thr Gly Ala Cys Asn Asn Arg Asp His Pro Arg Trp Gly Ala Ser Asn 621                                         648
        ACG GCC CTG GCA CGA TGG CTC CCT CCA GTC TAT GAG GAC GGC TTC AGT CAG CCC
        Thr Ala Leu Ala Arg Trp Leu Pro Pro Val Tyr Glu Asp Gly Phe Ser Gln Pro 675                                         702
        CGA GGC TGG AAC CCC GGC TTC TTG TAC AAC GGG TTC CCA CTG CCC CCG GTC CGG
        Arg Gly Trp Asn Pro Gly Phe Leu Tyr Asn Gly Phe Pro Leu Pro Pro Val Arg 729                                         756
        GAG GTG ACA AGA CAT GTC ATT CAA GTT TCA AAT GAG GTT GTC ACA GAT GAT GAC
        Glu Val Thr Arg His Val Ile Gln Val Ser Asn Glu Val Val Thr Asp Asp Asp 783                                         810
        CGC TAT TCT GAC CTC CTG ATG GCA TGG GGA CAA TAC ATC GAC CAC GAC ATC GCG
        Arg Tyr Ser Asp Leu Leu MET Ala Trp Gly Gln Tyr Ile Asp His Asp Ile Ala 837                                         864
        TTC ACA CCA CAG AGC ACC AGC AAA GCT GCC TTC GGG GGA GGG TCT GAC TGC CAG
        Phe Thr Pro Gln Ser Thr Ser Lys Ala Ala Phe Gly Gly Gly Ser Asp Cys Gln 891                                         918
        ATG ACT TGT GAG AAC CAA AAC CCA TGT TTT CCC ATA CAA CTC CCG GAG GAG GCC
        Met Thr Cys Glu Asn Gln Asn Pro Cys Phe Pro Ile Gln Leu Pro Glu Glu Ala 945                                         972
        CGG CCG GCC GCG GGC ACC GCC TGT CTG CCC TTC TAC CGC TCT TCG GCC GCC TGC
        Arg Pro Ala Ala Gly Thr Ala Cys Leu Pro Phe Tyr Arg Ser Ser Ala Ala Cys
```

FIG. 7B

```
                              999                                          1026
GGC ACC GGG GAC CAA GGC GCG CTC TTT GGG AAC CTG TCC ACG GCC AAC CCG AGG
Gly Thr Gly Asp Gln Gly Ala Leu Phe Gly Asn Leu Ser Thr Ala Asn Pro Arg
                                            x 1053                                         1080
CAG CAG ATG AAC GGG TTG ACC TCG TTC CTG GAC GCG TCC ACC GTG TAT GGC AGC
Gln Gln Met Asn Gly Leu Thr Ser Phe Leu Asp Ala Ser Thr Val Tyr Gly Ser 1107                                         1134
TCC CCG GCC CTA GAG AGG CAG CTG CGG AAC TGG ACC AGT GCC GAA GGG CTG CTC
Ser Pro Ala Leu Glu Arg Gln Leu Arg Asn Trp Thr Ser Ala Glu Gly Leu Leu
                                      x 1161                                         1188
CGC GTC CAC GGC CGC CTC CGG GAC TCC GGC CGC GCC TAC CTG CCC TTC GTG CCG
Arg Val His Gly Arg Leu Arg Asp Ser Gly Arg Ala Tyr Leu Pro Phe Val Pro 1215                                         1242
CCA CGC GCG CCT GCG GCC TGT GCG CCC GAG CCC GGC AAC CCC GGA GAG ACC CGC
Pro Arg Ala Pro Ala Ala Cys Ala Pro Glu Pro Gly Asn Pro Gly Glu Thr Arg 1269                                         1296
GGG CCC TGC TTC CTG GCC GGA GAC GGC CGC GCC AGC GAG GTC CCC TCC CTG ACG
Gly Pro Cys Phe Leu Ala Gly Asp Gly Arg Ala Ser Glu Val Pro Ser Leu Thr 1323                                         1350
GCA CTG CAC ACG CTG TGG CTG CGC GAG CAC AAC CGC CTG GCC GCG GCG CTC AAG
Ala Leu His Thr Leu Trp Leu Arg Glu His Asn Arg Leu Ala Ala Ala Leu Lys 1377                                         1404
GCC CTC AAT GCG CAC TGG AGC GCG GAC GCC GTG TAC CAG GAG GCG CGC AAG GTC
Ala Leu Asn Ala His Trp Ser Ala Asp Ala Val Tyr Gln Glu Ala Arg Lys Val 1431                                         1458
GTG GGC GCT CTG CAC CAG ATC ATC ACC CTG AGG GAT TAC ATC CCC AGG ATC CTG
Val Gly Ala Leu His Gln Ile Ile Thr Leu Arg Asp Tyr Ile Pro Arg Ile Leu
```

FIG. 7C

```
                              1485                                          1512
GGA CCC GAG GCC TTC CAG CAG TAC GTG GGT CCC TAT GAA GGC TAT GAC TCC ACC
Gly Pro Glu Ala Phe Gln Gln Tyr Val Gly Pro Tyr Glu Gly Tyr Asp Ser Thr 1539                                               1566
GCC AAC CCC ACT GTG TCC AAC GTG TTC TCC ACA GCC GCC TTC CGC TTC GGC CAT
Ala Asn Pro Thr Val Ser Asn Val Phe Ser Thr Ala Ala Phe Arg Phe Gly His
     *

1593                                          1620
GCC ACG ATC CAC CCG CTG GTG AGG AGG CTG GAC GCC AGC TTC CAG GAG CAC CCC
Ala Thr Ile His Pro Leu Val Arg Arg Leu Asp Ala Ser Phe Gln Glu His Pro 1647                                                    1674
GAC CTG CCC GGG CTG TGG CTG CAC CAG GCT TTC TTC AGC CCA TGG ACA TTA CTC
Asp Leu Pro Gly Leu Trp Leu His Gln Ala Phe Phe Ser Pro Trp Thr Leu Leu 1701                                               1728
CGT GGA GGT GGT TTG GAC CCA CTA ATA CGA GGC CTT CTT GCA AGA CCA GCC AAA
Arg Gly Gly Gly Leu Asp Pro Leu Ile Arg Gly Leu Leu Ala Arg Pro Ala Lys 1755                                          1782
CTG CAG GTG CAG GAT CAG CTG ATG AAC GAG GAG CTG ACG GAA AGG CTC TTT GTG
Leu Gln Val Gln Asp Gln Leu Met Asn Glu Glu Leu Thr Glu Arg Leu Phe Val 1809                                               1836
CTG TCC AAT TCC AGC ACC TTG GAT CTG GCG TCC ATC AAC CTG CAG AGG GGC CGG
Leu Ser Asn Ser Ser Thr Leu Asp Leu Ala Ser Ile Asn Leu Gln Arg Gly Arg
        *

1863                                               1890
GAC CAC GGG CTG CCA GGT TAC AAT GAG TGG AGG GAG TTC TGC GGC CTG CCT CGC
Asp His Gly Leu Pro Gly Tyr Asn Glu Trp Arg Glu Phe Cys Gly Leu Pro Arg 1917                                               1944
CTG GAG ACC CCC GCT GAC CTG AGC ACA GCC ATC GCC AGC AGG AGC GTG GCC GAC
Leu Glu Thr Pro Ala Asp Leu Ser Thr Ala Ile Ala Ser Arg Ser Val Ala Asp
```

*FIG. 7D*

```
                    1971                                              1998
AAG ATC CTG GAC TTG TAC AAG CAT CCT GAC AAC ATC GAT GTC TGG CTG GGA GGC
Lys Ile Leu Asp Leu Tyr Lys His Pro Asp Asn Ile Asp Val Trp Leu Gly Gly 2025                                              2052
TTA GCT GAA AAC TTC CTC CCC AGG GCT CGG ACA GGG CCC CTG TTT GCC TGT CTC
Leu Ala Glu Asn Phe Leu Pro Arg Ala Arg Thr Gly Pro Leu Phe Ala Cys Leu 2079                                              2106
ATT GGG AAG CAG ATG AAG GCT CTG CGG GAC GGT GAC TGG TTT TGG TGG GAG AAC
Ile Gly Lys Gln Met Lys Ala Leu Arg Asp Gly Asp Trp Phe Trp Trp Glu Asn 2133                                              2160
AGC CAC GTC TTC ACG GAT GCA CAG AGG CGT GAG CTG GAG AAG CAC TCC CTG TCT
Ser His Val Phe Thr Asp Ala Gln Arg Arg Glu Leu Glu Lys His Ser Leu Ser 2187                                              2214
CGG GTC ATC TGT GAC AAC ACT GGC CTC ACC AGG GTG CCC ATG GAT GCC TTC CAA
Arg Val Ile Cys Asp Asn Thr Gly Leu Thr Arg Val Pro Met Asp Ala Phe Gln 2241                                              2268
GTC GGC AAA TTC CCC GAA GAC TTT GAG TCT TGT GAC AGC ATC ACT GGC ATG AAC
Val Gly Lys Phe Pro Glu Asp Phe Glu Ser Cys Asp Ser Ile Thr Gly Met Asn 2295                                              2322
CTG GAG GCC TGG AGG GAA ACC TTT CCT CAA GAC GAC AAG TGT GGC TTC CCA GAG
Leu Glu Ala Trp Arg Glu Thr Phe Pro Gln Asp Asp Lys Cys Gly Phe Pro Glu 2349                                              2376
AGC GTG GAG AAT GGG GAC TTT GTG CAC TGT GAG GAG TCT GGG AGG CGC GTG CTG
Ser Val Glu Asn Gly Asp Phe Val His Cys Glu Glu Ser Gly Arg Arg Val Leu 2403                                              2430
GTG TAT TCC TGC CGG CAC GGG TAT GAG CTC CAA GGC CGG GAG CAG CTC ACT TGC
Val Tyr Ser Cys Arg His Gly Tyr Glu Leu Gln Gly Arg Glu Gln Leu Thr Cys 2457                                              2484
ACC CAG GAA GGA TGG GAT TTC CAG CCT CCC CTC TGC AAA GAT GTG AAC GAG TGT
Thr Gln Glu Gly Trp Asp Phe Gln Pro Pro Leu Cys Lys Asp Val Asn Glu Cys
```

FIG. 7E

```
                              2511                                              2538
GCA GAC GGT GCC CAC CCC CCC TGC CAC GCC TCT GCG AGG TGC AGA AAC ACC AAA
Ala Asp Gly Ala His Pro Pro Cys His Ala Ser Ala Arg Cys Arg Asn Thr Lys 2565                                              2592
GGC GGC TTC CAG TGT CTC TGC GCG GAC CCC TAC GAG TTA GGA GAC GAT GGG AGA
Gly Gly Phe Gln Cys Leu Cys Ala Asp Pro Tyr Glu Leu Gly Asp Asp Gly Arg 2619                                              2646
ACC TGC GTA GAC TCC GGG AGG CTC CCT CGG GTG ACT TGG ATC TCC ATG TCG CTG
Thr Cys Val Asp Ser Gly Arg Leu Pro Arg Val Thr Trp Ile Ser Met Ser Leu 2673                                              2700
GCT GCT CTG CTG ATC GGA GGC TTC GCA GGT CTC ACC TCG ACG GTG ATT TGC AGG
Ala Ala Leu Leu Ile Gly Gly Phe Ala Gly Leu Thr Ser Thr Val Ile Cys Arg 2727                                              2754
TGG ACA CGC ACT GGC ACT AAA TCC ACA CTG CCC ATC TCG GAG ACA GGC GGA GGA
Trp Thr Arg Thr Gly Thr Lys Ser Thr Leu Pro Ile Ser Glu Thr Gly Gly Gly 2781                                              2808
ACT CCC GAG CTG AGA TGC GGA AAG CAC CAG GCC GTA GGG ACC TCA CCG CAG CGG
Thr Pro Glu Leu Arg Cys Gly Lys His Gln Ala Val Gly Thr Ser Pro Gln Arg 2835                                              2862
GCC GCA GCT CAG GAC TCG GAG CAG GAG AGT GCT GGG ATG GAA GGC CGG GAT ACT
Ala Ala Ala Gln Asp Ser Glu Gln Glu Ser Ala Gly Met Glu Gly Arg Asp Thr 2889                                              2916
CAC AGG CTG CCG AGA GCC CTC TGA GGG CAA AGT GGC AGG ACA CTG CAG AAC AGC
His Arg Leu Pro Arg Ala Leu ***

2943                                              2970
TTC ATG TTC CCA AAA TCA CCG TAC GAC TCT TTT CCA AAC ACA GGC AAA TCG GAA 2997                                              3024
ATC AGC AGG ACG ACT GTT TTC CCA ACA CGG GTA AAT CTA GTA CCA TGT CGT AGT

3051
TAC TCT CAG GCA TGG ATG AAT AAA TGT TAT AGC TGC AAA AAA AAA AAA
                                              AAA AAA
```

FIG. 7F

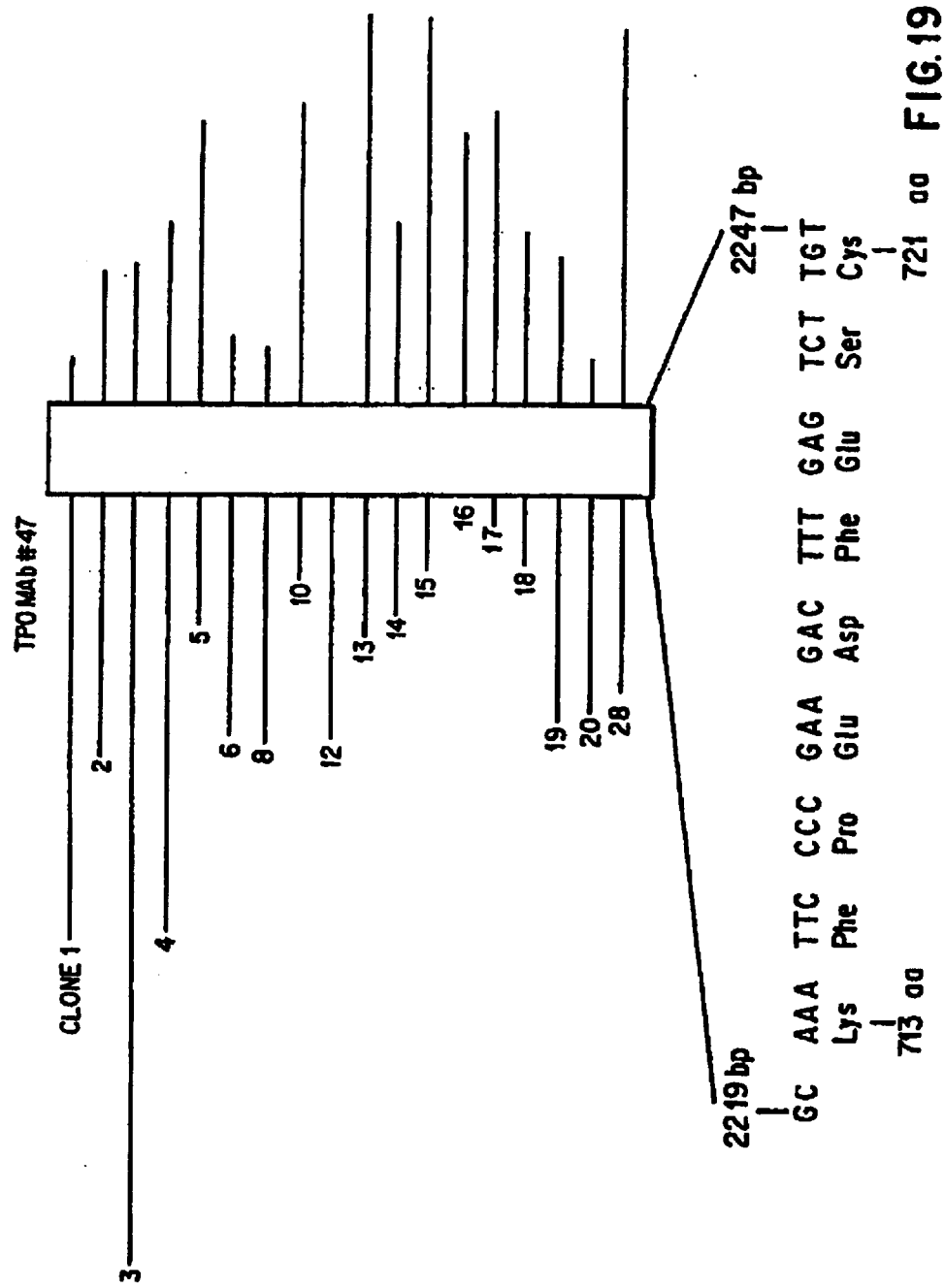

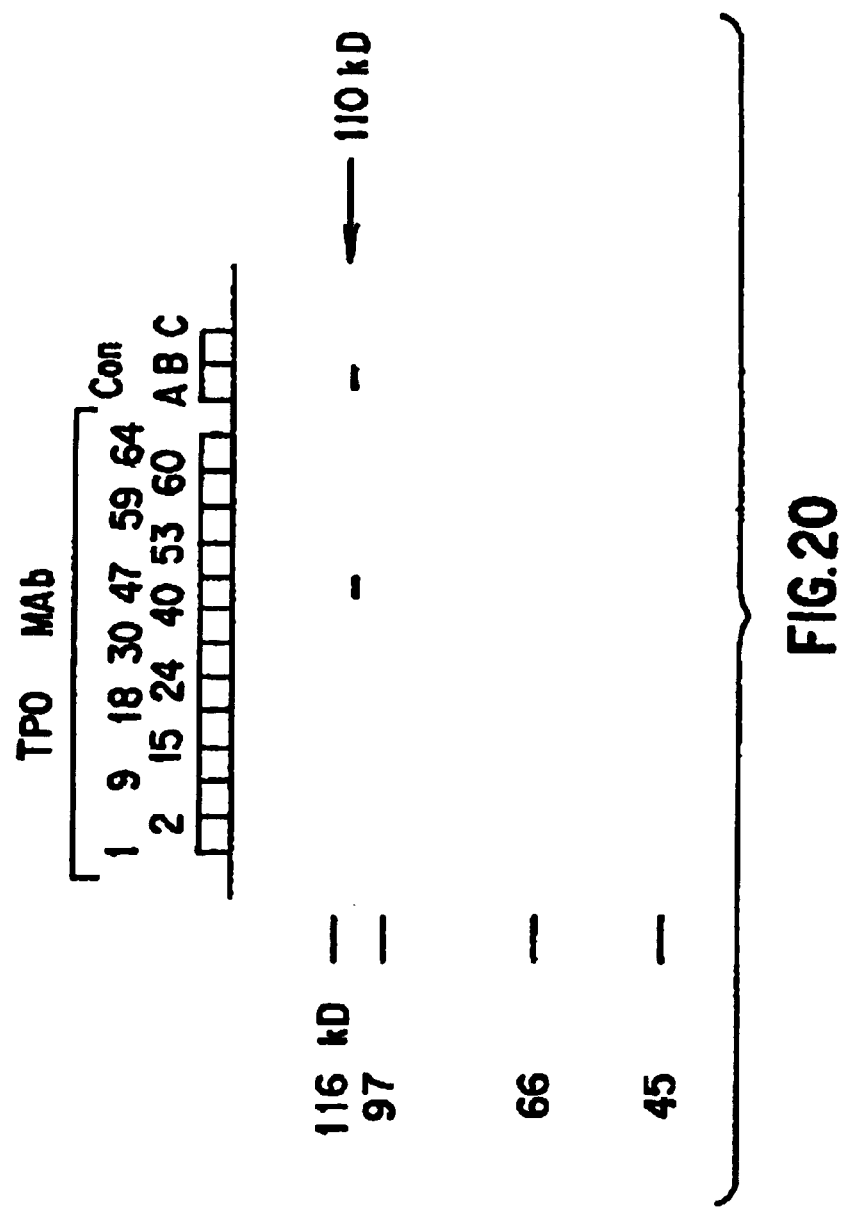

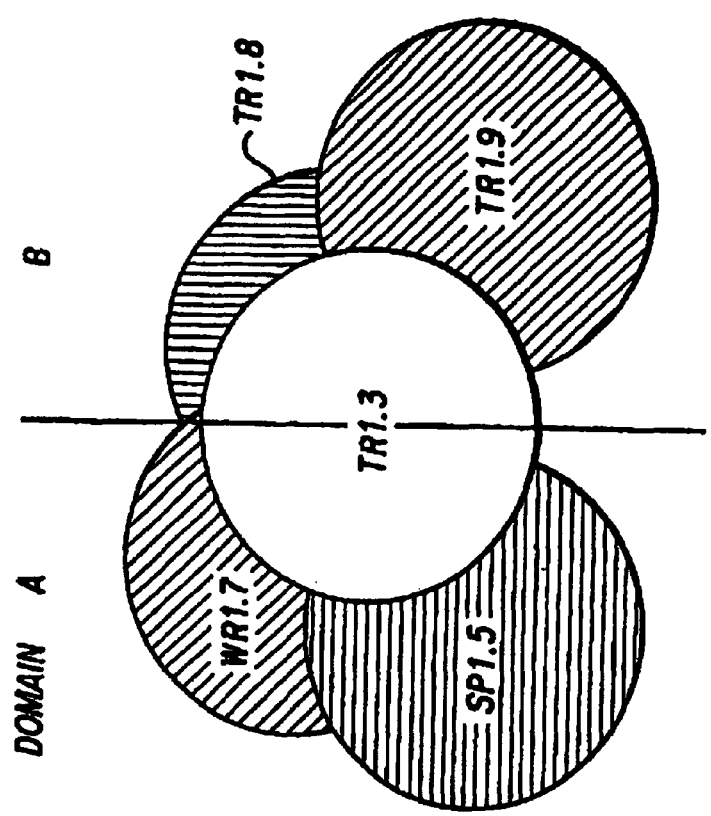

SEQUENCES ENCODING NOVEL HUMAN THYROID PEROXIDASE PROTEINS AND POLYPEPTIDES

CROSS-REFERENCE TO RELATED APPLICATIONS

This application is a division of U.S. application Ser. No. 08/196,082, filed Mar. 3, 1994, now abandoned, which is a continuation of International Application No. PCT/US92/07381, filed Aug. 28, 1992; and a continuation-in-part of U.S. patent application Ser. No. 08/182,117, filed Jan. 27, 1994, now abandoned, which is a conuation-in-part of International Application No. PCT/US/92/06283, filed Jul. 30, 1992, U.S. patent application Ser. No. 07/750,579, filed Aug. 28, 1991, now abandoned, and U.S. patent application Ser. No. 07/738,040, filed Jul. 30, 1991; now abandoned which is a continuation-in-part of U.S. patent application Ser. No. 07/559,955, filed Jul. 31, 1990, now abandoned, which is a continuation-in-part of U.S. patent application Ser. No. 07/472,070, filed Jan. 30, 1990, now abandoned, which is a continuation-in-part of U.S. patent application Ser. No. 07/388,044, filed Jul. 31, 1989, now abanoded.

BACKGROUND OF THE INVENTION

Part of the work leading to this invention was made with U.S. Government funds. The U.S. government has certain rights in this invention.

1. Field of the Invention

The present invention relates to the fields of molecular biology and immunology. More particularly, the invention relates to the production of recombinant human thyroid peroxidase in non-thyroidal eukaryotic cells. The invention is further related to methods of using recombinant human thyroid peroxidase, and, in particular, to methods of using recombinant human thyroid peroxidase in diagnosis and treatment of immune disorders such as Hashimoto's thyroiditis.

2. Brief Description of the Related Art

Hashimoto's thyroiditis is the most common autoimmune endocrinopathy, affecting, at least subclinically, up to 15% of the adult female population (Volpe, R., In *Wener's The Thyroid*, 5th Edition (Ingbar, S.H., et al., Eds.), J.B. Lippincott Co., Philadelphia, pp. 1266–1291 (1986); Gordin, A., et al., *Acta Endocrinol.* 90:33–42 (1979)). Antibodies against a number of thyroid antigens are present in the sera of these patients, including thyroglobulin and the thyroid "microsomal" antigen (Doniach, D., et al., *Clin. Endocrinol Metab.* 8:63–80 (1979); Weetman, A.P., et al., *Endocr. Rev.* 5:309–355 (1984)). Other antigens of lesser, or uncertain, importance, include the second colloid antigen (Doniach, D., et al., *Clin. Endocrinol. Metab.* 8:63–80 (1979)), tubulin (Rousset, B., et al., *Clin. Exp. Immunol.* 52:325–332 (1983)), DNA (Katakura, M., et al., *J. Clin. Endocrinol. Metab.* 64:405–408 (1987)) and Autoimmune Thyroid Disease-Related Antigen I (ATRA I) (Hirayu, H., et al., *J. Clin. Endocrinol. Metab.* 64:578–584 (1987)).

Antibodies against the microsomal antigen, which is expressed on the cell surface (Khoury, E.L., et al., *Exp. Immunol.* 45:315–328 (1981); Nilsson, M., et al., *Molec. Cell. Endocrinol.* 55:171–185 (1987)), are believed to be of greater importance than those against thyroglobulin in the pathogenesis of Hashimoto's thyroiditis. This is because antimicrosomal antibodies (MSA) are more closely associated with the active phase of the disease (Volpe, R., In *Werner's The Thyroid*, 5th Edition (Ingbar, S.H., et al., Eds.), J.B. Lippincott Co., Philadelphia, pp. 1266–1291 (1986); Bogner, U., *J. Clin. Endocrinol. Metab.* 59:734–738 (1984); Jansson, R., et al., *Clin. Exp. Immunol.* 63:80–86 (1986)) and are complement-fixing (Khoury, E.L., et al., *Exp. Immunol.* 45:315–328 (1981)). These antibodies are, therefore, likely to initiate thyroid cellular damage.

A major recent discovery regarding Hashimoto's thyroiditis is that the previously ill-defined microsomal antigen is, at least in part, thyroid peroxidase (TPO), the primary enzyme involved in thyroid hormone synthesis. This conclusion was based on imiunologic evidence (Czarnocka, B., *FEBS Letters* 109:147–152 (1985); Portmann, L., et al., *J. Clin. Endocrinol. Metab* 61:1001–1003 (1985); ; Mariotti, S., et al., *J. Clin. Endocrinol. Metab.* 65:987–993 (1987)) and subsequently confirmed by the molecular cloning of the cONA for these proteins (Magnusson, R.P., et al., *J. Biol. Chem.* 262:13885–13888 (1987); Magnusson, R.P., et al., *Mol. Endocrinol.* 1:856–861 (1987); Libert, R., et al., *EMBO J.* 6:4193–4176 (1987); Kimura, S., et al., *Proc. Natl. Acad. Sci. USA* 84:5555–5559 (1987)) and the discovery that their derived amino acid sequences are the same (Libert, R., et al., *EMBO J.* 6:4193–4176 (1987); Seto, P., et al., *J. Clin. Invest.* 80:1205–1208 (1987)).

Prior to the present invention, a suitable preparation of recombinant TPO has not been available for studies on the presumed abnormalities in immune regulation in Hashimoto's thyroiditis, or for the demonstration of the specific B-cell and T-cell epitopes involved in this disease. In this respect, understanding of the molecular mechanisms involved in the pathogenesis of Hashimoto's thyroiditis lags far behind that of other immune disorders, such as myasthenia gravis, a disease for which pure antigen (the acetylcholine receptor) has been obtained and epitopes already defined (Tzartos, S.J., et al., *Proc. Natl. Acad. Sci. USA* 85:2899–2903 (1988); Hohifeld, R., et al., *J. Clin. Invest.* 81:657–660 (1988)).

Human TPO (hTPO) imunopurified by monoclonal antibodies (mAbs) has been available, but is of limited value because of:

(a) inadequate supplies of human thyroid tissue; (b) the difficulties in purification of this membrane-bound antigen; and (c) contamination with other thyroid autoantigens such as thyroglobulin, which is highly abundant.

Fragments of hTPO have been generated as recombinant bacterial (β-galactosidase) fusion proteins, and reactivity of a number of Hashimoto patient sera with small fragments of TPO expressed as fusion proteins has been reported (Libert, R., et al., *EMBO J.* 6:4193–4176 (1987)). Those data, however, are difficult to interpret, because the plaque assays used require extensive pre-adsorption of polyclonal antisera (Hirayu, N., et al., *J. Clin. Endocrinol. Metab.* 64:578–584 (1987)) and can yield false positive results.

For example, a reported fusion protein originally described as reactive with 19 of 20 Hashimoto patient sera (Libert, R., et al., *EMBO J.* 6:4193–4176 (1981), clone C2) has, upon immunopurification with anti-β-galactosidase mAbs, been found to react with fewer Hashimoto patient sera in an ELISA assay (Dinsart, C., et al., *17th Annual Meeting of the European Thyroid Association*, Abstract #235 (1988)).

Thus, bacterial fusion proteins, too, have been of limited value because: (a) no combination of fragments has been found that reacts with all Hashimoto's sera; (b) the conformation of the fusion protein may differ from that of the native protein; and (c) the bacterial products may be toxic when added to inmune cells in culture.

SUMMARY OF THE INVENTION

In order to obtain full-length hTPO free of other potential thyroid antigens, the present inventor achieved expression of recombinant hTPO in non-thyroidal eukaryotic cells. Like native hTPO, this recombinant hTPO is enzymatically active, is expressed on the cell surface, and is not a fusion protein.

The recombinant hTPO of this invention is recognized in a specific manner by sera from patients with Hashimoto's thyroiditis that contain "antimicrosomal" antibodies. All 36 Hashinioto patient sera selected to represent a range of antimicrosomal antibody levels seen in this disease were reactive with the eukaryotic-expressed recombinant hTPO of the invention.

It is an object of the present invention, then, to provide for a convenient and economical source of recombinant hTPO, which does not suffer from the disadvantages associated with the immuno-purified native protein or with the recombinant fusion protein previously available. The present invention thus provides a number of important advances in the characterization of the human thyroid microsomal antigen, and opens the way to substantial further developments in this field.

Recombinant, enzymatically-active, human thyroid peroxidase has been generated in non-thyroidal eukaryotic cells. Unlike bacterial fusion proteins previously reported, the conformation of this protein is not encumbered by the β-galactosidase fusion partner. Furthermore, unlike the bacterially-produced protein, the TPO is glycosylated. The demonstration of functional TPO activity indicates unequivocally that the oDNA previously cloned (Magnusson, R.P., et al., *J. Biol. Chem.* 262:13885–13888 (1987); Magnusson, R.P., et al., *Mol. Endocrinol.* 1:856–861 (1987); Libert, R., et al., *EMBO J.* 6:4193–4176 (1987); Kimira, S., et al., *Proc. Natl. Acad. Sci. USA* 84:5555–5559 (1987)), is indeed TPO.

The present invention also provides for the identification of the β-cell epitope on thyroid peroxidase associated with autoimnune thyroid disease. In addition, this aspect of the invention provides a method for identifying the molecular interaction responsible for the β-cell recognition of thyroid peroxidase.

Experiments using the recombinant hTPO of the invention expressed in a non-thyroidal eukaryotic cell prove that TPO, independent of any other potential thyroid antigen, is a major autoantigen in Hashimoto's thyroiditis. Thus, all 36 Hashimoto's patient sera tested reacted specifically with recombinant hTPO in an approximately quantitative manner as demonstrated by Western blot analysis. While previous immunological studies strongly suggested that antimicrosomal antibodies react with hTPO (Czarnocka, B., *FEBS Letters* 109:147–152 (1985); Portmann, L., et al., *J. Clin. Endocrinol. Metab.* 61:1001–1003 (1985); Kotani, T., et al., *J. Clin. Endocrinol. Metab.* 62:928–933 (1986); Mariotti, S., et al., *J. Clin. Endocrinol. Metab.* 65:981–993 (1987)), it had been difficult to exclude the possibility of contamination of the inhunopurified hTPO antigen by other, unidentified, thyroid antigens. The only thyroidal (or, indeed, human) protein produced by, or found in, the CHO-TPO cells of the present invention is hTPO. Even though human sera from both normal subjects and patients with Hashmoto's thyroiditis contain antibodies that react with some antigen(s) of untransfected CHO cells, only the Hashimoto's patient sera react with the recombinant hTPO.

The present invention also sheds light on previous observations that the microsomal antigen appeared as a doublet when analyzed by polyacrylaulde gel electrophoresis (PAGE) and Western blot (Portmann, L., et al., *J. Clin. Invest.* 81:1217–1224 (1988); Hamada, N., et al., *J. Clin. Endocrinol. Metab.* 6:120–128 (1985); Hamada, N., et al.,) *J. Clin. Invest.* 79:819–825 (1987). It was not known whether the doublet represented two separate proteins or the partial degradative product of a single protein. Kimura et al. observed two forms of hTPO mRNA and cDNA, and suggested the possibility of alternate splicing of the initial TPO transcripts (Kimura, S.. et al., *Proc. Natl. Acad. Sci. USA* 84:5555–5559 (1987)). Nagayama et al. reported the existence of four different forms of hTPO mRNA transcripts in cultured Graves' thyroid cells after TSH stimulation (Nagayama, Y. et al., *International Thyroid Symposium*, Tokyo, Japan, Abstract #42 (1988)). The present discovery of a doublet as the product of a single, intron-less, hTPO gene argues strongly against the likelihood of alternate splicing.

The apparent conversion of the doublet to a single band after protein reduction, reminiscent of the data of Portmann et al. with a crude human thyroid extract (Portmann, L. et al., *J. Clin. Invest.* 81:1217–1224 (1988)), suggests that membrane-bound hTPO is linked through disulfide bonds to another, unidentified protein. An alternate interpretation, in line with the model of Taurog et al., (Yokoyama, N., et al., *Mol. Endocrinol.* 2:838–844 (1988)), is that intrachain disulfide bonds within TPO may alter the gel migratory behavior of TPO, resulting in the appearance of multiple forms. In contrast to observations of human thyroid microsomes in which the primary antigen (under non-reducing conditions) was 107 kD in size (Hamada, N., et al., *J. Clin. Endocrinol. Metab.* 61:120–128 (1985)), the present inventor observed, under the sane conditions, that the major immunogenic form of recombinant hTPO in transfected CHO cells is about 200 kD in mass which is converted upon reduction to a single band of about 110 kD. This difference may be related to varied expression of hTPO in different cell types (human and CHO). However, it was also reported that a 200 kD protein was produced by subjecting the extracted human thyroid microsomal 107 kD protein major band to PACE under non-reducing conditions (Hamada, N., et al., *J. Clin. Endocrinol. Metab.* 61:120–128 (1985)). Also, the present finding of a diminished 110 kD signal after reduction of the recombinant hTPO protein is in accordance with other findings using the native microsomal antigen (Gardas, A., et al., *J. Endocrinol. Invest.* 11:385–388 (1988); Nakajima, Y., et al., *Mol. Cell. Endocrinol.* 53:15–23 (1987)). Thus, in its native state, human TPO exists either as a multimer or in association with another membrane protein of similar size. Epitope recognition by autoantibodies may be conformation-dependent The derived amino acid sequence of hTPO suggested to the present inventor the presence in recombinant full-length hTPO and thus, in naturally-occurring hTPO, of a signal peptide, as well as a putative hydrophobic membrane-spanning region (transmembrane domain) at the carboxyl terminus of the protein (amino acid residues 846–870) (Magnusson, R.P., et al., *J. Biol. Chem.* 262:13885–13888 (1987); Magnusson, R.P., et al., *Mol. Endocrinol.* 1:856–861 (1987); Kimura, S., et al., *Proc. Natl. Acad. Sci. USA* 84:5555–5559 (1987); Libert, F., et al., *Nucl. Acids Res.* 15:6735 (1987)). Naturally-occurring hTPO has been shown to be a thyroidal cell surface protein. Recombinant, enzymatically active hTPO is also cell membrane-associated in stably transfected non-thyroidal eukaryotic cells (Kaufman, K.D., et al., *J. Clin. Invest.* 84:394–403 (1989)).

While not intending to be bound by a particular theory, the present inventor hypothesized that the signal peptide directs the human TPO through the cell membrane, but that the hydrophobic region of hTPO becomes embedded in the cell membrane, thereby preventing secretion from the cell.

There has heretofore been no functional proof that the hTPO hydrophobic region 846–870 corresponds to a transmembrane domain. The present invention demonstrates the existence of a transmembrane domain in hTPO, and that hTPO is predominantly an enzyme with an extracellular orientation. The insertion, by site-directed mutagenesis, of a stop codon immediately upstream of this putative transmembrane domain converts hTPQ into a secreted protein that is enzymatlcally active and immunologically intact. By introducing the stop codon, the hTPO was truncated by 85 residues, removing the carboxyl terminus (933 amino acids). Mutated hTPO cDNA, inserted into a eukaryotic expression vector, was stably transfected into CHO cells. Immunoprecipitation and PAGE of cellular $^{35}$S-methionine-labeled proteins with Hashimoto's patient serum revealed a 105–101 kD doublet. In contrast, cells transfected with wild-type hTPO yielded a 112–105 kD doublet.

In pulse-chase experiments, CHO cells expressing the truncated hTPO protein secreted immunoprecipitable TPO into the culture medium after 4 hours of chase, with levels accumulating progressively over a 24 hour period. In contrast, CHO cells expressing wild-type hTPO released no immunoprecipitable TPO into the culture medium. The secreted, truncated form of hTPO appeared as a single band of lesser electrophoretic mobility, as opposed to the doublet expressed within cells. TPO enzymatic activity was present in conditioned medium from CHO cells transfected with the mutated hTPO, but was absent in conditioned medium from cells expressing wild-type hTPO. The stability of the mutated protein appeared similar to that of wild-type hTPO.

The secreted form of hTPO can be used to generate large amounts of soluble TPO protein for use in structural and immunologlcal studies, as well as for diagnostic uses.

Thus, in one embodiment, there is provided according to the invention recombinant, enzymatically active, TPO, or a functional or chemical derivative thereof.

In another embodiment is provided hTPO produced by non-thyroidal eukaryotic cells.

In another embodiment there is provided according to the invention recombinant hTPO that is enzyuatically active, immunologically intact and secretable, or a functional or chemical derivative thereof.

Yet another embodiment of the invention comprises a plasmid selected from the group consisting of pECE-HTPO, pHTPO(M1)-ECE-SV2-DHFR, pHTPO-DHFR-2B, pHTPO-DHFR-4C and pHTPO-DHFR-4C-MTX.

There is also provided according to the invention a non-thyroidal eukaryotic cell transformed with any of these plasmids, as well as methods of producing hTPO comprising culturing the transformed cell under conditions allowing expression of the hTPO and recovering the hTPO.

In yet another embodiment, the invention provides for an antibody against the hTPO of the invention.

Further, a method of detecting hTPO in a sample is provided according to the present invention, comprising contacting the sample with an antibody against full-length recombinant hTPO or an antibody against a secretable hTPO, wherein the antibody is detectably labeled, so as to form a complex between the hTPO in the sample and the detectably labeled antibody, and detecting the complexed or uncomplexed labeled antibody.

In an additional embodiment, there is provided a kit for the detection of hTPO in a sample, comprising container means comprising one or more containers, wherein one of the containers comprises detectably labeled antibody against hTPO.

Further, a method of detecting antibodies to hTPO in a sample is provided according to the present invention, comprising contacting the sample with full-length recombinant hTPO or secretable recombinant hTPO so as to form a complex between an hTPO-specific antibody in the sample and the recombinant hTPO, and detecting the complexed antibody. In an additional embodiment, there is provided a kit for the detection of antibodies to hTPO in a sample, comprising container means comprising one or more containers, wherein one of said containers comprises recombinant hTPO.

These and other non-limiting embodiments of the present invention will be apparent to those of skill from the following detailed description of the invention.

Panel A: Cells exposed to phycoerythrin (PE)-labeled second antibody alone, without prior exposure to human serum.

Panel B: Cells incubated in serum (1:100) from a patient with Hashiznoto's thyroiditis (ELISA value of 1.779) without subsequent incubation in PE-labeled second antibody.

Panel C: Cells sequentially incubated in the Hashimoto's serum described in panel B and in PB-labeled second antibody.

Panel D: As in panel C, except that serum from a normal individual, lacking antimicrosomal antibodies, was used.

Panels E and F: The same data as in panels C and D plotted to show the forward scatter. These data indicate that the relative sizes of the cell populations reacting with the normal and the Nashimoto's sera are the same.

FIG. 3. Linear regression analysis of ELISAs using antibodies against human thyroidal microsoms or against recombinant human TPO.

Figure 4:
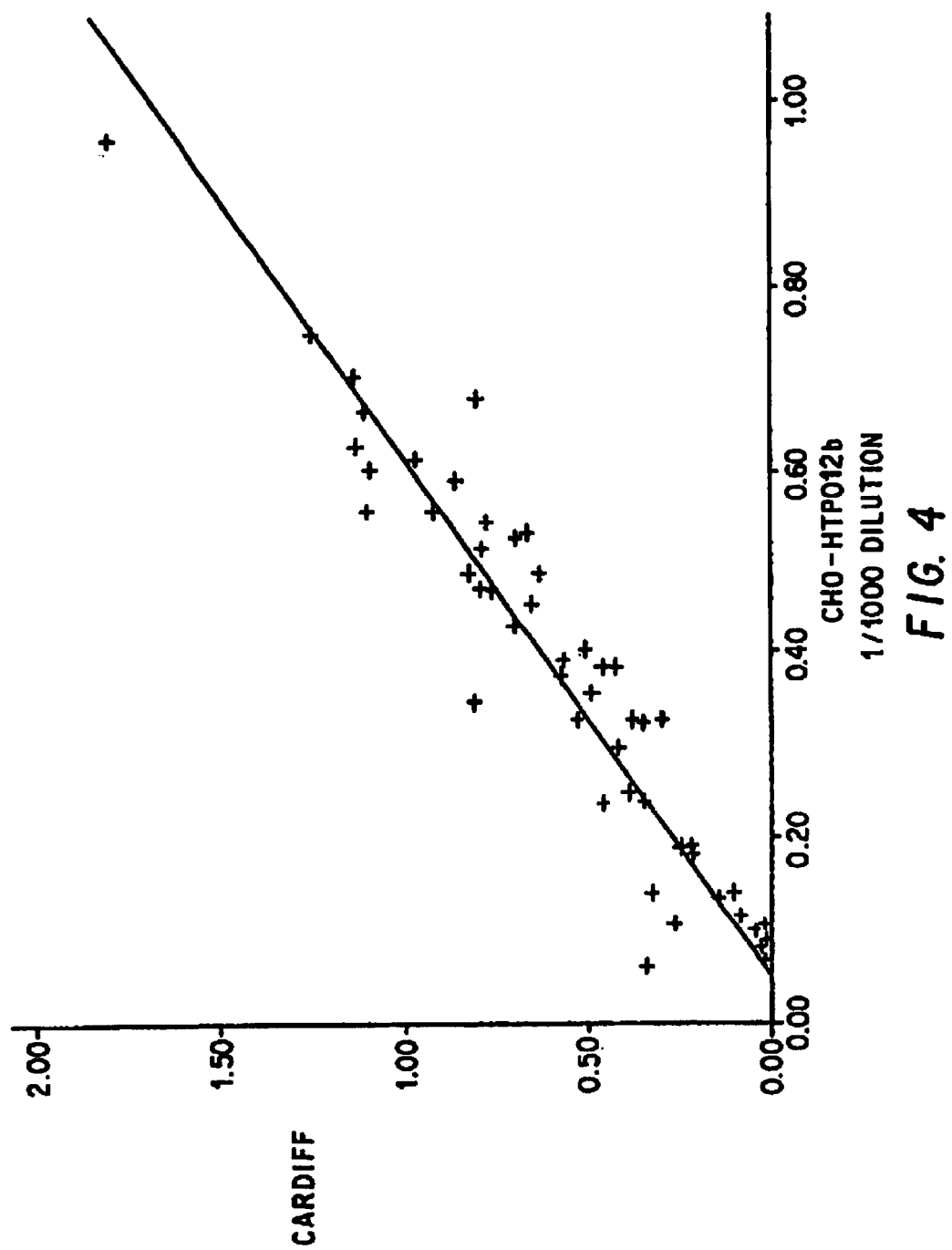

FIG. 4. Linear regression analysis of ELISAs using antibodies against human thyroidal microsomes or against recombinant human TPO, 1/1000 dilution. "Cardiff" refers to the source of the microsomal antigen of both FIGS. 3 and 4.

Figure 5:
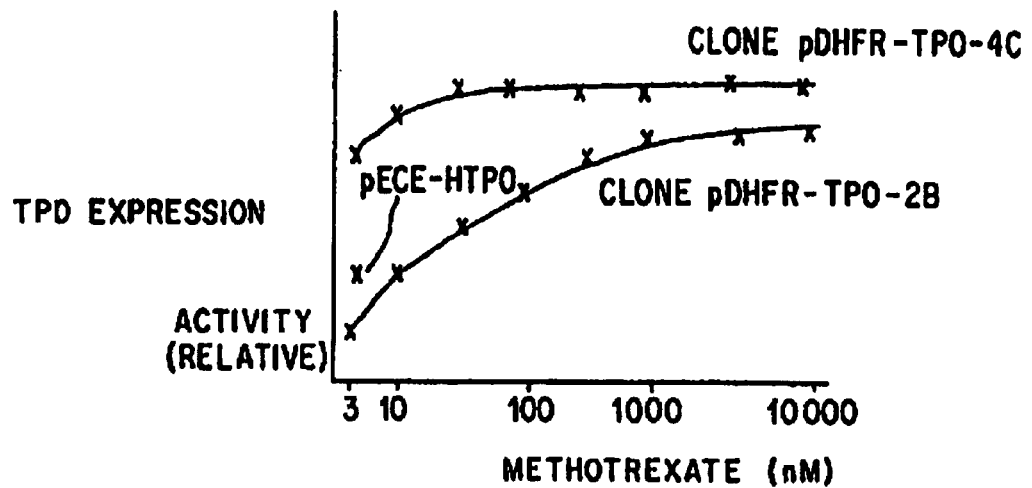

FIG. 5. Relative TPO activities observed in CHO cells transfected with pECE-HTPO, pHTPO-DHFR-2B and pHTPO-DHFR-4C, shown plotted against methotrexate concentration.

FIG. 6. Nucleotide sequence of human TPO gene after site-directed mutagensis (SEQ ID NO: 1). The mutations incorporated two stop codons, as well as an EcoR1site for confirmation, in the region immediately upstream from the transmembrane region of the human TPO gene.

FIG. 7. cDNA sequence (SEQ ID NO: 2) and derived amino acid sequence (SEQ ID NO: 3) of human thyroid peroxidase (Magnusson, R.P., Mol. Endocrinol. 1:856–861 (1987)).

FIG. 7A depicts the cDNA sequence of human thyroid peroxidase from nucleotides 1 to 486, and the amino acid sequence of human thyroid peroxidase from amino acids 1 to 134.

FIG. 7B depicts the cDNA sequence of human thyroid peroxidase from nucleotides 482 to 972, and the amino acid sequence of human thyroid peroxidase from amino acids 135 to 296.

FIG. 7C depicts the cDNA sequence of human thyroid peroxidase from nucleotides 973 to 1458, and the amino acid sequence of human thyroid peroxidase from amino acids 297 to 458.

FIG. 7D depicts the cDNA sequence of human thyroid peroxidase from nucleotides 1459 to 1945, and the amino acid sequence of human thyroid peroxidase from amino acids 459 to 620.

FIG. 7E depicts the cDNA sequence of human thyroid peroxidase from nucleotides 1946 to 2484, and the amino acid sequence of human thyroid peroxidase from amino acids 621 to 800.

FIG. 7F depicts the cDNA sequence of human thyroid peroxidase from nucleotides 2485 to 3072, and the amino acid sequence of human thyroid peroxidase from amino acids 801 to 933. Asterisks (*) indicate potential glycosylation sites. The carets (^^^) at nucleotides 2884, 2885, and 2886 indicate an in phase termination codon. The carets (^^^ ^^^) at nucleotides 3042 to 3048 indicate a polyadenylation signal near the 3'-end.

Figure 8:
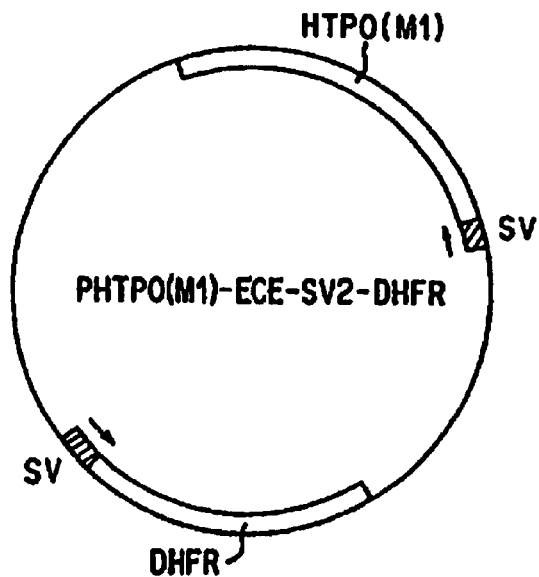

FIG. 8. Schematic diagram showing the expression plasmid pHTPO(M1)-ECE-SV2-DHFR.

Figure 9:
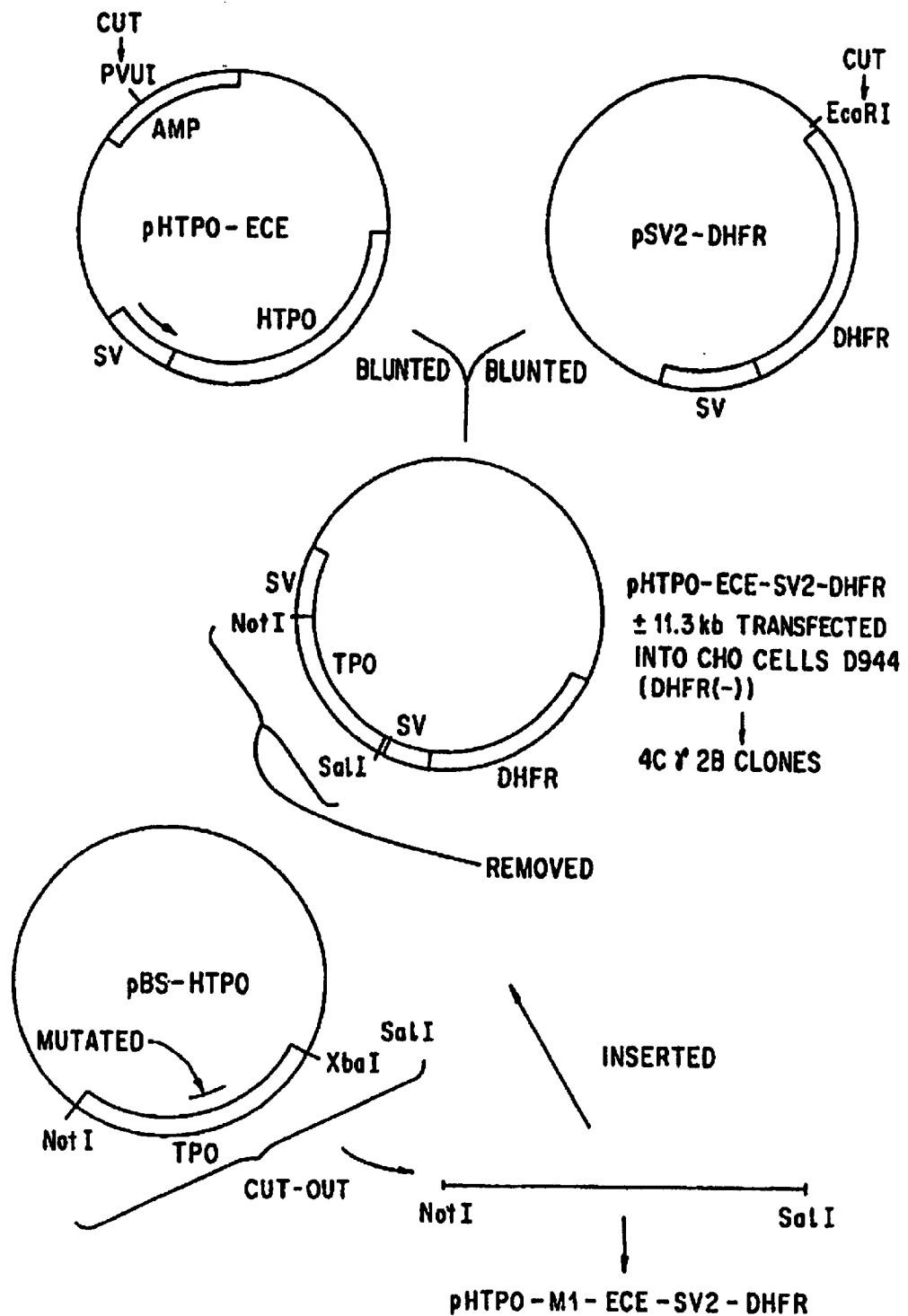

FIG. 9. Construction of the plasmid pHTPO(M1)-ECE-SV2-DHFR.

FIG. 10. Comparison of 51 sera, selected to provide a spectrum of anti-MSA levels, in terms of their reactivity with Graves' thyroid microsomes and recombinant, enzymatically-active human TPO generated In nonthyroldal eukaryotic cells. The anti-MSA assay data are expressed as an ELISA index, relative to a standard serum. Data for the anti-hTPO antibody assay are expressed as absolute O.D. units, normalized to a blank well value of 0.000. (A) serum dilution 1/100 (sera from four normal patients are enclosed within the rectangle); (B) serum dilution 1/1,000; (C) serum dilution 1/10,000.

Figure 11A:
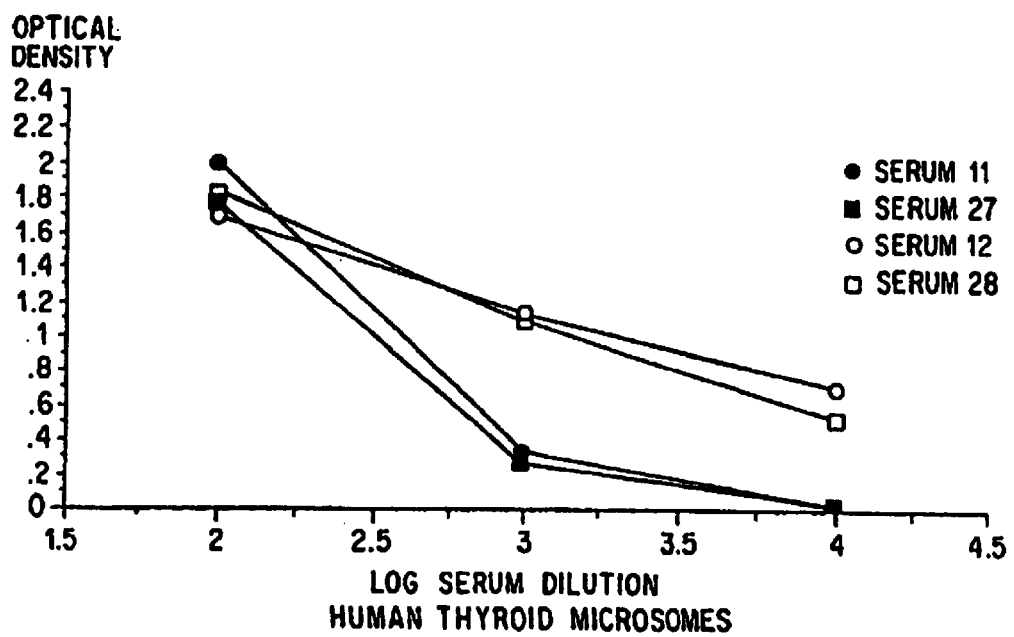
Figure 11B:
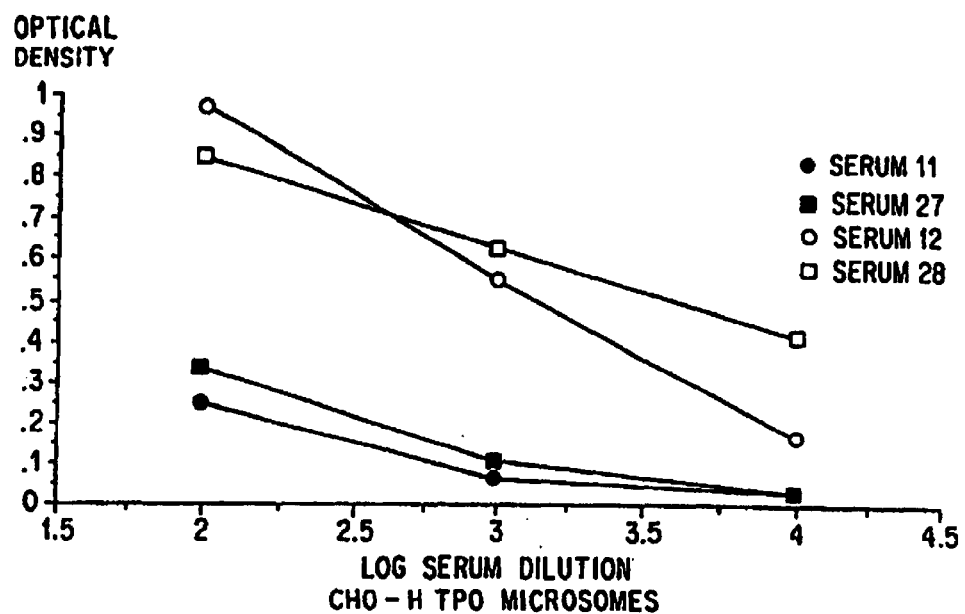

FIG. 11. Two sera (#11 and 27) reacting discrepantly with human thyroid microsomes (A) and recombinant hTPO (B) are reacting with an antigen other than hTPO in panel A at standard (1/100) serum dilution. Dilution curves are also shown for two other sera (#12 and 28) with similar anti-MSA activity at standard serum dilution.

Figure 12:
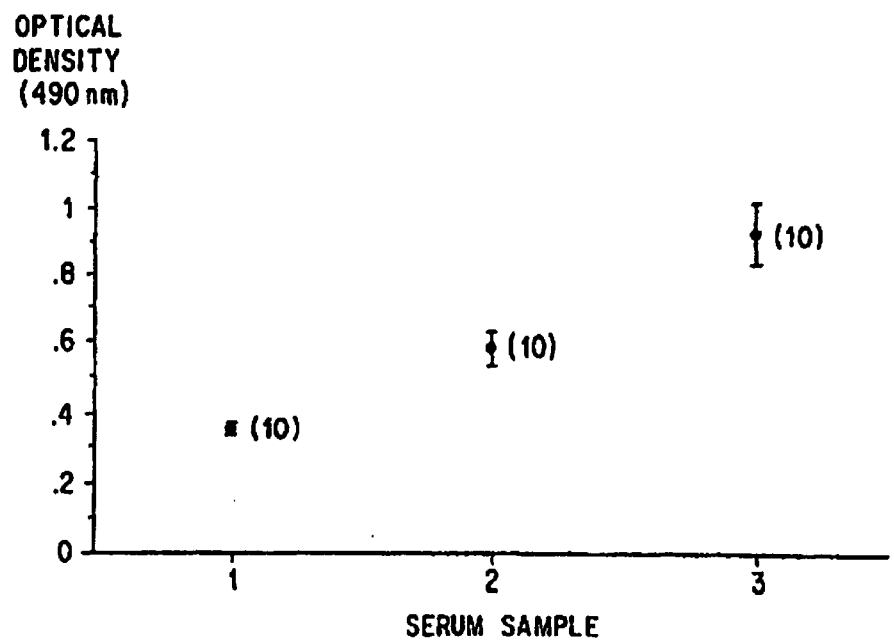

FIG. 12. Intra-assay variability of anti-hTPO antibody ELISA at standard (1/100) serum dilution. Mean ± standard deviation of 10 iterations of anti-hTPO antibody ELISA results for three autoimmune sera selected to represent low, medium, and high autoantibody levels.

Figure 13:
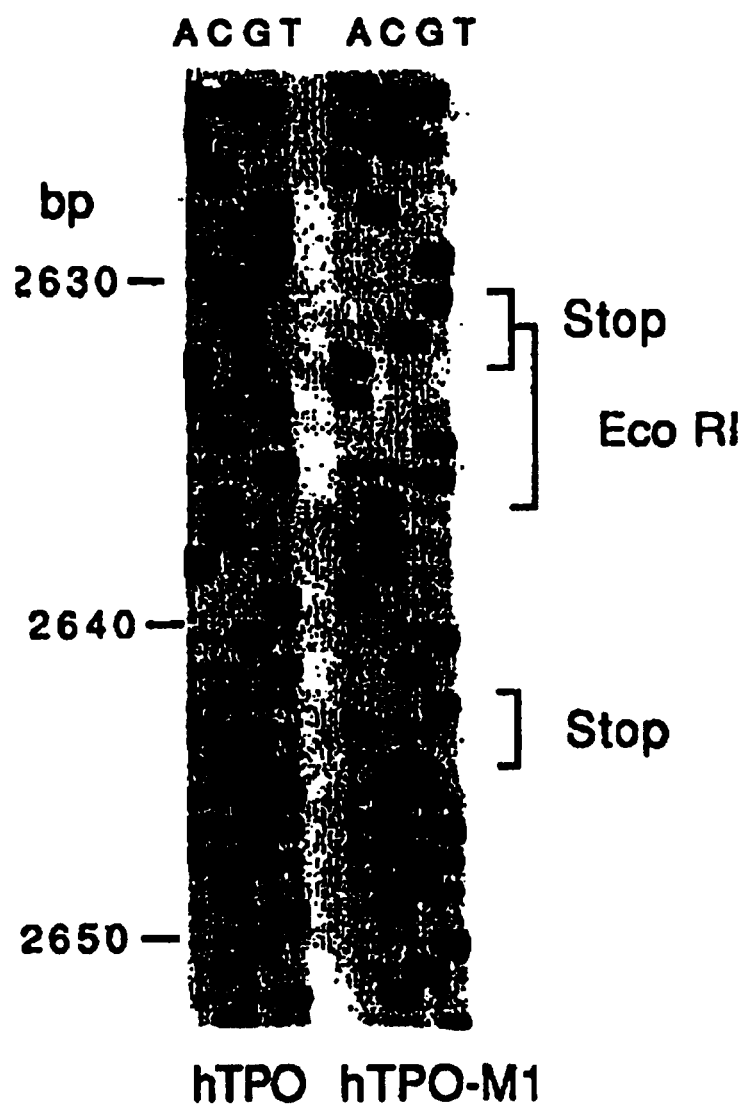

FIG. 13. Confirmation, by nucleotide sequencing, of the mutations introduced into hTPO by site-directed mutagenesis. The nucleotide positions referred to correspond to those reported for human TPO (Rousset,. B., et al., Clin. Exp. Immunol. 52:325–332 (1983)). TGA (2629–2631 bp) and TAG (2641–2643 bp) stop codons, as well as the EcoR1 site, in the mutated hTPO-M1 are shown on the right. The nucleotide sequence of wild-type hTPO is shown on the left.

FIG. 14. (A) Immunoprecipitation of mutated hTPO in different clones of transfected CHO cells. CHO—nontransfected CHO cells; CHO-TPO—CHO cells transfected with wild type hTPO; CHO-TPO-M1-POOLED—pooled colonies of CHO cells transfected with the mutated form of hTPO; CHO-TPO-M1-D through K—individual colonies of CHO cells, transfected with mutated hTPO, that were selected with cloning cylinders and then expanded. Cells were radiolabeled with $^{35}$S-methionine and imunoprecipitated with Hashimoto's thyroiditis serum containing high anti-hTPO antibody levels.

(B) lmmunoprecipitation of mutated hTPO from clones of CHO-TPO-M1-K cells generated by limiting dilution. Immunoprecipitations were performed with serum from a patient with Hashimoto's thyroiditis with high anti-hTPO antibody levels. The specificity of the immunopreclpitation is shown by the inability of serum from a normal individual (CON) to precipitate the 105–101 kD doublet.

Figure 15:
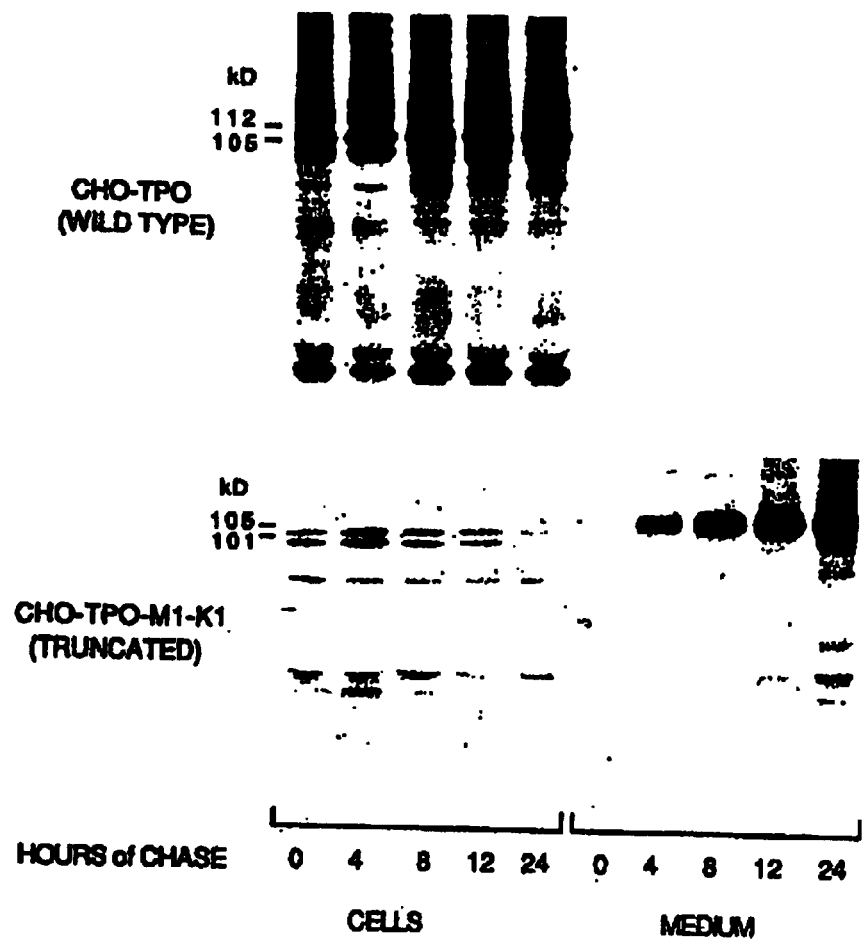

FIG. 15. Biosynthesis and processing of TPO. Immunoprecipitation studies were performed with CHO cells expressing wild-type hTPO (upper panel), and with CHO cells transfected with the mutated form of hTPO (lower panel). Pulse for 4 h (0 hours of chase) with $^{35}$S-methionine was followed by chase with unlabeled methionine for the indicated periods of time. Immunoprecipitations were then performed on both cell lysates and conditioned media, as indicated.

Figure 16:
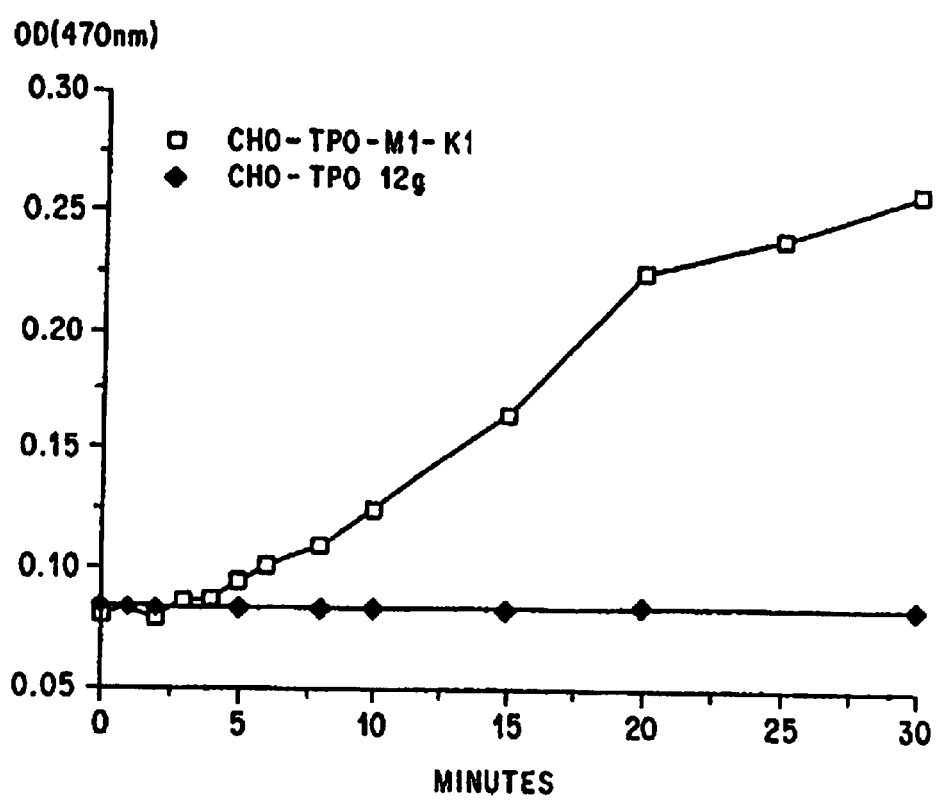

FIG. 16. Human TPO enzymatic activity in the medium of CHO cells after transfection with wild-type hTPO (cell line CHO-TPO 12 g) (Kotani, T., et al., J. Clin. Endocrinol. Metab. 62:928–933 (1986)) and CHO cells transfected with the mutated form of hTPO (CHO-TPO-M1-K1). Media were collected after 3 days of culture. TPO enzymatic activity in the media was measured by the gualacol assay. The time course shown refers to the accumulation of oxidized gualacol substrate in the assay, and not to the kinetics of enzyme secretion into the medium.

FIG. 17. (A) T cell clones from the thyroid infiltrate in Graves' disease, expanded in the absence of antigen, recognize recombinant TPO. Clone+autologous irradiated PBL–black bars; clone+PBL+control (untransfected) CHO microsomes–striped bars; clone+PBL+CHO microsomes transfected with TPO–grey bars. Results are expressed as mean cpm of [$^{3}$H]thymldine incorporation from triplicate cultures. Error bars indicate standard errors of the mean (S.E.M). Similar results were obtained in three or more replicate experiments.

(B) Peripheral blood lymphocytes from both patients and normal subjects proliferate in response to both control and TPO-transfected microsomes. PBL alone–black bars; PBL+ control microsomes–striped bars; PBL+TPO transfected microsomes–grey bars. Results are expressed as mean cpm [$^{3}$H]thymidine incorporation of triplicate cultures (Error bars indicate S.E.K.) 81—patient from whom T cell clones in FIG. 17A were derived; RG—another female with Graves' disease; KH—normal control female. Similar results have been obtained from other individuals in separate experiments.

Figure 18:
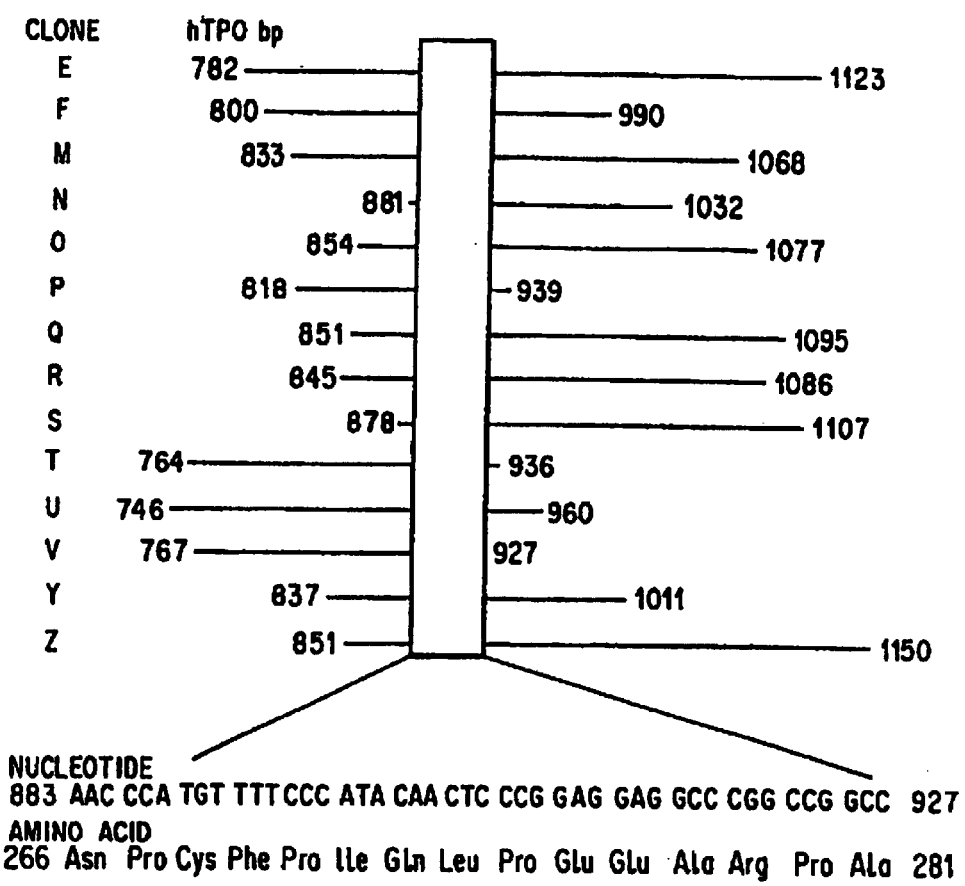

FIG. 18. Determination of the epitope for the anti-microsomal/TPO monoclonal antibody 20.10. The nucleotide sequences of the 5'- and 3'-ends were determined for 14 clones selected from tTPO cDNA fragment library. These boundaries are annotated by the numbers assigned to the nucleotides in hTPO previous reported (Magnusson, R.P., et al., Mol. Endocrinol. 1:856–861 (1987). The smallest region of overlap between all 14 clones is f 881–927 b.p. The first two nucleotides in this span do not constitute a complete codon, so the epitope area can be defined as between 883–927 b.p. (SEQ ID NO: 4), corresponding to the derived amino acid sequence shown (SEQ ID NO:5).

FIG. 19. Determination of the epitope recognized by TPO MAb 47. The nucleotide sequences of the 5'- and 3'-prime ends were determined for 18 clones in the TPO cDNA fragment library (see Materials and Methods) recognized by MAb 47. The smallest region of overlap between all 18 clones is from 2219–2247 (SEQ ID NO: 6) basepairs in the human TPO cDNA sequence, coding for the indicated amino acids (SEQ ID NO: 7).

FIG. 20. Western blot analysis of human TPO, using TPO MAb. Recombinant human TPO expressed in Chinese hamster ovary cells was used as antigen under denaturing and reducing conditions (see Materials and Methods). After polyacrylamide gel electrophoresis and transfer to the membranes, the membranes were probed with the indicated antibodies. TPO MAb 1, 2, 9, 15, 18, 24, 30, 40, 47, 53, 59, 60 and 64 are mouse MAbs generated against native undenatured human TPO (Ruf, J., et al., *Endocrinology* 125:1211–8 (1989)). The controls (Con) are mouse MAbs raised against denatured human TPO (Portmann, L., et al., *J. Clin. Invest.* 1:1217–1224 (1988)) (A and B) and control mouse ascitic fluid (C). The sizes of the mol wt markers are shown on the left, and that of recombinant human TPO is indicated by the arrow.

Figure 21:
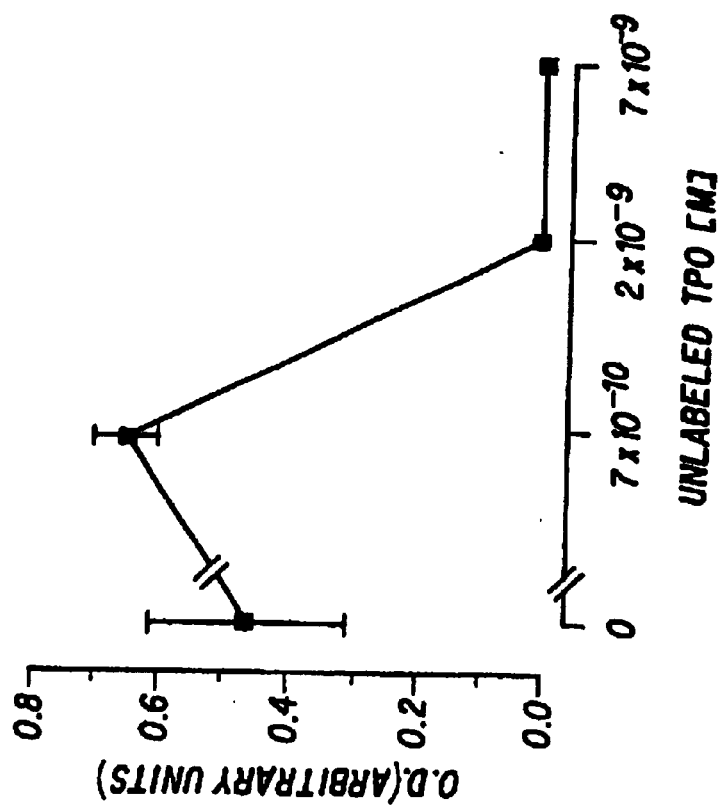

FIG. 21: Binding affintiy of Fab fragment SP2 for recombinant human thyroid peroxidase (TPO). Brackets indicate the mean ± the range of duplicate densitometric values obtained for each TPO concentratin in a representative experiment. Comparable results were obtained in two additional experiments.

Figure 22B:
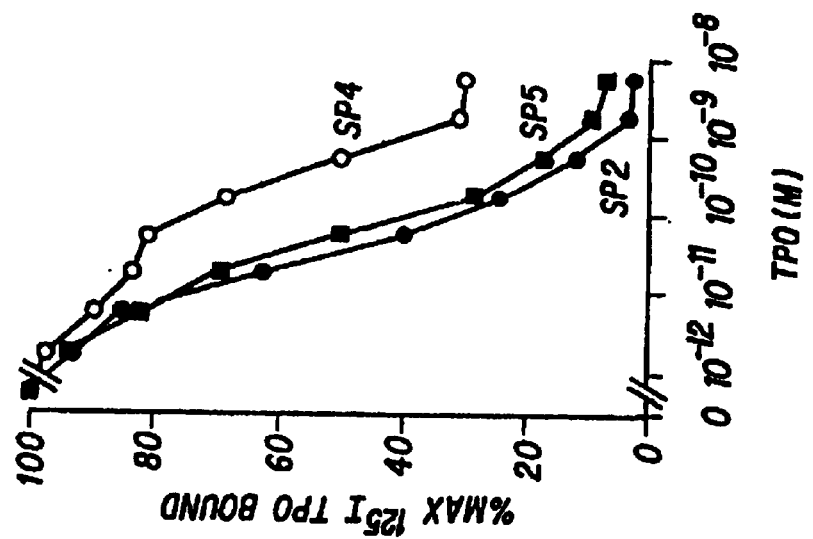
Figure 22A:
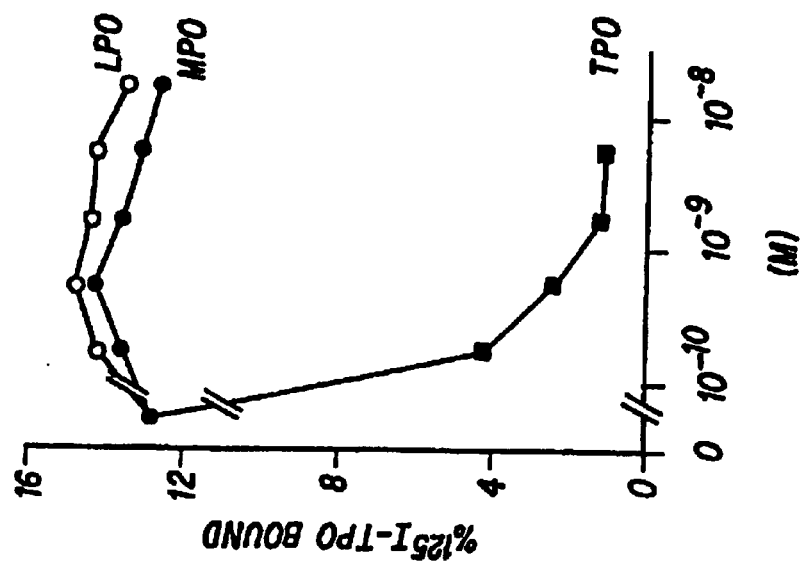

FIGS. 22A to 22B: FIG. 22A. Effect of increasing molar (M) concentrations of TPO, lactoperoxidase (LPO) or myeloperoxidase (MPO) on the binding $^{125}$I-TPO by SP1.2. Background binding in the absense of Fab fragments (~2%) was subtracted.

FIG. 22B. Competition inhibition by unlabeled TPO of radiolabed TPO binding to the Fab fragments. In the absence of unlabeled TPO, binding values for the three Fab fragments were 13–15%. Background of ~2% was subtracted. Dissociation constants (Kd) were determined by Scatchard analysis (Scatchard, G., "The attractions of proteins for small molecules and ions," Ann. NY Acad. Sci. VOL 51:660–672 (1949)) and are:

$$SP2=8.3\times10^{-11}M; SP4=2.2\times10^{-10}M; SP5=3\times10^{-11}M$$

Figure 23:
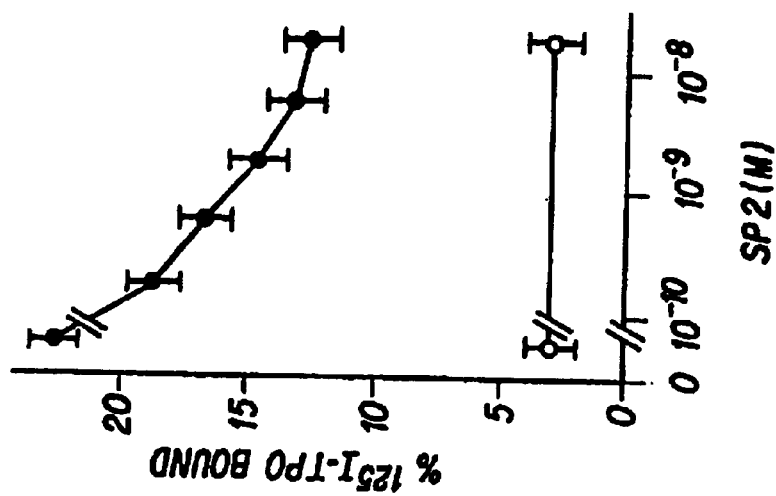

FIG. 23: Inhibition by increasing molar (M) concentrations of SP1.2 on the binding to $^{125}$I-TPO by serum TPO autoantibodies. The mean values (± S.E.M.) obtained for sera from 11 patients are shown by solid circles. Background binding by serum from TPO autoantibody negative donor was not subtracted and is shown by the open circles (mean ± S.E.M. of 3 experiments).

Figure 24B:
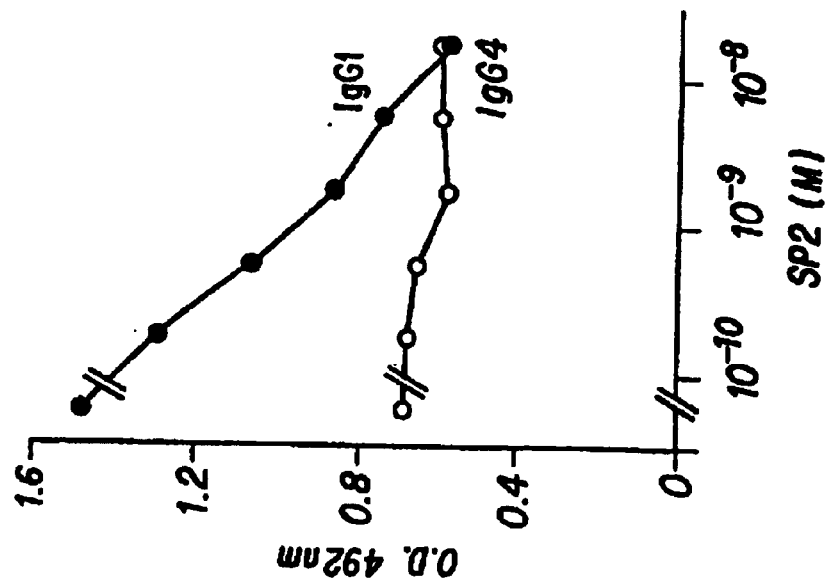
Figure 24A:
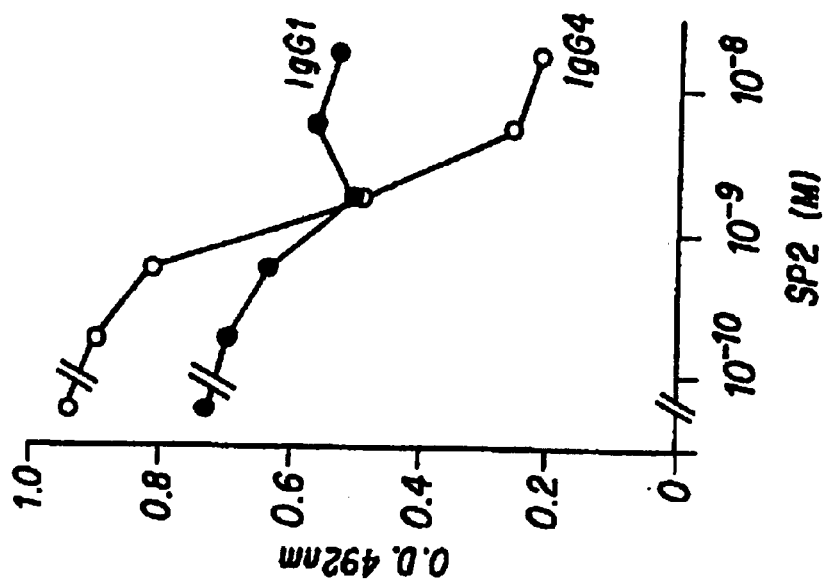
Figure 24C:
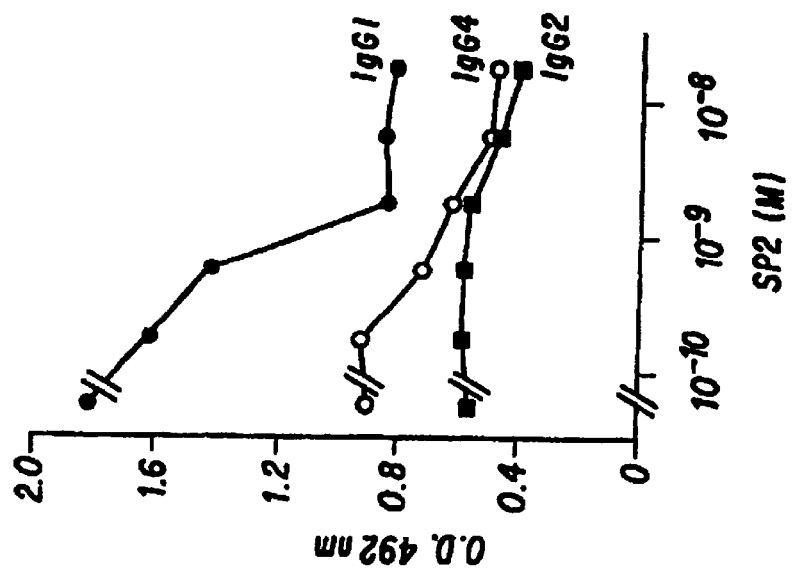

FIGS. 24A to 24C: Competition ELISA for binding to TPO between the SP1.2 Fab fragment and TPO autoantibodies of different IgG subclasses. FIGS. 24A to 24C show data obtained with three different patients. TPO autoantibodies levels are shown as the O.D. readings measured at 492 nm. Background O.D. values obtained for TPO autoantibody-negative serum were <0.05. SP1.2 (M); molar concentration of SP1.2.

Figures 25A, 25B:
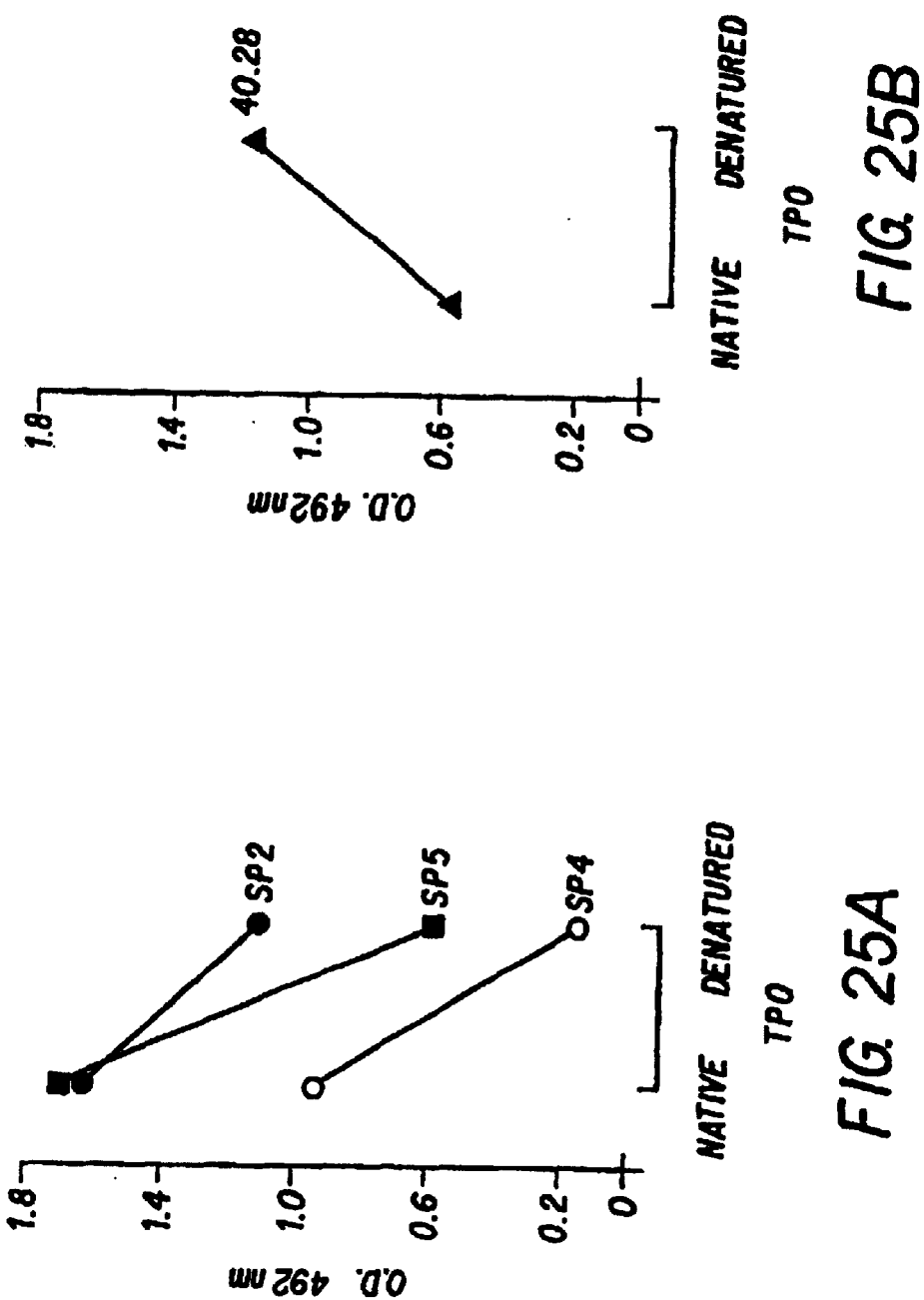

FIGS. 25A to 25B: Effect of denaturation of TPO on SP Fab fragment binding. Binding SP1.2, SP1.4 and SP1.5 FIG. 25A or mouse monoclonal antibody #40.28 FIG. 25A was measured to native or denatured TPO by ELISA. Binding is shown as the O.D. value at 492 nm. Background O.D. values for TPO autoantibody negative serum and control murine ascites were <0.05.

Figure 26:
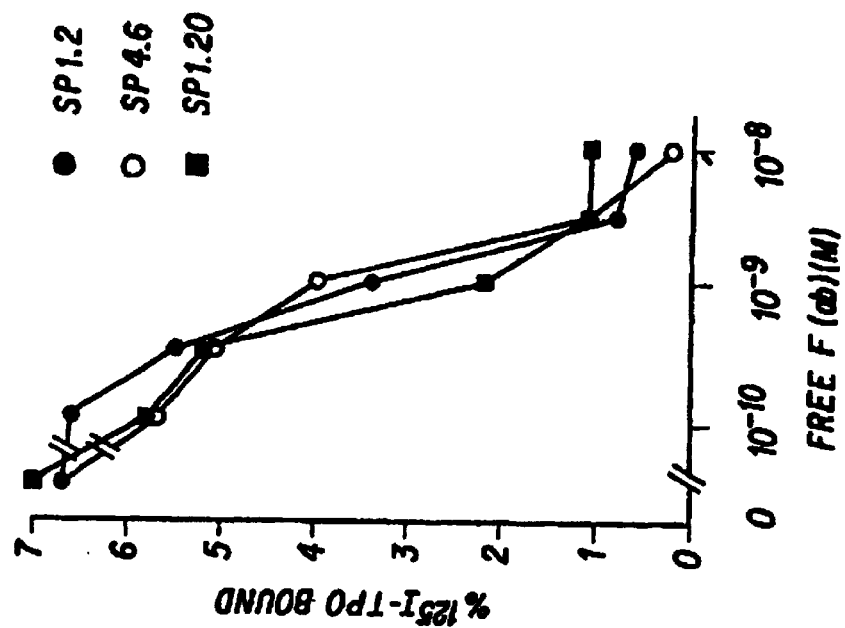

FIG. 26: Binding domains on TPO for the SP1.2, SP4.6, SP1.20 F(ab)s. $^{125}$I-TPO was preincubated in the absence or presence of increasing concentrations of SP4.6, SP1.20 or SP1.2 [Free F(ab)]. The ability of these complexes to bind to immobilized SP1.2 was then determined. The results are expressed as % $^{125}$I-TPO bound after subtraction of background values (~2%) obtained using buffer alone.

FIGS. 27A to 27D: Domains on TPO recognized by F(ab)s. Increasing concentrations of one F(ab) were preincubated with radiolabeled TPO and then added to a second, immobilized F(ab) (Methods). The immobilized F(ab) was TR1.9 FIG. 27A, TR1.7 FIG. 27C and SP1.5 FIG. 27D. The ability of the free F(ab) to inhibit binding to itself is shown by the open circles. Confirmation of the binding potency of the free F(ab)s was determined concurrently in each experiment. A representative control FIG. 27B for the experment in FIG. 27A. is shown.

FIG. 28: Schematic representation of the binding domains on TPO for the expressed F(ab)s.

Figure 29B:
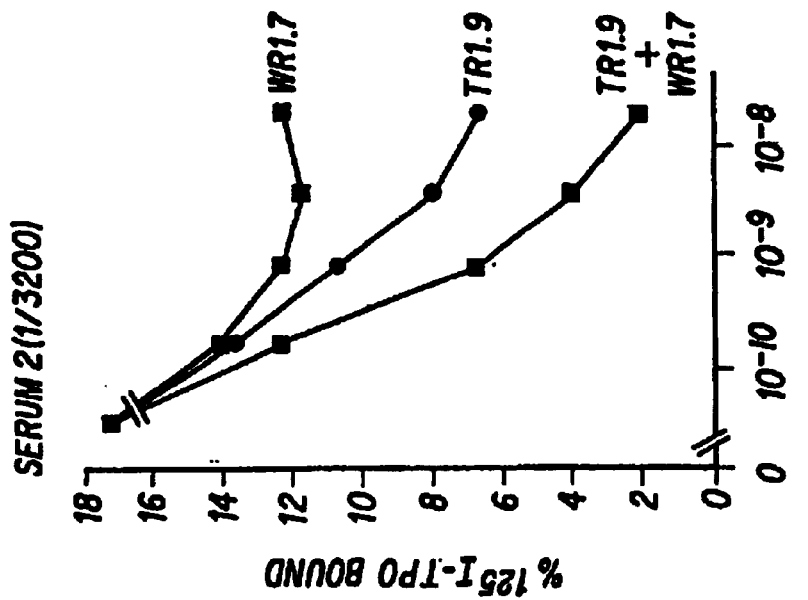
Figure 29A:
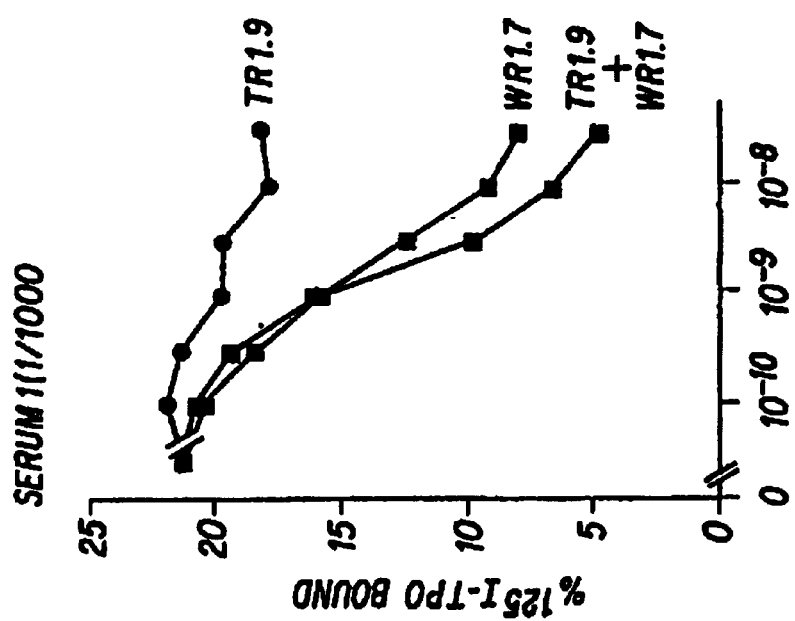
Figure 29C:
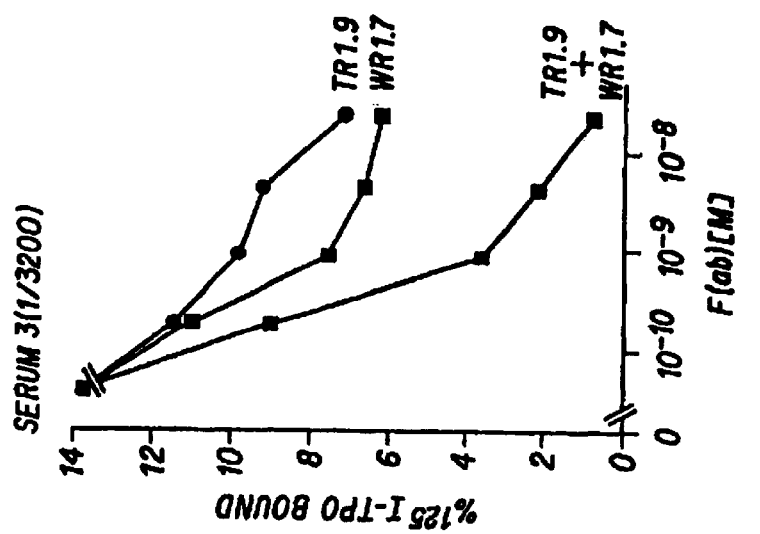

FIGS. 29A to 29C: Domains on TPO recognized by autoantibodies in 3 representative sera FIGS. 29A, 29B and 29C from patients with autoimmune thyroid diseas. F(ab)s WR1.7 and TR1.9, alone or in combination, were used to compete for serum autoantibody binding to radiolabeled TPO (Methods).

DESCRIPTION OF THE PREFERRED EMBODIMENTS

In the following description, reference will be made to various methodologies known to those of skill in the art of molecular biology and immunology. Publications and other materials setting forth such known methodologies to which reference is made are incorporated herein by reference in their entireties as though set forth in full.

Standard reference works setting forth the general principles of recombinant OKA technology include Watson, J.D. et al., *Molecular Biology of the Gene*, Volumes I and II, The Benjamin/Cummings Publishing Company, Inc., publisher, Menlo Park, Calif. (1987); Darnell, J.E. et al., *Molecular Cell Biology*, Scientific American Books, Inc., publisher, New York, N.Y. (1986); Lewin, B.M., *Genes II*, John Wiley & Sons, publishers, New York, N.Y. (1985); Old, R.W., et al., *Principles of Gene Manipulation: An Introduction to Genetic Engineering*, 2d edition, University of California Press, publisher, Berkeley, Calif. (1981); and Maniatis, T., et al., *Molecular Cloning: A Laboratory Manual*, Cold Spring Harbor Laboratory, publisher, Cold Spring Harbor, N.Y. (1982).

By "cloning" is meant the use of in vitro recombination techniques to insert a particular gene or other DNA sequence into a vector molecule. In order to successfully clone a desired gene, it is necessary to employ methods for generating DNA fragments, for jJoining the fragments to vector molecules, for introducing the composite DNA molecule into a host cell In which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise the entire genome of an organism. Such a cDNA library may be prepared by methods known to those of skill, and described, for example, in Maniatis et al., *Molecular Cloning: A Laboratory Manual*, supra. Generally, RNA is first isolated from the cells of an organism from whose genome it is desired to clone a particular gene. Preferred for the purposes of the present invention are mammalian, and particularly human, cell lines. A presently preferred vector for this purpose is the λ-ZAP vector.

By "vector" is meant a DNA molecule, derived from a plasaid or bacteriophage, into which fragments of DNA may be inserted or cloned. A vector will contain one or more unique restriction sites, and may be capable of autonomous replication in a defined host or vehicle organism such that the cloned sequence is reproducible. Thus, by "DNA expression vector" is meant any autonomous element capable of replicating in a host independently of the host's chromosome, after additional sequences of DNA have been incorporated into the autonomous element's genome. Such DNA expression vectors include bacterial plasmids and phages.

By "substantially pure" is meant any antigen of the present invention, or any gene encoding any such antigen, which is essentially free of other antigens or genes, respectively, or of other contaminants with which it might normally be found in nature, and as such exists in a form not found in nature. By "functional derivative" is meant the "fragments," "variants," "analogs," or "chemical derivatives" of a molecule. A "fragment" of a molecule, such as any of the cDNA sequences of the present invention, is meant to refer to any nucleotide subset of the molecule. A "variant" of such molecule is meant to refer to a naturally occurring molecule substantially similar to either the entire molecule, or a fragment thereof. An "analog" of a molecule is meant to refer to a non-natural molecule substantially similar to either the entire molecule or a fragment thereof.

A molecule is said to be "substantially similar" to another molecule if the sequence of amino acids in both 20 molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences*, 16th ed., Mack Publishing Co., Easton, Pa. (1980).

Similarly, a "functional derivative" of a gene of the human TPO antigen of the present invention is meant to include "fragments," "variants," or "analogues" of the gene, which say be "substantially similar" in nucleotide sequence, and which encode a molecule possessing similar activity.

A DNA sequence encoding the human thyroid peroxidase of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra and are well known in the art.

By "secretion" of recombinant hTPO for the purposes of the present invention, it is meant that the recombinant hTPO expressed by a host cell is directed through and dissociated from the host cell membrane.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences Involved with initiation of transcription and translation, such as the TATA box, capping sequence, CAAT sequence, and the like.

If desired, the non-coding region 3' to the gene sequence coding for the protein my be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a human thyroid peroxidase encoding sequence) are said to be operably linked if the nature of the linkage between the two DNA sequences does not (1) result in the introduction of a frame-shift mutation, (2) interfere with the ability of the promoter region sequence to direct the transcription of the thyroid peroxidase gene sequence, or (3) interfere with the ability of the thyroid peroxidase gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

The present invention encompasses the expression of the human thyroid peroxidase protein (or a functional derivative thereof) in either prokaryotic or eukaryotic cells, although eukaryotic (and, particularly, non-thyroidal eukaryotic) expression is preferred.

Preferred prokaryotic hosts include bacteria such as *E. coli, Bacillus, Streptomyces, Pseudomonas, Salmonella, Serratia*, etc. The most preferred prokaryotic host is *E. coli*. Other enterobacteria such as *Salmonella typhimurium* or

*Serratia marcescens*, and various *Pseudomonas* species may also be utilized. Under such conditions, the protein may not be glycosylated. The procaryotic host must be compatible with the replicon and control sequences in the expression plasmid.

To express the human thyroid peroxidase protein (or a functional derivative thereof) in a prokaryotic cell (such as, for example, *E. coli, B. subtilis, Pseudomonas, Streptomyces*, etc.), it is necessary to operably link the human TPO encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage λ ($P_L$ $P_R$), the trp, recA, lacZ, lacI, and gal promoters of *E. coli*, the α-amylase (Ulmanen, I., et al., *J. Bacteriol.* 162:176–182 (1985)) and the σ-28-specific promoters of *B. subtilis* (Gilman, M.Z., et al., *Gene*32:11–20 (1984)), the promoters of the bacteriophages of *Bacillus* (Gryczan, T.J., In: *The Molecular Biology of the Bacilli*, Academic Press, Inc., N.Y. (1982)), and *Streptomyces* promoters (Ward, J.M., et al. *Mol. Gen. Genet.* 203:468–478 (1986)). Prokaryotlc promoters are reviewed by Glick, B.R., (*J. Ind. Microbial.* 1:277–282 (1987)); Cenatiempo, Y. (*Biochimi* 68:505–516 (1986)); and Gottesman, S. (*Ann. Rev. Genet.* 11:415–442 (1984)).

Proper expression in a prokaryotic cell also requires the presence of a ribosome binding site upstream of the gene-encoding sequence. Such ribosome binding sites are disclosed, for example, by Gold, L., et al., (*Ann. Rev. Microbiol.* 35:365–404 (1981)).

Most preferred hosts are eukaryotic hosts including yeast, insects, fungi, and mammalian cells either in vivo, or in tissue culture. Mammalian cells provide post-translational modifications to protein molecules including correct folding or glycosylation at correct sites. Mammallan cells which may be useful as hosts include cells of fibroblast origin such as VERO or CHO-K1, or cells of lymphoid origin, such as the hybridama SP2/O-AG14 or the myeloma P3x63Sg8, and their derivatives. CHO cells are presently preferred mamallan host cells. COS cells also are convenient eukaryotic hosts for human thyroid peroxidase expression, as well as for study of the regulation of human thyroid peroxidase expression.

For a mammalian cell host, many possible vector systems are available for the expression of human TPO. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensItive so that by varying the temperature, expression can be repressed or initiated, or are subject to chemical regulation, e.g., metabolite.

Yeast provides substantial advantages in that it can also carry out post-translational peptide modifications including glycosylatlon. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

Further, by use of, for example, the yeast ubiquitin hydrolase system, in vivo synthesis of ubiquitin-human TPO fusion proteins may be accomplished. The fusion proteins so produced may be processed in vivo or purified and processed in vitro, allowing synthesis of the human TPO protein with a specified amino terminus sequence. Moreover, problems associated with retention of initiation codon-derived methionine residues in direct yeast (or bacterial) expression may be avoided. Sabin et al., *Bio/Technol.* 7(7): 705–709 (1989); Miller et al., *Bio/Technol.* 7(7): 698–704 (1989).

Any of a series of yeast gene expression systems incorporating promoter and termination elements from the actively expressed genes coding for glycolytic enzymes produced in large quantities when yeast are grown in mediums rich in glucose can be utilized. Known glycolytic genes can also provide very efficient transcriptional control signals. For example, the promoter and terminator signals of the phosphoglycerate kinase gene can be utilized.

Production of human TPO or functional derivatives thereof in insects can be achieved, for example, by infecting the insect host with a baculovirtis engineered to express human TPO by methods known to those of skill. Thus, in one embodiment, sequences encoding human TPO may be operably linked to the regulatory regions of the viral polyhedrin protein (Jasny, *Science* 238: 1653 (1987)). Infected with the recombinant baculovirus, cultured insect cells, or the live insects themselves, can produce the human TPO protein in amounts as great as 20 to 50% of total protein production. When live insects are to be used, caterpillars are presently preferred hosts for large scale human TPO production according to the invention.

As discussed above, expression of the human thyroid peroxidase protein in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365(1982)); the SV40 early promoter (Benoist, C., et al., *Nature (London)* 290:304–310 (1981)); the yeast gal4 gene promoter (Johnston, S.A., et al., *Proc. Natl. Acad. Sci. (USA)* 79:6971–6975 (1982); Silver, P.A., et al., *Proc. Natl. Acad. Sci. (USA)* 81:5951–5955 (1984)). Of these, presently the most preferred is the SV40 promoter.

As is widely known, translation of eukaryotic RNA is initiated at the codon which encodes the first methionine. For this reason, it is preferable to ensure that the linkage between a eukaryotic promoter and a DNA sequence which encodes the human TPO protein (or a functional derivative thereof) does not contain any intervening codons which are capable of encoding a methionine (i.e., AUG). The presence of such codons results either in a formation of a fusion protein (if the AUG codon is in the same reading frame as human TPO encoding DNA sequence) or a frame-shift mitation (if the AUG codon is not in the same reading frame as the human TPO encoding sequence).

The human TPO encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the human TPO protein may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Mol. Cel. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColEl, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). *Bacillus* plasmids include pC194, pC221, pT127, etc. Such plasmids are disclosed by Gryczan, T. (In: *The Molecular Biology of the Bacilli*, Academic Press, NY (1982), pp. 307–329). Suitable *Streptomyces* plasmids include pIJ101 (Kendall, K. J., et al., *J. Bacteriol.* 169:4177–4183 (1987)), and streptomyces bacteriophages such as φC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 1:693–704 (1986)), and Izaki, K. (*Jpn. J. Bacteriol.* 33:729–142 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory. Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise. Vol.* 3. *Gene Expression*, Academic Press, NY, pp. 563–608 (1980)).

Once the vector or DNA sequence containing the constructs) has been prepared for expression, the vector or DNA construct(s) may be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile (biolistic) bombardment (Johnston et al., *Science* 240(4858); 1538 (1988)), etc.

After the introduction of the vector, recipient cells are grown in a selective medium, which selects for the growth of vector-containing cells. Expression of the cloned gene sequence(s) results in the production of the human TPO protein, or in the production of a fragment of this protein. This can take place in the transformed cells as such, or following the induction of these cells to differentiate.

The expressed protein may be isolated and purified in accordance with conventional conditions, such as extraction, precipitation, chromatography, affinity chromatography, electrophoresis, or the like. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, the human TPO or functional derivative thereof may be isolated by the use of anti-human TPO antibodies. Such antibodies may be obtained by well-known methods, some of which as mentioned hereinafter.

Antibodies Specific for hTPO

The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)).

Antibodies according to the present invention may be prepared by any of a variety of methods. For example, cells expressing the human TPO protein, or a functional derivative thereof, can be administered to an animal in order to induce the production of sera containing polyclonal antibodies that are capable of binding human TPO.

In a preferred method, antibodies according to the present invention are mAbs. Such mAbs can be prepared using hybridoma technology (Kohler et al., *Nature* 256:495 (1975); Kohler et al., *Eur. J. Immunol.* 6:511 (1976); Kohler et al., *Eur. J. Immunol,* 6:292 (1976); Hammerling et al., In: *Monoclonal Antibodies and T-cell Hybridomas*, Elsevier, N.Y., pp. 563–681 (1981)). In general, such procedures involve immunizing an animal with human TPO antigen. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands, J. R., et al. (*Gastroenterology* 80:225–232 (1981). The hybridoma cells obtained through such a selection are then assayed to identify clones which secrete antibodies capable of binding the human TPO antigen.

Antibodies according to the present invention also may be polyclonal, or, preferably, region specific polyclonal antibodies. Region specific polyclonal antibodies and methods of using them are described in co-pending U.S. application Ser. No. 06/731,470, filed 07 May 1985, the specification of which is incorporated herein by reference as though set forth in full.

Antibodies against human TPO according to the present invention are well suited for use in standard immunodiagnostic assays known in the art, including such immunometric or "sandwich" assays as the forward sandwich, reverse sandwich, and simultaneous sandwich assays. The antibodies may be used in any number of combinations as may be determined by those of skill without undue experimentation to effect immunoassays of acceptable specificity, sensitivity, and accuracy for the human TPO antigen or equivalents thereof.

Standard reference works setting forth general principles of immunology include Roitt, I., *Essential Immunology*, Sixth Ed., Blackwell Scientific Publications, Publisher, Oxford (1988); Kimball, J. W., *Introduction to Immunology*, Second Ed., Macmillan Publishing Co., Publisher, New York (1986); Roitt, I., et al., *Immunology*, Gower Medical Publishing Ltd., Publisher, London, (1985); Campbell, A., "Monoclonal Antibody Technology," in, Burdon, R., et al., eds., *Laboratory Techniques in Biochemistry and Molecular Biology*, Volume 13, Elsevier, Publisher, Amsterdam (1984); Klein, J., *Immunology; The Science of Self-Nonself Discrimination*, John Wiley & Sons, Publisher, New York (1982); and Kennett, R., et al., eds., *Monoclonal Antibodies, Hybridoma: A New Dimension in Biological Analyses*, Plenum Press, Publisher, New York (1980).

By "detecting" it is intended to include determining the presence or absence of a substance or quantifying the amount of a substance. The term thus refers to the use of the materials, compositions, and methods of the present invention for qualitative and quantitative determinations The isolation of other hybridomas secreting mAbs of the same specificity as those described herein can be accomplished by the technique of anti-idiotypic screening. Potocmjak, et al., *Science* 215:1637 (1982). Briefly, an anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

By using an anti-Id antibody which is specific for iditoypic determinants on a given mAb, it is then possible to identify other B cell or hybridoma clones sharing that idiotype. Idiotypic identity between the antibody product of two clones makes it highly probable that the antibody products of the two clones recognize the same antigenic epitopes.

The anti-Id antibody may also be used as an "immunogen" to induce an immune response in yet another animal, producing a so-called anti-anti-Id antibody. The anti-anti-Id may be epitopically identical to the original mAb which induced the anti-Id.

Thus, by using antibodies to the idiotypic determinants of a mAb, it is possible to identify other clones expressing antibodies of identical specificity.

Accordingly, mAbs generated against the hTPO antigen may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for the hPTO epitope. The anti-Id mAbs thus have their own idiotypic epitopes, or "idiotopes" structurally similar to the epitope being evaluated.

For replication, the hybridoma cells of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Antibodies according to the present invention are particularly suited for use in immunoassays wherein they may be utilized in liquid phase or bound to a solid phase carrier. In addition, the antibodies in these immunoassays can be detectably labeled in various ways.

There are many different labels and methods of labeling known in the art. Examples of the types of labels which can be used in the present invention include, but are not limited to, enzymes, radioisotopes, fluorescent compounds, chemiluminescent compounds, bioluminescent compounds and metal chelates. Those of ordinary skill in the art will know of other suitable labels for binding to antibodies, or will be able to ascertain the same by the use of routine experimentation. Furthermore, the binding of these labels to antibodies can be accomplished using standard techniques commonly known to those of ordinary skill in the art.

One of the ways in which antibodies according to the present invention can be detectably labeled is by linking the antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label antibodies include malate dehydrogenase, staphylococcal nuclease, delta-V-steroid isomerase, yeast alcohol dehydrogenase, alpha-glycerophosphate dehydrogenase, triose phosphate isomerase, biotin-avidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of detectably labeled antibodies also can be detected by labeling the antibodies with a radioactive isotope which then can be determined by such means as the use of a gamma counter or a scintillation counter. Isotopes which are particularly useful for the purpose of the present invention are $^3$H, $^{125}$I, $^{32}$P, $^{35}$S, $^{14}$C, $^{51}$Cr, $^{36}$Cl, $^{57}$Co, $^{58}$Co, $^{59}$Fe and $^{75}$Se.

It is also possible to detect the binding of detectably labeled antibodies by labeling the antibodies with a fluorescent compound. When a fluorescently labeled antibody is exposed to light of the proper wave length, its presence then can be detected due to the fluorescence of the dye. Among the most commonly used fluorescent labeling compounds are fluorescein, isothiocyanate, rhodamine, phycoerythrin, phycocyanin, allophycocyanin, o-phthaldehyde and fluorescamine.

The antibodies of the invention also can be detectably labeled using fluorescent emitting metals such as $^{152}$Eu, or others of the lanthanide series. These metals can be attached to the antibody molecule using such metal chelating groups as diethylenetriaminepentaacetic acid (OTPA) or ethylenediaminetetraacetic acid (EDTA).

Antibodies also can be detectably labeled by coupling them to a chemiluminescent compound. The presence of the chemiluminescent-tagged antibody is then determined by detecting the presence of luminescence that arises during the course of the chemical reaction. Examples of particularly useful chemiluminescent labeling compounds are luminal, isoluminol, theromatic acridinium ester, imidazole, acridinium salts, oxalate ester , and dioxetane.

Likewise, a bioluminescent compound may be used to label the antibodies according to the present invention. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labeling include luciferin, luciferase and aequorin.

The antibodies and substantially purified antigen of the present invention are ideally suited for the preparation of a kit. Such a kit may comprise a carrier, means being compartmentalized to receive in close confinement therewith one or more container means such as vials, tubes and the like, each of said container means comprising the separate elements of the assay to be used.

The types of assays which can be incorporated in kit form are many, and include, for example, competitive and non-competitive assays. Typical examples of assays which can utilize the antibodies of the invention are radioimmunoassays (RIA), enzyme immunoassays (EIA), enzyme-linked immunosorbent assays (ELISA), and immunometric, or sandwich, immunoassays.

By the term "immunometric assay" or "sandwich immunoassay," it is meant to include simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Forward sandwich assays are described, for example, in U.S. Pat. Nos. 3,867,517; 4,012,296 and 4,376,110. Reverse sandwich assays have been described, for example, in U.S. Pat. Nos. 4,098,876 and 4,316,110.

In the preferred mode for preforming the assays it is important that certain "blockers" be present in the incubation medium (usually added with the labeled soluble antibody). The "blockers" are added to assure that non-specific proteins, protease, or human antibodies to mouse immunoglobulins present in the experimental sample do not cross-link or destroy the antibodies on the solid phase support, or the radiolabeled indicator antibody, to yield false positive or false negative results. The selection of "blockers" therefore adds substantially to the specificity of the assays described in the present invention.

It has been found that a number of nonrelevant (i.e. non-specific) antibodies of the same class or subclass (isotype) as those used in the assays (e.g. $IgG_1$, $IgG_{2a}$, IgM, etc.) can be used as "blockers." The concentration of the "blockers" (normally 1–100 μg/ul) is important, in order to maintain the proper sensitivity yet inhibit any unwanted interference by mutually occurring cross reactive proteins in human serum. In addition, the buffer system containing the "blockers" needs to be optimized. Preferred buffers are those based on weak organic acids, such as imidazole, HEPES, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01–10 μg/ml) to the buffer which contains the "blockers."

There are many solid phase immunoadsorbents which have been employed and which can be used in the present invention. Well known immunoadsorbents include glass, polystyrene, polypropylene, dextran, nylon and other materials, in the form of tubes, beads, and microtiter plates formed from or coated with such materials, and the like. The immobilized antibodies can be either covalently or physically bound to the solid phase immunoadsorbent, by techniques such as covalent bonding via an amide or ester linkage, or by adsorption. Those skilled in the art will know many other suitable solid phase immunoadsorbents and methods for immobilizing antibodies thereon, or will be able to ascertain such, using no more than routine experimentation.

For in vivo, in vitro or in situ diagnosis, labels such as radionuclides may be bound to antibodies according to the present invention either directly or by using an intermediary functional group. An intermediary group which is often used to bind radioisotopes which exist as metallic cations to antibodies is diethylenetriaminepentaacetic acid (DTPA). Typical examples of metallic cations which are bound in this manner are: $^{99m}Tc$, $^{123}I$, $^{111}IN$, $^{131}I$, $^{97}Ru$, $^{67}Cu$, $^{67}Ga$ and $^{68}Ga$. The antibodies of the invention can also be labeled with non-radioactive isotopes for purposes of diagnosis. Elements which are particularly useful in this manner are $^{157}Gd$, $^{55}Mn$, $162Dy$, $^{52}Cr$ and $^{56}Fe$.

The hTPO-encoding DNA sequence of the present invention, or a fragment thereof, may be used as a DNA probe to isolate or detect complementary DNA sequences according to well-known hybridization methods. The human antigen genes may then be cloned and expressed in a host to give the human antigen. This human antigen may then be used in diagnostic assays for the corresponding autoantibody.

The antigen of the invention may be isolated in substantially pure form employing antibodies according to the present invention. Thus, an embodiment of the present invention provides for substantially pure hTPO, characterized in that it is recognized by and binds to the anti-hTPO antibodies of the present invention. In another embodiment, the present invention provides a method of isolating or purifying hTPO by forming a complex with one or are antibodies directed against hTPO.

The substantially pure hTPO of the present invention may in turn be used to detect or measure antibody to hTPO in a sample, such as serum or urine. Thus, one embodiment of the present invention comprises a method of detecting the presence or amount of antibody to hTPO in a sample, comprising contacting the sample containing the antibody to hTPO with detectably labeled hTPO, and detecting the label.

It will be appreciated that immunoreactive fractions and immunoreactive analogs of hTPO also may be used. By the term "immunoreactive fraction" is intended any portion of the hTPO antigen which demonstrates an equivalent recognition by, or binding to, an antibody directed against hTPO. By the term "immunoreactive analog" is intended a protein which differs from hTPO by one or more amino acids, but which demonstrates an equivalent recognition by, or binding to, an anti-hTPO antibody.

T Cells Specific for TPO

Autoimmune diseases are thought to result at least in part due to persistent activation of T cells by self antigens (Janeway, C., Nature 341: 182 (1989)). In the case of autoimmune thyroiditis, as in Hashimoto's thyroidits, such a self antigen can be any epitope of TPO which is recognized by a receptor, on a T cell capable of helping a B cell make an anti-TPO antibody, or a T cell involved in the autoimmune process by any other known mechanism (see below).

One approach to the treatment of autoimmune thyroid diseases as contemplated by the present inventor focuses on disrupting the action of T lymphocytes involved in the disease process. T cells are readily available from the thyroid, for example in Graves' disease in the form of infiltrates extracted from thyroidectomy specimens. By studying such infiltrates, it is possible to examine the antigenic specificities of T cells selected in vivo for their pathogenic relevance.

For example, the infiltrating T cells (as well as T cells present in the circulation and in lymphoid organs such as lymph nodes and spleen) can act as T helper (Th) cells, responding to TPO epitopes, and helping B cells make specific anti-TPO antibodies. Alternatively, or additionally, such T cells can mediate a cell-mediated immune response and act on thyroid epithelial cells either directly or via the local release of cytokines. This may lead to destruction of thyroid epithelial cells, when cytotoxic T cells specific for TPO are activated, or via an inflammatory response mediated by a different T cell class.

Disruption of the activation or action of such T cells would serve to inhibit the production of anti-TPO antibodies, on the one hand, or of thyroid epithelium-damaging T cells on the other.

One embodiment therefore provides peptides capable of binding to the T cell receptor (TCR) of a TPO-specific T cell. Such TPO-related peptides include at least a portion of a T cell epitope of TPO (such as the NP-7 epitope of Example XII). Useful peptides include a sequence of about 5 or more amino acids of TPO, or derivatives of such peptides, which are capable of binding to the TCR of a TPO-specific T cell. Acting as a competitive antagonist for the native autoantigen, such a peptide can inhibit antigen presentation to T cells, or other antigen-specific cell—cell (e.g., T—T or T—B) interactions in the immune system which are needed for generation of either anti-TPO antibodies or TPO-specific cell-mediated immunity. (For discussion of such peptide-based approaches to immnotherapy of autoimmune disease, see, for example: Acha-Orbea, H., et al. (*Ann Rev. Immunol.* 7:371–405 (1989); Kumar, V., et al., *Ann. Rev. Immunol.* 7:657–682 (1989); Urban, J. L. et al., *Cell* 54:577–592 (1989); Wraith, D. C., et al. (*Cell* 57:709–715 (1989); Wraith. D. C., et al., *Cell* 59:247–255 (1989); Urban. J. L., et al., *Cell* 59:257–271 (1989); and Janeway, C. A., *Nature* 341:482–483 (1989), all of which references are hereby incorporated by reference).

Another embodiment of the invention provides for a pharmaceutical preparation comprising the above peptides. In yet another embodiment of the invention, a method of treating autoimmune disease, including but not limited to Hashimoto's thyroiditis, is provided which comprises administering to a patient suffering from such disease a pharmaceutical preparation comprising a TPO-related peptide.

An alternate peptide-based therapeutic strategy contemplated within the scope of the present invention is directed to vaccines comprising TPO-specific T cells (Cohen, I. R., *Immunol. Rev.* 94:5–21 (1986); *Prog, Immunol*, VI;491–499 (1986) ; *Scientific Amer.* 258:52–60 (1988); *Hosp. Prac*, pp. 57–64 (Feb. 15, 1989); Cohen, I. R., et al., *Immunol. Today* 9:332–335 (1988)) and peptides mimicking the TCR of such TPO-specific T cells (Vandenbark, A. A. et al., *Nature* 341:541–544 (1989); Howell. N. D. et al., *Science* 246:668–671 (1989)). Such preparations are administered to an individual to prevent or suppress an autoimmune response to TPO by inducing a state of "counter-autoimmunity." Such counter-autoimmunity is thought to be mediated by T cells which are specific to the TCR of the autoimmune (i.e., TPO-specific) T cell (Cohen, supra, Vandenbark et al., supra, and Sun, D. et al., *Nature* 332:843–845 (1988); *Europ. J. Immunol.* 18:1993–1999 (1988)).

The invention is therefore directed to T cells specific for TPO capable of acting as a "vaccine" and inducing a state of counter-autoimmunity. Another embodiment includes TCR mimicking peptides of such T cells. Yet another embodiment is directed to the T cells induced by such TPO-specific T cell and TCR peptide vaccines which mediate the counter-autoimmune effects or down-regulate TPO-specific T cells. Another embodiment of the invention provides for a pharmaceutical preparation comprising such a T cell vaccine, TCR peptide, or counter-autoimmune T cell. In yet another embodiment of the current invention, a method of treating autoimmune disease, such as Hashimoto's thyroiditis, is provided which includes the use of a pharmaceutical preparation comprising either a TPO-specific T cell vaccine, a TCR peptide vaccine, or a counter-autoimmune T cell specific for TPO-specific T cells.

An additional embodiment of the present invention is directed to a T suppressor (Ts) lymphocyte capable of interacting specifically with an anti-TPO B cell or T cell, leading to suppression of an anti-TPO immune response. Such suppression could be of TPO-specific antibody production or of TPO-specific T cell-mediated thyroid damage such as that mediated by cytotoxic T cells or in a TPO-specific delayed hypersensitivity response. Thus in one embodiment, the invention is directed to an epitope of TPO capable of inducing antigen-specific Ts cells and its use in generating Ts cells and in treating autoimmune thyroiditis. Another embodiment is a TPO-specific Ts in a pharmaceutical preparation. Yet another embodiment is directed to a method of treating autoimmune thyroiditis, such as Hashimoto's disease, comprising administering a pharmaceutical preparation comprising a TPO epitope capable of inducing Ts cells. An additional embodiment is a method of treating autoimmune thyroiditis by administering a pharmaceutical preparation comprising TPO-specific Ts cells capable of suppressing an anti-TPO response. For a discussion of suppressor cells, see, for example, Green, D., et al., *Ann. Rev. Immunol.* 1: 439 (1983) and Benacerraf, B., In: *The Biology of Immunologic Disease*, HP Publishing Co., Inc., N.Y., pp. 49–62 (1983).

The present invention allows the determination of the T cell epitope or epitopes of TPO (see Example XII, below) using standard techniques commonly known to those of ordinary skill in the art. Further, the present invention makes possible the characterization of the autoimmune TCR specific to the TPO using methods described in, for example, Burns, F., et al., *J. Exp, Med.* 169: 27 (1989). If the autoimmune T cells can be eliminated or prevented from reacting with the TPO, the effects of thyroiditis may be greatly alleviated. T cells that will accomplish this objective may be generated which are specific for the autoimmune TCR for TPO using methods described in, for example, Acha-Orbea, H., et al., *Ann. Rev. Immunol.* 7: 371 (1989).

The manner and method of carrying out the present invention may be more fully understood by those of skill by reference to the following examples, which examples are not intended in any manner to limit the scope of the present invention or of the claims directed thereto.

EXAMPLE I

Construction of a Human Graves' Thyroid cDNA Library

A thyroid cDNA library was constructed to maximize the inclusion of full-length cDNA in the coding orientation. Hyperplastic thyroid tissue was obtained from a patient undergoing thyroidectomy for Graves' disease. mRNA was isolated according to the method of Han et al. (Han, J. H., et al., Biochem. 26:1617–1625 (1981)). Double-stranded cDNA was synthesized from 15 µg mRNA as described by Gubler and Hoffman (Gubler, U., et al., Gene 2:263–269 (1983)). Not I and Xba I linker-primers/adaptors were incorporated into the cDNA to create those restriction sites at the 5' and 3' ends, respectively, of the cDNA (Han, J. H., et al., Biochem. 26:1611–1625 (1987)). The cDNA was size-selected (>1 kb) by agarose gel (Seaplaque, FMC, Rockland, Me.) electrophoresis, digested with Not I and Xba I, ligated into Not I- and Xba I-cut bacteriophage lambda-Zap using T4 DNA ligase, and packaged (Gaga-Pak Gold, Stratagene, San Diego, Calif.). The resulting phage library contained a total of $2 \times 10^4$ recombinant clones before amplification.

EXAMPLE II

Screening for Full-length Human TPO cDNA

The amplified cDNA library was plated at a density of $4 \times 10^4$ pfu per 150 mm diameter dish and probed using the insert from a partial human TPO cDNA clone (clone 19). Two positive bacteriophage clones were isolated. A Bluescript phagemid containing the human TPO cDNA insert was generated from one of these clones using the helper phage R408, according to the Stratagene protocol. The resulting recombinant Bluescript plasmid (pHTPO-BS) contained bases 5–3060 of human thyroid peroxidase cDNA, including the start of translation and the poly-A tail. DNA sequence was determined from this double-stranded plasmid using the Sequenase kit and protocol (United States Biochemical, Cleveland, Ohio). Sequence within the cDNA was confirmed to be identical to human TPO cDNA at the 5' and 3' ends and in the regions adjacent to 10 oligonucleotide primers distributed throughout the cDNA (Magnusson, R. P., et al., Mol. Endocrinol, 1:856–861 (1987)).

EXAMPLE III

Construction of pHTPO-ECE

Figure 1:
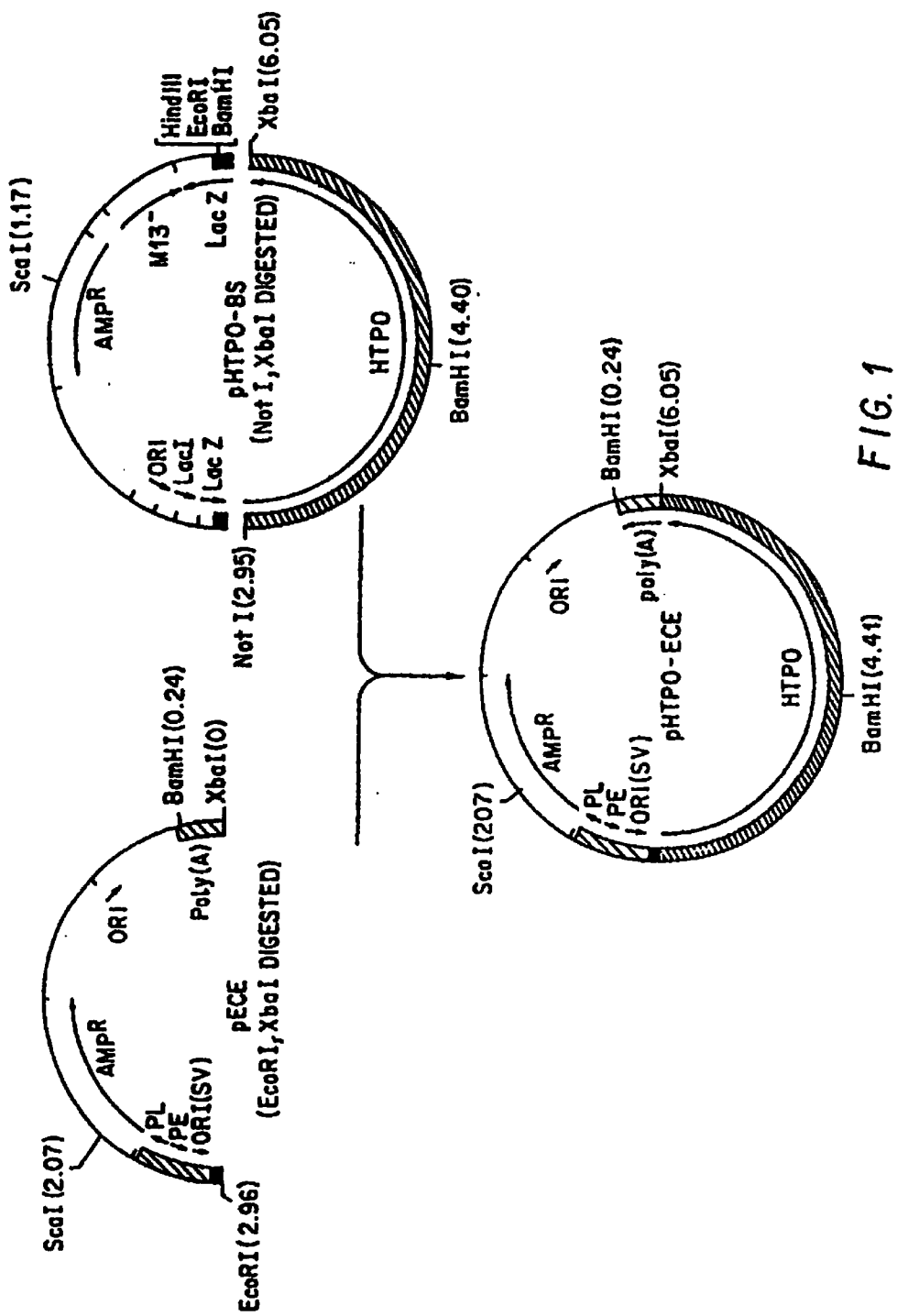
FIG. 1. Construction of the expression plasmid pHTPO-ECE. pHTPO-BS (upper right) was digested with Not I, the ends blunted with the Klenow fragment of DNA polymerase I, and the DNA subsequently digested with Xba I. The released Bluescript vector was further digested with Sca I to obtain good separation on agarose gel electrophoresis because of the similar size of this vector (2.95 kb) and the HTPO cDNA fragment (3.1 kb). The mammalian expression vector pECE (Ellis, L., et al., *Cell* 45:721–732 (1986)) is (upper left) was digested with Eeo RI, the ends blunted with the Klenow fragment of DNA polymerase I, and the DNA subsequently digested with Xba I. The digested pHTPO-BS and pECE fragments were then ligated using T4 DNA ligase (Marliatis, T., et al., *Molecular Biology: A Laboratory Manual*, Cold Spring Harbor Laboratory, Cold Spring Harbor, N.Y. (1982)). The resulting plasmid, pHTPO-ECE (bottom), was transfected into competent XL1-Blue cells (Stratagene, San Diego, Calif.). Narrow hatching: HTPO; wide hatching: SV40; black: Multiple Cloning Sites.
Figure 2A:
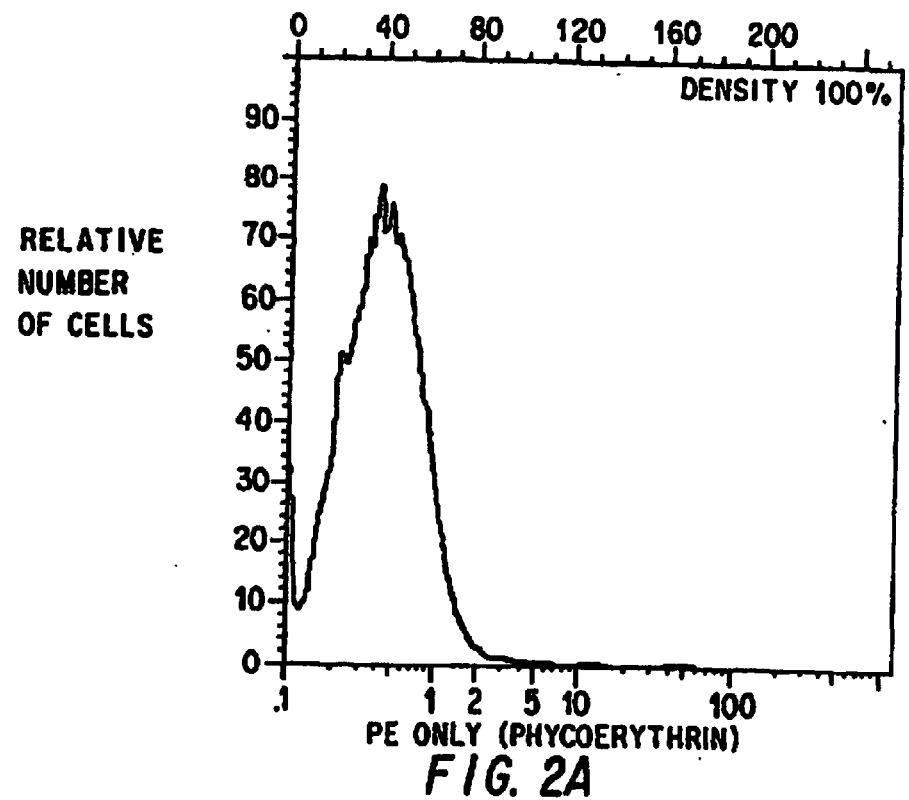
FIG. 2. Fluorescence-activated cell sorter (FACS) analysis of CHO cells transfected with pHTPO-ECE. CHO-HTPO12b cells were processed as described herein.
Figure 2B:
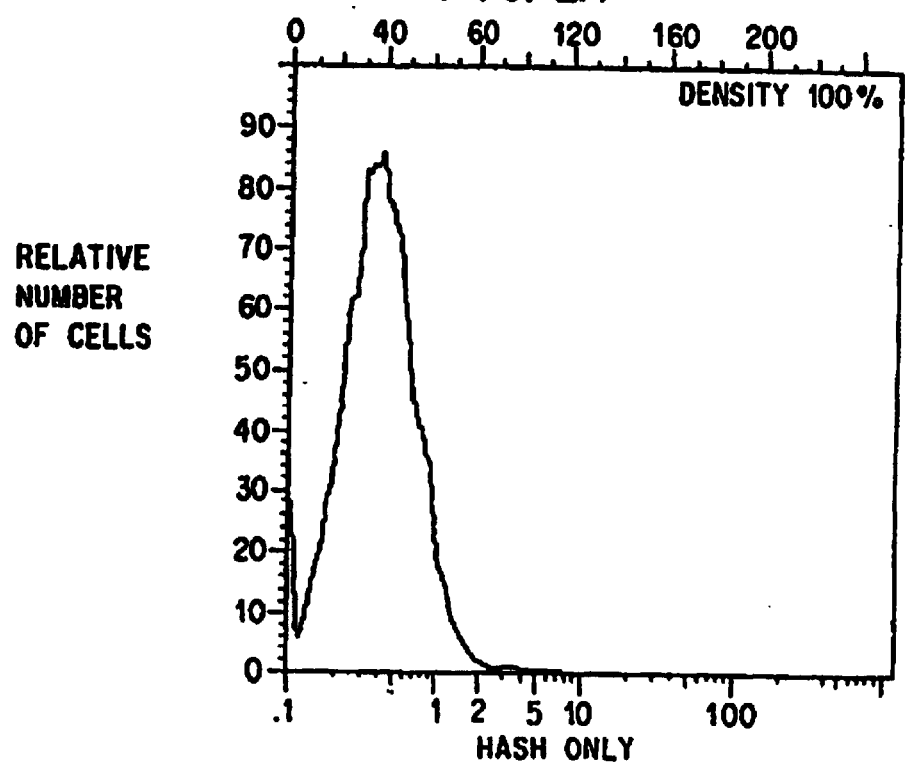
Figure 2C:
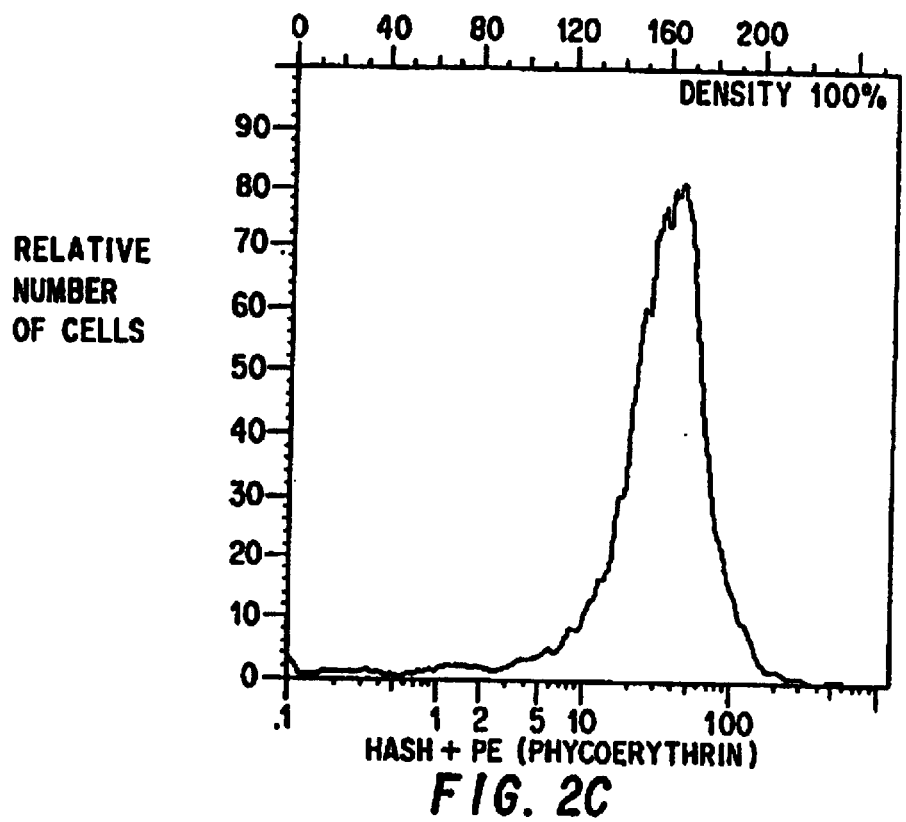
Figure 2D:
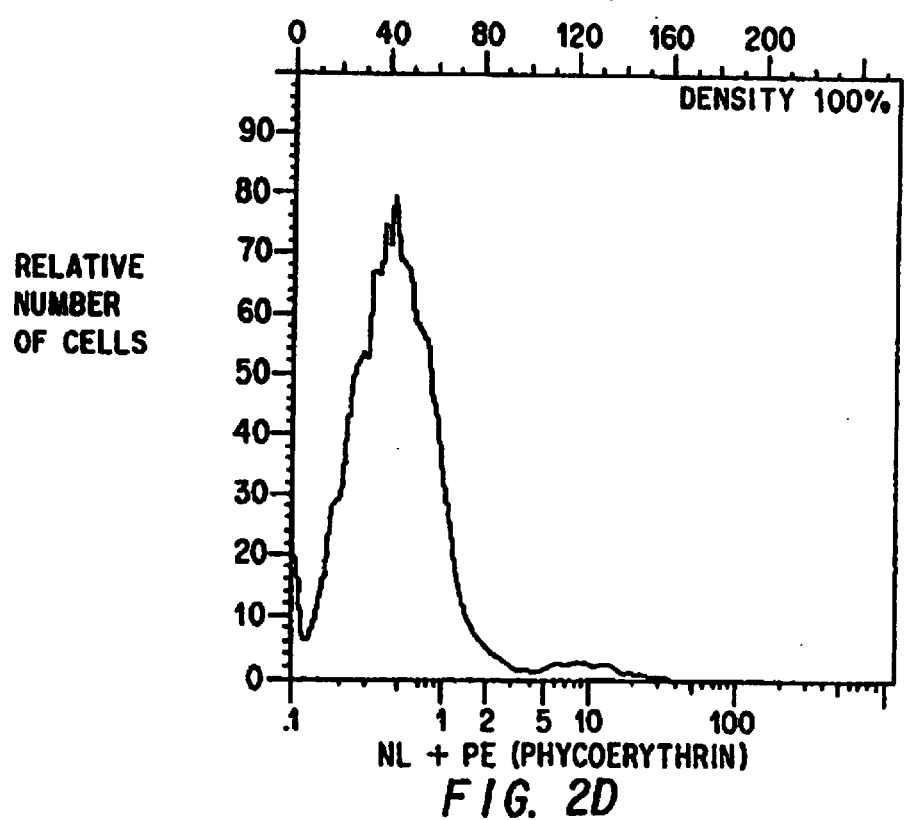
Figure 2E:
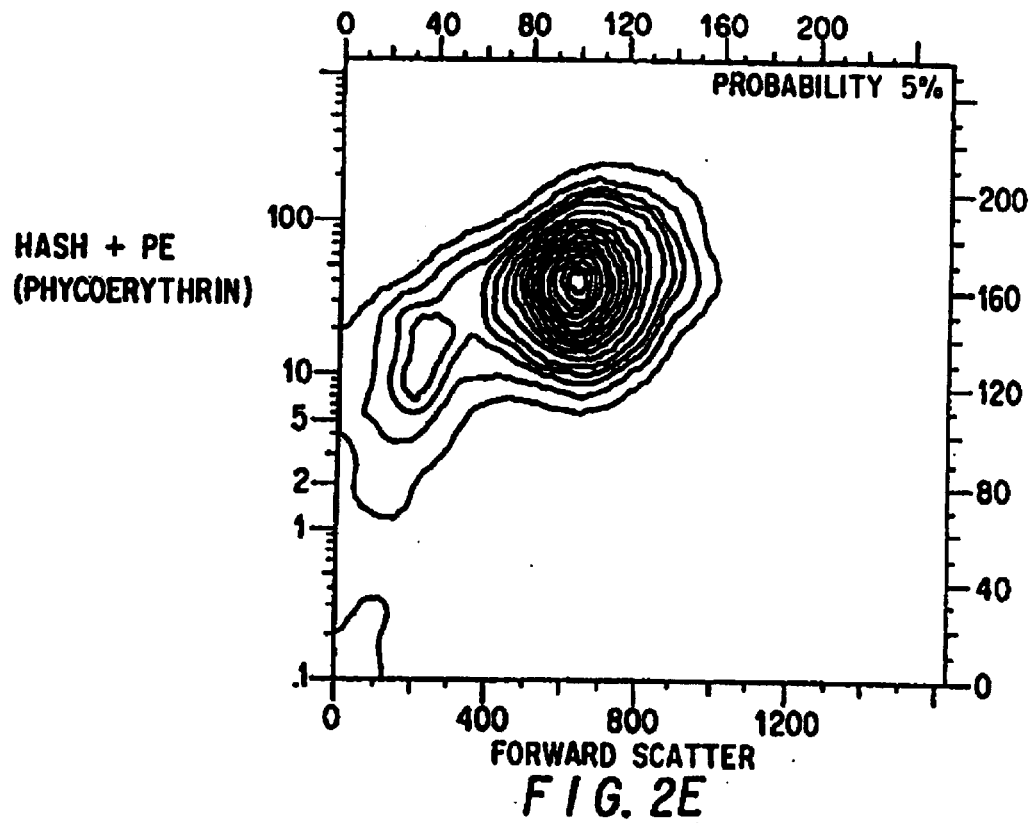
Figure 2F:
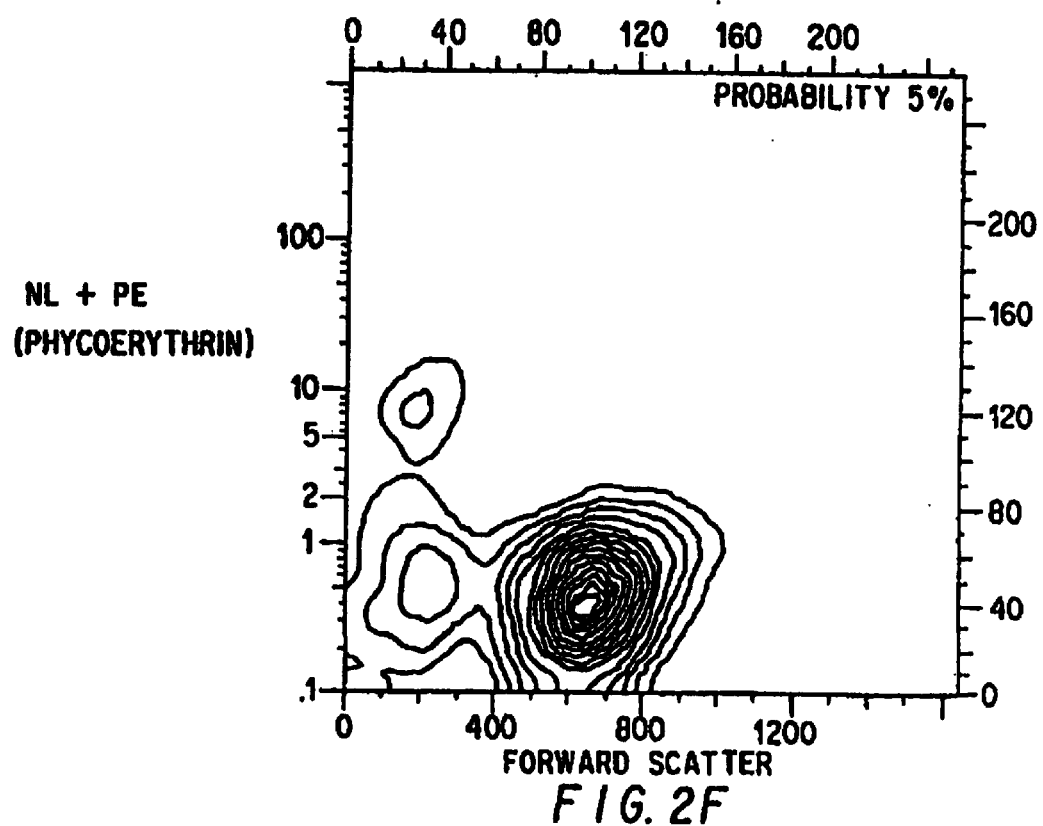

The mammalian cell expression vector pECE (Ellis, L., et al., Cell 45:121–732 (1986)) was obtained from Dr. William Rutter (U.C.S.F.). Human TPO cDNA was cloned into the multiple cloning site of this vector as described in FIG. 1. Enzyme reactions and DNA manipulations were performed as described in Maniatis et al. (Maniatis, T., et al., Molecular Biology: A Laboratory Manual, Cold Spring Harbor Laboratory, Cold Spring Harbor, N.Y. (1982)).

EXAMPLE IV

Transfection of Chinese Hamster Ovary Cells with pHTPO-ECE

Chinese hamster ovary cell line CHO-K1 was maintained in Hams' F-12 medium supplemented with 10% fetal bovine serum, penicillin (125 units/ml), streptomycin (100 µg/ml) and amphotericin-B (2.5 µg/ml). Transfection and selection with G-418 (GIBCO, Grand Island, N.Y.) was carried out by the method of Chen and Okayama (Chen, C., et al., Mol. Cell. Biol7:2745–2152 (1987)). 20 µg pHTPO-ECE plus 2 µg pSV2-neo (28) (from Dr. John Baxter, U.C.S.F.) were used for the transfection. Control transfections with 20 µg pECE plus 2 µg pSV2-neo, and 20 µg pSV2-neo alone, were performed concurrently.

EXAMPLE V

RNA Extraction and Northern Blot Analysis

Total cellular RNA was extracted by the method of Chomczynski and Sacchi (Chomczynski. P., et al., Anal. Biochem. 162:156–159 (1981)). 15 µg of RNA was electrophoresed in formaldehyde gels as described by Maniatis et al. (Maniatis, T., et al., Molecular Biology: A Laboratory Manual, Cold Spring Harbor Laboratory, Cold Spring Harbor, N.Y. (1982)). RNA was blotted onto a Zeta-Probe membrane (BioRad, Richmond, Calif.) and probed with a 0.56 kb human TPO cDNA probe (clone 31 insert), labeled to a specific activity of $4 \times 10^9$ cpm/µg DNA using the Multi-Prime labeling kit from Amersham (Arlington Heights, Ill.).

EXAMPLE VI

Western Blot Analysis

Transfected CHO cells were extracted to obtain soluble protein. Five 100 mm diameter dishes were washed 3 times with calcium-magnesium free phosphate-buffered saline (PBS). After aspiration, 5 ml of 0.5% Triton X-100 in the same buffer, supplemented with 10 µg/ml leupeptin, 0.5 mg/ml bacitracin and 2 mM phenylmethylsulfonyl fluoride (all from Sigma, St. Louis, Mo.), were added to the first dish. This initial cell solution was scraped and transferred successively to the other 4 dishes of cells. The cell solution was then tumbled for 1 hour at 4° C. After centrifugation for 3 minutes at 10,000×g, the supernatant was saved and stored at −20° C. until use. Protein content was determined (Bradford, N. M., Anal. Biochem. 72:248–254 (1976)) and 50 µg protein/lane electrophoresed on a 7.5% polyacrylamide SDS gel (Laemmli, U.K., Nature 227:680–689 (1970)). Proteins were electrotransferred (30 V×5 hours, or 250 mA overnight) to nitrocellulose membranes (Schleicher and Schuell, Keene, N.H.) in an electroblotting apparatus (Hoeffer, San Francisco, Calif.) containing 25 mM Tris, 192 mM glycine, 20% methanol. In later experiments, transfer was accomplished using a Polyblot semi-dry electrotransfer system (American Bionetic, Hayward, Calif.), according to the directions of the manufacturer. Membranes were rinsed once in TBS (0.1 N Tris, pH 8.0, 0.15 M NaCl), then for 30–60 minutes at room temperature in TBS containing 0.5% Tween 20 (Sigma, St. Louis, Mo.). After 3 further rinses with TBS-Tween, the blots were probed as described by Young and Davis (Young, R. A., et al., In Genetic Engineering: Principals and Methods, Plenum Publishing Corp., 7:29–41 (1985)) using a 1:250 dilution of a mouse mAb against the thyroid microsomal antigen (Portmann, L., et al., J. Clin. Invest. 81:1217–1224 (11988)), followed by a 1:250 dilution of horseradish peroxidase-conjugated goat anti-mouse IgG antibody (Sigma, St. Louis, Mo.).

In other experiments, CHO-HTPO12b cell extracts were probed using a panel of polyclonal Hashimoto's thyroiditis sera, provided by Dr. S. M. McLachlan, University of Wales, Cardiff. Antimicrosomal antibody titers had previously been determined by enzyme-linked immunosorbant assay (ELISA) in the presence of excess thyroglobulin (Jansson, R., et al., *Clin. Exp. Immunol.* 63:80–86 (1986)). Multiple Hashimoto's thyroiditis sera were applied to a single filter overnight at 4° C. using a Miniblotter 45 manifold (Immunetics, Cambridge, Mass.). Membranes were then processed as described above, except that alkaline phosphatase-conjugated goat anti-human IgG, Fc fragment specific (Cappel, Organon Teknika Corp., West Chester, Pa.) was used as the second antibody with nitroblue tetrazolium (0.3 mg/ml) and 5-bromo-4-chloro-3-indolyphosphate (0.15 mg/ml) in 100 mM Tris, pH 9.5, 100 mM NaCl, 5 mM $MgCl_2$.

EXAMPLE VII

Fluorescence-activated Cell Sorter (FACS) Analysis

CHO-HTPO12b cells were processed as described by Ellis et al. (Ellis, L., et al., *Cell* 45:721–732 (1986)). In brief, cells from a 100 mm diameter dish were detached by mild trypsinization, and the cells rinsed and pelleted (5 minutes at 100×g, 4° C.) in Ham's F12 medium, 10% fetal calf serum (see above). The cells were resuspended in 0.2 ml of phosphate-buffered saline (PBS), 10 mM Hepes, pH 7.4, 0.05% Na azide (buffer A). Serum to be tested (2 ul) was added for 30 minutes at 4° C., followed by two rinses in buffer A with 2% fetal calf serum and resuspension in 0.2 ml of the same solution. 25 ul of goat anti-human IgG, Fc specific, affinity-purified, R-Phycoerythrin-labeled (Caltag, South San Francisco, Calif.) were added for another 30 minutes at 4° C. After 3 washes in buffer A, the cells were analyzed on a fluorescence-activated cell sorter.

EXAMPLE VIII

Assay of Human TPO Enzymatic Activity

Human TPO activity was assayed following extraction from cell microsomes with trypsin- and deoxycholate as previously described (Magnusson, R. P., et al., *Endocrinol.* 116:1493–1500 (1985)). In later experiments, a more rapid method was used. Cells were suspended with a rubber scraper in 1.5 ml calcium-magnesium free Dulbecco's phosphate-buffered saline and protein determined on a 5 ul aliquot. The cells were then pelleted in a microcentrifuge for 2 minutes. Cold 0.1% deoxycholate (0.2 ml/mg cellular protein) was added for 10 minutes. The extract was microcentrifuged for 5 minutes and the supernatant removed for assay. One guaiacol unit is defined as a __A470 of 1.0 per minute which is equivalent to 150 nmols guaiacol oxidized per minute (Chance, B., et al., In *Methods in Enzymology* (Colonic. S. P., et al.), Academic Press, New York 2:164–115 (1955)). One unit of iodide peroxidase is defined as a __A353 of 1.0 per minute which corresponds to 43 nmols I3-formed per minute (Magnusson, R. P., et al., *J. Biol. Chem.* 259:13783–13790 (1984)).

EXAMPLE IX

Primary Culture of Human Graves' Disease Thyroid Cells

Human Graves' disease thyroid tissue was dispersed and the cells cultured as previously described (Binds, W. E., et al., *J. Clin. Endocrinol. Metab.* 52:1204–1210 (1981)). After 3 days in culture, fresh medium containing 123 mU/ml TSH was added for an additional 3 days before the cells were harvested and extracted as described above for the western blots.

EXAMPLE X

Comparison of Recombinant hTPO and Microsomal Antigen as Sources of Antigen for ELISAs for Anti-MSA/Anti-TPO Antibodies Sera from 51 individuals were provided by Dr. S. M. McLachlan (University of Wales College of Medicine, Cardiff, U.K.). Forty seven of these sera were from patients with autoimmune thyroid disease, selected to represent a balanced spectrum of anti-MSA titers from low to very high. Four sera were from normal individuals. Anti-MSA and anti-TGA antibodies were measured by the method of Schardt et al. (Schardt, C. W., et al., *J. Immunol. Methods* 55:155–168 (1982)) and the method of Endo et al. (Endo, Y., *Clin. Chim. Acta* 103:67–77 (1980)), as modified by McLachlan et al. (McLachlan, S. M., et al., *Immunol. Letters* 4–27–33 (1982)), respectively. For the anti-MSA assay, human thyroid microsomes were prepared from frozen Graves' thyroid tissue obtained at operation for the treatment of this disease (Schardt, C. W., et al., *J. Immunol. Methods* 55155–168 (1982)). In order to avoid cross-reactivity of patients' sera with any thyroglobulin remaining in the microsomal preparation, sera were pre-adsorbed in buffer containing 100 μg/ml ($1.5–10^{-6}$ M) thyroglobulin (obtained from the same tissue) at 4° C. overnight and thereafter at room temperature for 2 hours before assay (Schardt, C. W., et al., *J. Immunol. Methods* 55:155–168 (1982)).

The generation of Chinese hamster ovary (CHO) cells (clone CHO-HTPO12b) expressing enzymatically-active human TPO has been described above. These cells had been transfected with the recombinant plasmid pHTPO-ECE, constructed by the insertion of a full-length human TPO cDNA into the expression vector pECE. CHO-HTPO12b and CHO-K1 (control, non-transfected) cells were grown in Ham's F-12 medium supplemented with 100 g/L fetal bovine serum (FBS), penicillin (125 units/ml), gentamicin (48 μg/el) and amphotericin-B (2.5 μg/ml). Cells were grown to confluence in 100 mm dishes, the cells were rinsed three times with Dulbecco's calcium-magnesium free, phosphate-buffered saline (PBS), and then scraped into a solution containing 10 mM Tris, pH 7.4, 0.25 M sucrose, 2 mM phenylmethyl sulfonyl fluoride, 10 μg/ml leupeptin, 0.5 mg/ml bacitracin (Buffer A). Cells were homogenized for 20 seconds with a Polytron, centrifuged for 15 minutes at 10,000×g, 4° C., and the supernatant then centrifuged for 1 hour at 100,000×g, 4° C. The microsomal pellet was resuspended in 0.5 ml of Buffer A, homogenized in a Bounce homogenizer, and then frozen at −80° C. until use. Protein content was determined by the method of Bradford (Bradford, M. M., *Anal. Biochem.* 72:248–254 (1976)). Yield of microsomal protein was approximately 100–200 μg per 100 mm dish of confluent cells.

Sera to be tested were stored in aliquots at −80° C. before use. The assay procedure was that of Schardt et al. (Schardt, C. W., et al., *J. Immunol. Methods* 55:155–168 (1982)), with slight modifications. Multiwell micro-ELISA ;plates (Dynatech Labs, Chantilly, Va.) were coated (overnight at 4° C.) with 4 μg CHO-HTPO12b or CHO-K1 microsomal protein per well in coating buffer (0.05 M sodium bicarbonate, pH 9.3, 0.02% sodium azide). The wells were then rinsed twice in 0.2 N Tris, pH 7.4, 0.15 M NaCl (Tris buffer), once in 0.2 N Tris, pH 7.4, 0.15 N NaCl, 0.05% Tween 20 (Tris-Tween buffer), and once in Tris buffer. 100 ul of PBS, 50 g/L bovine serum albumin (BSA) (Sigma, St. Louis, Mo.) were added to each well and incubated for 20 minutes at room temperature. After aspiration, the wells were washed twice in Tris buffer, once in Tris-Tween buffer, and once in Tris buffer.

Serum samples were diluted 1/100, 1/1000 or 1/10,000 in PBS, 5 g/L BSA. 100 ul of the diluted serum sample were added per well in duplicate and incubated for 1 hour at 31° C. The wells were then washed three times with PBS. 100 ul of peroxidase-conjugated, affinity-purified, goat anti-human IgG, Fc fragment specific antibody (Cappel, Organon Teknika Corp., West Chester, Pa.), diluted 1/500 in PBS, 250 g/L FBS, were added to each well and incubated for 1 hour at 37° C. The wells were then washed four times with Tris-Tween buffer. 100 ul of substrate solution (12 ml of 0.23 M citrate, 0.26 M sodium phosphate, pH 5.0 solution+12 uL 30% $H_2O_2$+4.2 mg ortho-phenylenediamine) were added to each well and incubated for 30 minutes at room temperature. The reaction was stopped by adding 100 ul of 20% sulfuric acid to each well. ELISA values (OD 490 nm) were measured in a micro-ELISA reader and normalized (blanked) to a well lacking antigen.

EXAMPLE XI

Oligonucleotide-Directed Mutagenesis of Human TPO cDNA

A. METHODS

The non-coding strand of human TPO cDNA, in the phagemid Bluescript (Stratagene, San Diego, Calif.), was used as a template for oligonucleotide-directed mutagenesis. A 52 bp mutagenic primer (5'-AGGCTCCCTCGG GTGACTTGAATTCCCATGTAGCTGGCTGCTCTGC TGATCG-3'), (SEQ ID NO: 8) synthesized by the molecular Genetics Core Facility, San Francisco Veterans' Administration Medical Center, was designed to generate two stop codons directly upstream of the putative membrane-spanning region of the protein. Thus, TGA and TAG codons were created at 2629–2631 bp and 2641–2643 bp in human TPO cDNA (Magnusson, R. P., et al., Mol. Endocrinol. 1:856–861 (1987)), respectively. The cDNA sequence of human TPO as published on page 857 as FIG. 2 in Magnusson, R. P., et al., Mol. Endocrinol. 1:856–861 (1987) is as follows:

gaggcaattgaggcgcccatttcagaa-
gagttacagccgzgaaaattactcagcagtgca 60
gttggctgagaagaggaaaaaagaat-
gagagcgctggctgtgctgtctgtcacgctggtt 120
atggcctgcacagaagccttcttcccct-
tcatctcgagagggaaagaactcctttgggga 180
aagcctgaggagtctcgt-
gtctctagcgtcttggaggaaagcaagcgcctggtggacacc 240
gccatgtacgccacgatgcagagaaac-
ctcaagaaaagaggaatcctttctggagctcag 300
cttctgtctttttccaaacttcctgagc-
caacaagcggagtgattgcccgagcagcagag 360
ataatggaaacatcaatacaagcgat-
gaaaagaaaagtcaacctgaaaactcaacaatca 420
cagcatccaacggatgctttatcagaa-
gatctgctgagcatcattgcaaacatgtctgga 480
tgtctcccttacatgctgccccaaaat-
gcccaaacacttgcctggcgaacaaatacagg 540
cccatcacaggagcttgcaacaaca-
gagaccaccccagatggggcgcctccaacacggcc 600
ctggcacgatggctccctccagtctat-
gaggacggcttcagtcagccccgaggctggaac 660
cccggcttcttgtacaacgggttc-
ccactgccccggtcgggaggtgacaagacatgtc 720
attcaagtttcaaatgaggttgtcaca-
gatgatgaccgctattctgacctcctgatggca 780
tggggacaatacatcgaccacga-
catcgcgttcacaccacagagcaccagcaaagctgcc 840
ttcggggagggtctgactgccagat-
gacttgtgagaaccaaaaccatgttttcccata 900
caactcccggaggaggcccggccggc-
cgcgggcaccgcctgtctgcccttctaccgctct 960
tcggccgcctgcggcaccggggaccaag-
gcgcgctctttgggaacctgtccacggccaac 1020
ccgaggcagcagatgaacgggttgac-
ctcgttcctggacgcgtccaccgtgtatggcagc 1080
tccccggccctagagaggcagctgcg-
gaactgaccagtgccgaagggctgctccgcgtc 1140
cacggccgcctccgggactccggc-
cgcgcctacctgcccttcgtgccgccacgcgcgcct 1200
gcggcctgtgcgccccgagcccggcaac-
cccggagagaccccgcgggcccctccttcctggcc 1260
ggagacggccgcgccagcgaggtc-
ccctccctgacggcactgcacacgctgtggctgcgc 1320
gagcacaaccgcctggccgcggcgct-
caaggccctcaatgcgcactggaccgcggacgcc 1380
gtgtaccaggaggcgcgcaag-
gtcgtgggcgctctgcaccagatcatcaccctgagggat 1440
tacatccccaggatcctgggacccgag-
gccttccagcagtacgtgggtccctatgaaggc 1500
tatgactccaccgccaaccccactgt-
gtccaacgtgttctccacagccgccttccgcttc 1560
ggccatgccacgatccacccgctggt-
gaggaggctggacgccagcttccaggagcacccc 1620
gacctgcccgggctgtggctgcaccag-
gctttcttcagcccatggacattactccgtgga 1680
ggtggtttggacccactaatacgaggc-
cttcttgcaagaccagccaaactgcaggtgcag 1740
gatcagctgatgaacgaggagctgacg-
gaaaggctcttttgtgctgtccaattccagcagt 1800
ttggatctggcgtccatcaacctgca-
gaggggccgggaccacgggctgccaggttacaat 1860
gagtggagggagttctgcggcctgc-
ctcgcctggagaccccgctgacctgagcacagcc 1920
atcgccagcaggagcgtggccgacaa-
gatcctggacttgtacaagcatcctgacaacatc 1980
gatgtctggctgggaggcttagct-
gaaaacttcctccccagggctcggacagggccctg 2040
tttgcctgtctcattgggaagcagat-
gaaggctctgcgggacggtgactggttttggtgg 2100
gagaacagccacgtcttcacggatgca-
cagaggcgtgagctggagaagcactccctgtct 2160
cgggtcatctgtgacaacactggcct-
caccaggggtgcccatggatgccttccaagtcggc 2220
aaattccccgaagactttgagtcttgt-
gacagcatcactggcatgaacctggaggcctgg 2280
agggaaacctttcctcaagacgacaagt-
gtggcttcccagagagcgtggagaatggggac 2340
tttgtgcactgtgaggagtctgggag-
gcgcgtgctggtgtattcctgccggcacgggtat 2400
gagctccaaggccgggagcagctcact-
tgcacccaggaaggatgggatttccagcctccc 2460
ctctgcaaagatgtgaacgagtgtgca-
gacggtgcccaccccccctgccacgcctctgcg 2520
aggtgcagaaacaccaaggcggcttc-
cagtgtctctgcgcggaccccctacgagttagga 2580
gacgatgggagaacctgcgtagactc-
cgggaggctccctcgggtgacttggatctccatg 2640
tcgctggctgctctgctgatcggaggct-
tcgcaggtctcacctcgacggtgatttgcagg 2700
tggacacgcactggcactaaatcca-
cactgcccatctcggagacaggcggaggaactccc 2760
gagctgagatgcggaaagcaccaggccg-
tagggacctcaccgcagcgggccgcagctcag 2820
gactcggagcaggagagtgctgggatg-
gaaggccgggatactcacaggctgccgagagcc 2880
ctctgagggcaaagtggcaggacactg-
cagaacagcttcatgttcccaaaatcaccgtac 2940
gactcttttccaaacacaggcaaatcg-
gaaatcagcaggacgactgttttcccaacacgg 3000
gtaaatctagtaccatgtcgtagt-
tactctcaggcatggatgaataaatattatagctgc 3060
aaaaaaaaaaaa 3072 (SEQ ID NO:2).

For convenient screening of mutants, an Eco RI restriction site (GAATTC, at 2630–2635 bp) was created together with the first (TGA) stop codon. The mutagenesis procedure was performed according to the protocol of the manufacturer (Muta-gene phagemid in vitro mutagenesis kit, Biorad, Richmond, Calif.) to generate the plasmid pHTPO(M1)-BS.

After confirmation of the mutation by nucleotide sequencing (Sanger, F., et al., *Proc. Natl. Acad. Sci. USA* 74:5463–5467 (1977)) (FIG. 13), the cDNA was excised by digestion of pHTPO(M1)-BS with Not I, the ends blunted with the Klenow fragment of DNA Polymerase I, and the cDNA liberated by digestion with Xba I. The mutated cDNA (3.05 Kb) was substituted for wild-type human TPO cDNA in the plasmid pSV2-DHFR-ECE-HTPO, to generate pHTPO(M1)-ECE-SV2-DHFR. This plasmid contains components of the expression vectors pECE (Ellis, L., et al., *Cell* 45:721–732 (1986)) and pSV2-dhfr (Lee, F., et al., *Nature* 294:228–232 (1981)), provided by Dr. William Rutter (University of California, San Francisco) and Dr. Gordon Ringold (Syntex, Palo Alto), respectively. In brief, pSV2-DHFR-ECE-HTPO was digested with Sal I, the ends blunted with the Klenow fragment of DNA polymerase I, and the hTPO cDNA released by digestion with Xba I. The remaining vector (pSV2-DHFR-ECE) was treated with bacterial alkaline phosphatase, gel purified, and recovered in SeaPlaque agarose (FMC BioProducts, Rockland Me.). Mutated hTPO cDNA also recovered in SeaPlaque agarose, was ligated into this vector, *Enzymes*, Restriction enzymes, T4 DNA ligase and DNA polymerase I, Klenow fragment were obtained alternatively from Bethesda Research Laboratories (Gaithersburg, Md.), New England Biolabs (Beverly, Mass.) or Boehringer-Mannheim (Indianapolis, Ind.).

B. RESULTS AND DISCUSSION

Because multiple screenings of previously constructed human thyroid cDNA library in lambda gt11 (Magnusson, R. P., et al., *Mol. Endocrinol.* 1:856–861 (1981)) only yielded fragments of TPO cDNA, a new thyroid cDNA library in lambda-Zap was constructed as described herein. The plasmid pHTPO-BS containing full-length human TPO cDNA was obtained from this library. pHTPO-ECE was constructed from pHTPO-BS and the mammalian expression vector pECE (Ellis, L., et al., *Cell* 45:721–732 (1986)) according to the strategy shown in FIG. 1, and was used for subsequent cell transfections.

Chinese hamster ovary cells were co-transfected with pHTPO-ECE and pSV2-neo, and 12 clones were tested for the presence of TPO mRNA by northern blot analysis. Total cellular RNA (15 µg/lane) from four pHTPO-IECE transfected cell lines (CHO-HTPO4, CHO-HTPO12, CHO-HTPO14 and CHO-HTPO17), and one control pSV2-neo-transfected cell line (CHO-pSV2-neo), was subjected to northern blot analysis using a human TPO cDNA probe, as described herein. For comparison, 1 µg of poly A+ mRNA prepared from a human thyroid gland from a patient with Graves' disease was used. 28S and 18S ribosomal RNA markers, and an RNA molecular weight ladder (B.R.L., Gaithersburg, Md.) were employed for molecular weight determination.

Four of these clones, as well as one of four control (pSV2-neo alone) clones, revealed a 3.3 kb mRNA band in the pHTPO-ECE-transfected clones. The size of the human TPO mRNA in the transfected CHO cells is slightly larger than that in the Graves' thyroid cells (3.1 kb), presumably because of the additional SV40 poly-A coding region at the 3' end of human TPO cDNA in the pHTPO-ECE plasmid (see FIG. 1).

Western blot analysis (under reducing conditions) of proteins extracted from TPO-transfected CHO cells, using a mouse monoclonal anti-human thyroid microsomal antibody (Portmann, L., et al., *J. Clin. Invest.* 81:1217–1224 (1988)), revealed an immunoreactive protein of 105–110 kD, as expected for human thyroid peroxidase (Czamocka, B., *FEBS Letters* 109:147–152 (1985); Ohtaki, S., et al., *J. Clin. Endocrinol. Metab.* 63:570–576 (1986)). Briefly, 50 µg of membrane protein or 30 µg of deoxycholate (DOC)-extracted protein from pHTPO-ECE-transfected cell lines (CHO-HTPO4, CHO-HTPO12, CHO-HTPO14, CHO-HTPO11), from a control cell line co-transfected with pECE and pSV2-neo, and from another control cell line transfected with pSV2-neo alone, were subjected to SDS polyacrylamide gel electrophoresis under reducing conditions. The proteins were electrotransferred to nitrocellulose membranes and then probed, as described herein, with a mouse mAb against the thyroid microsomal antigen (Portmann, L., et al., *J. Clin. Invest.* 81:1217–1224 (1988)).

Strong TPO enzymatic activity was evident in clone CHO-HTPO12, and in subclones CHO-TPO12b and CHO-TPO12g, obtained by limiting dilution (Table I). Less enzymatic activity was detected in the other clones. TPO activity in the CHO-TPO12 was approximately the same as TPO activity in TSH-stimulated Graves' thyroid cells in monolayer culture (Table I).

In order to determine whether, as with native TPO in thyroid cells, the recombinant, human TPO was expressed on the surface of the CHO cells transfected with this gene, CHO-HTPO12b cells were subjected to FACS analysis (FIG. 2). Incubation of these cells with high-titer MSA Hashimoto's serum (ELISA value of 1.772; normal<0.2) (Jansson, R., et al., *Clin. Exp. Immunol.* 63:80–86 (1986)) yielded approximately 100-fold greater fluorescence than when these cells were incubated with control serum (FIG. 2). Similar results were obtained with three different Hashimoto's sera. The size of both the control and Hashimoto's serum-incubated cells was the same (FIGS. 3E and 3F), excluding the possibility that differences in cell size were, in part, responsible for the differences in signal.

A series of western blot studies was then performed with protein from CHO-TPO12b cells using a panel of Hashimoto's sera with known antimicrosomal antibody levels as determined by ELISA (Jansson, R., et al., *Clin. Exp. Immunol.* 63:80–86 (1986)). Under non-reducing conditions, all 29 Hashimoto's sera tested, unlike three normal sera, reacted with a major, broad protein band of approximately 200 kD as well as with a fainter doublet of about 110 kD. In aggregate, in studies performed under non-reducing conditions, a total of 36 Hashimoto's sera tested, but not the six control sera, reacted with these bands. The interexperimental variability in the intensity of these bands, however, as well as methodological limitations in analyzing many samples simultaneously, precluded comparison of results of all samples tested.

Nevertheless, it was apparent that, within a single large experiment, the strongest signals were seen with sera containing the highest antimicrosomal antibody ELISA values. Some sera also recognized protein bands other than those expected for TPO. These bands represented wild-type CHO antigens (presented below). One apparent TPO-specific signal of 110 kD also was a non-specific wild-type CHO signal. This is discussed in more detail below.

Comparison of the recombinant TPO signals on western blots performed under reducing and non-reducing conditions (using β-mercaptoethanol) revealed the following with reduction: (a) loss of the 200 kD broad band; (b) alteration of the 110 kD signal so that it no longer clearly represents a doublet; and (c) lessening of the specific signals so that some of the weaker sera become negative. A non-immune serum described above that reacted with a band of approximately 110 kD represents a wild-type CHO protein, and not TPO.

The specificity of the 200 kD and 110 kD bands discussed above was demonstrated in two separate experiments utilizing wild-type, non-TPO-transfected, CHO cells. In the first experiment, selected, potent Hashimoto's sera tested under the most favorable (i.e., non-reducing) conditions failed to react with protein bands of 200 kD or 110 kD. The second experiment indicated that the non-immune serum previously shown to react with a band of 110 kD is a false-positive. This signal in wild-type CHO cells is strong despite the use of unfavorable (i.e., reducing) conditions.

To assess the sensitivity of detection of the specific signal, western blot analyses were performed with serial dilutions of two Hashimoto's sera. The amount of TPO generated in CHO-TPO12b cells was sufficient to be detected even when these Hashimoto's sera were diluted greater than 3000-fold.

Human TPO contains 5 potential glycosylation sites. It was therefore examined whether carbohydrate moieties are important in the conformation of the epitope(s) in the human TPO antigen(s) recognized by Hashimoto's sera. Western blot analyses were performed on proteins extracted from CHO-TPO12b cells pre-cultured for 20 hours in 0.5 µg/ml tunicamycin, an inhibitor of protein glycosylation. This length of time was chosen because it was the longest tolerated without evidence of significant toxicity (i.e., cell loss). Tunicamycin treatment had no apparent effect on antigen recognition, suggesting that carbohydrate moieties may not be important components of the microsomal antigen epitope(s). In a control experiment, tunicamycin treatment under similar conditions decreased radiolabeled D-glucosamine incorporation into proteins by 56.3±4.8% (mean±S.D.; n=3).

An ELISA carried out using antibodies directed against the microsomal antigen (MSA) was compared with an ELISA performed with antibodies directed against the recombinant human TPO of the present invention (FIG. 3). Very good correlation (0.8385249) was observed. In fact, the anti-MSA based ELISA resulted in false positives (indicated as "outlyers" in FIG. 3), which were not observed in the ELISA based upon the anti-recombinant human TPO antibody.

These false positives are likely to result from non-specific reactions of antithyroglobulin antibodies with the microsomes, and were not included in the linear regression calculation for FIG. 3. Support for this conclusion is found in FIG. 4, which shows a linear regression analysis analogous to that shown in FIG. 3, but at a much greater ($1/1000$) dilution. It can be seen from FIG. 4 that the increased dilution factor has substantially eliminated the outlying data points seen at the lower dilution, and that the correlation (0.9060773) is significantly greater. This result strongly suggests that the lowered specificity of the anti-MSA based ELISA is, indeed, a function of antigen contamination. Such problems, which lower assay specificity, might be addressed by the use of non-recombinant, affinity-purified TPO. However, generation of truly pure, affinity-purified natural TPO has proven to be very difficult, if not impossible, to achieve. These problems are avoided by use of the recombinant human TPO antigen of the present invention.

In order to further examine its specificity, recombinant human TPO was compared with Graves' thyroid microsomes as a source of antigen in an ELISA procedure. The recombinant hTPO was present in microsomes prepared from a non-thyroidal, non-human eukaryotic cell line which cannot, therefore, contain thyroid-specific antigens other than hTPO. Nevertheless, because sera from patients with autoimmune thyroiditis contain antibodies against numerous antigens, some of which may be present in Chinese hamster ovary (CHO) cells (Kaufman, K. D., et al., *J. Clin. Invest.* 84:394–403 (1989)), each serum sample was also assayed against microsomes prepared from control, non-transfected CHO cells.

Figure 10A:
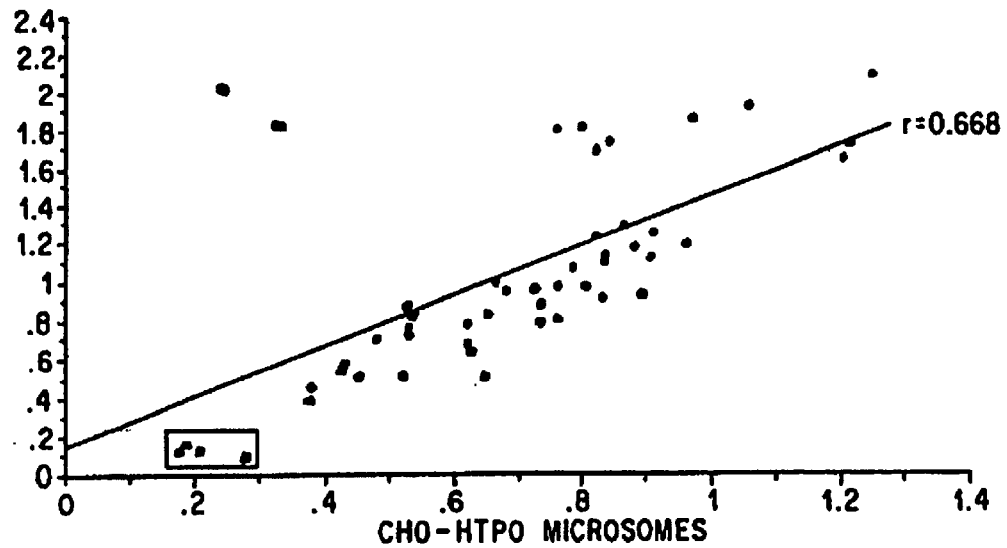

In comparing the 51 sera at a standard ($1/100$) dilution in both the recombinant hTPO and the thyroid microsomal assay, a moderately good correlation was observed (r=0.668; p<0.001) (FIG. 10A). Clearly, however, there were some widely discrepant values. In particular, two sera (sera #11 and 27, FIG. 10A, large circle and square, respectively) that were very potent in the anti-MSA assay gave values in the anti-hTPO antibody assay similar to the four normal sera (FIG. 10A, four data points within rectangle near the origin). A number of other sera, primarily in the high range of activity, also gave significantly higher values with the thyroid microsomal preparation than with recombinant hTPO (FIG. 10A). At the same serum dilution, a much lower correlation was observed between the values obtained with thyroglobulin and recombinant hTPO as antigen (r=0.315; p<0.05).

Figure 10B:
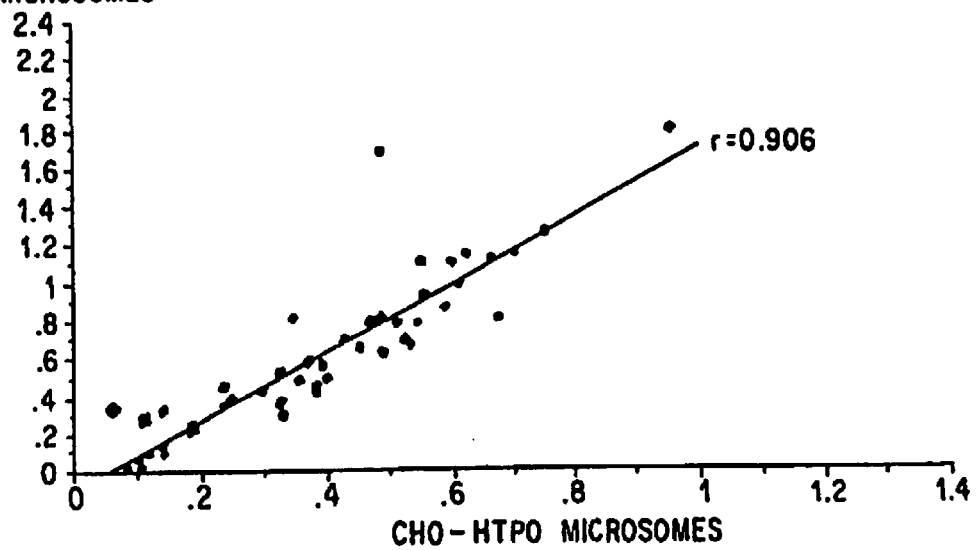
Figure 10C:
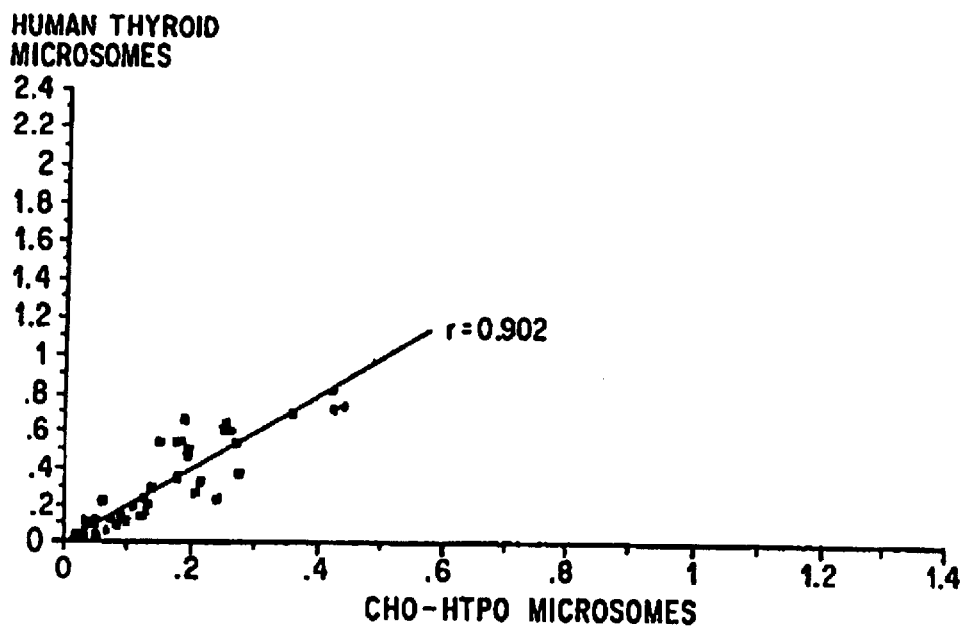

In an autoimmune serum containing antibodies against multiple antigens, the different antibodies are likely to have varying affinities for their respective antigens. Serial dilutions of sera will yield different profiles of ELISA values based on the affinity of each antibody-antigen interaction. If hTPO is the primary autoantigen in the thyroid microsomal preparation, the same serum dilution curve should therefore be observed in assays using thyroid microsomes and recombinant hTPO. In support of this hypothesis, at serum dilutions of $1/1000$ or $1/10,000$, the correlation in ELISA values between thyroid microsomes and human TPO was much greater (r=0.906 and 0.902, respectively; p<0.001) (FIGS. 10B and 10C). Dramatically, the two sera that were strongly positive with the thyroid microsomal but not with the recombinant hTPO antigen (FIG. 10A) were no longer significantly discrepant between the two assays (FIG. 10B and 10C). The dilution curves for these two sera were quite different in the anti-MSA and anti-hTPO antibody assays (FIGS. 11A and 11B), confirming that these sera were reacting with low affinity to an antigen other than hTPO. These two sera were also distinguished by their surprisingly high levels of anti-thyroglobulin antibody. In contrast, other sera with similar anti-MSA levels (at $1/100$ serum dilution) yield normal dilution curves in both assays (sera #12 and 28, FIGS. 11A and 11B).

The anti-hTPO antibody ELISA data were also expressed as the difference between values obtained using the CHO-HTPO microsomes and the CHO-K1 microsomes as antigen, to correct for possible interference by anti-CHO cell antibodies (Kaufman, K. D., et al., *J. Clin. Invest.* 84:394–403 (1989)). No significant change was found in the correlation between the thyroid microsomal and the recombinant hTPO assays using these revised data at each of the three serum dilutions. Anti-CHO-K1 antibody ELISA values for the 47 sera of patients with autoimmune thyroid disease tested, at standard ($1/100$) dilution, were 0.164±0.066 SD (mean±SD).

The precision of the anti-hTPO antibody ELISA was assessed using three sera chosen to represent a spectrum of autoantibody potency. Intra-assay variability (10 iterations for each serum) at standard ($1/100$) serum dilution, expressed as mean±SD (FIG. 12), was 0.346±0.18 (low-potency serum), 0.599±0.44 (medium-potency serum), and 0.923±0.94 (high-potency serum). The intra-assay coefficients of variation (CV) for these sera were 5.12%, 7.39%, and 10.2%, respectively. The inter-assay CV's (7 iterations for each serum) were 5.36%, 7.63%, and 7.29%, respectively.

In another aspect of the present invention, it has surprisingly been discovered that CHO cell expression of human TPO can be significantly increased by employing a different plasmid. A dihydrofolate reductase (DHFR)-TPO construct has been made in which both genes (DHFR and TPO) are driven by the SV40 promoter (FIG. 4). Screening of CHO cells transfected with these constructs has produced two plasmids, designated pHTPO-DHFR-2B and pHTPO-DHFR-4C, which presently express three-fold more antigen than that achieved using the pECE-HTPO plasmid.

The relative TPO activities observed in CHO cells transfected with pECE-HTPO, pHTPO-DHFR-2B and pHTPO-DHFR-4C are shown plotted against methotrexate concentration in FIG. 5. Further, one particular subclone, designated pDHFR-TPO-4C-MTX, has been found to express relatively greater amounts of TPO than any other construct so far isolated, and, in this regard, comprises the best mode presently contemplated of expressing human TPO in CHO cells. The plasmid pDHFR-TPO-4C-MTX was deposited at the American Type Culture Collection, 12301 Parklawn Drive, Rockville, Md. 20852 on Oct. 3, 1989, with accession number CRL 10250.

FIG. 5 shows that, with increasing methotrexate concentrations, a plateau is reached for CHO expression of TPO by the pHTPO-DHFR-2B and pHTPO-DHFR-4C plasmids. While not intending to be bound by any particular theory, one possible explanation for this observation is that the expressed full length TPO gene is toxic to the host CHO cells, resulting in selection for DHFR, but against TPO, at higher methotrexate concentrations. The result of such selection might be that DHFR is amplified while TPO is deleted.

Since the full length TPO gene is membrane-associated, the present inventor hypothesized that it may be possible to increase TPO production in CHO cells if the expressed protein could somehow be dissociated from the membrane. Accordingly, experiments have been undertaken to generate a secretable form of human TPO, by identifying and eliminating the wild-type transmembrane sequence from the gene.

Premature termination in the synthesis of hTPO was hypothesized to reduce the size of the hTPO-M1 protein from 933 to 848 amino acids. An original full length human TPO cDNA clone in Bluescript (pHTPO-BS) was submitted to site-directed mutagenesis to produce plasmid pHTPO(M1)-BS. A single-stranded DNA template was generated, and the indicated 52-mer oligonucleotide probe used for mutagenesis. The mutations incorporated two stop codons, as well as an EcoR1 site for confirmation, in the region immediately upstream from the transmembrane region of the human TPO gene (FIG. 6). The entire full length human TPO gene sequence is shown for comparison in FIG. 7.

As a consequence of the mutation, a "truncated" human TPO protein is expressed which is secreted by the host cell rather than bound to its membrane. The mutated hTPO gene was excised from pHTPO(M1)-BS using Not I (blunted with Klenow polymerase) and Xba I, and was inserted into the corresponding sites of pECE-SV2-DHFR, to produce the expression plasmid pHTPO(M1)-ECE-SV2-DHFR (FIG. 8). CHO cells transfected with this plasmid appear to produce a truncated human TPO protein, which is believed to retain the antigenic properties of the full length protein, and which, accordingly, comprises another embodiment of the present invention. Construction of the plasmid pHTPO (M1)-ECE-SV2-DHFR is summarized in FIG. 9.

After stable transfection of CHO cells with the plasmid pHTPO(M1)-ECE-SV2-DHFR containing the mutated hTPO cDNA, individual colonies of cells (CHO-TPO-M1) were studied for the expression of TPO (FIG. 14).

Figure 14A:
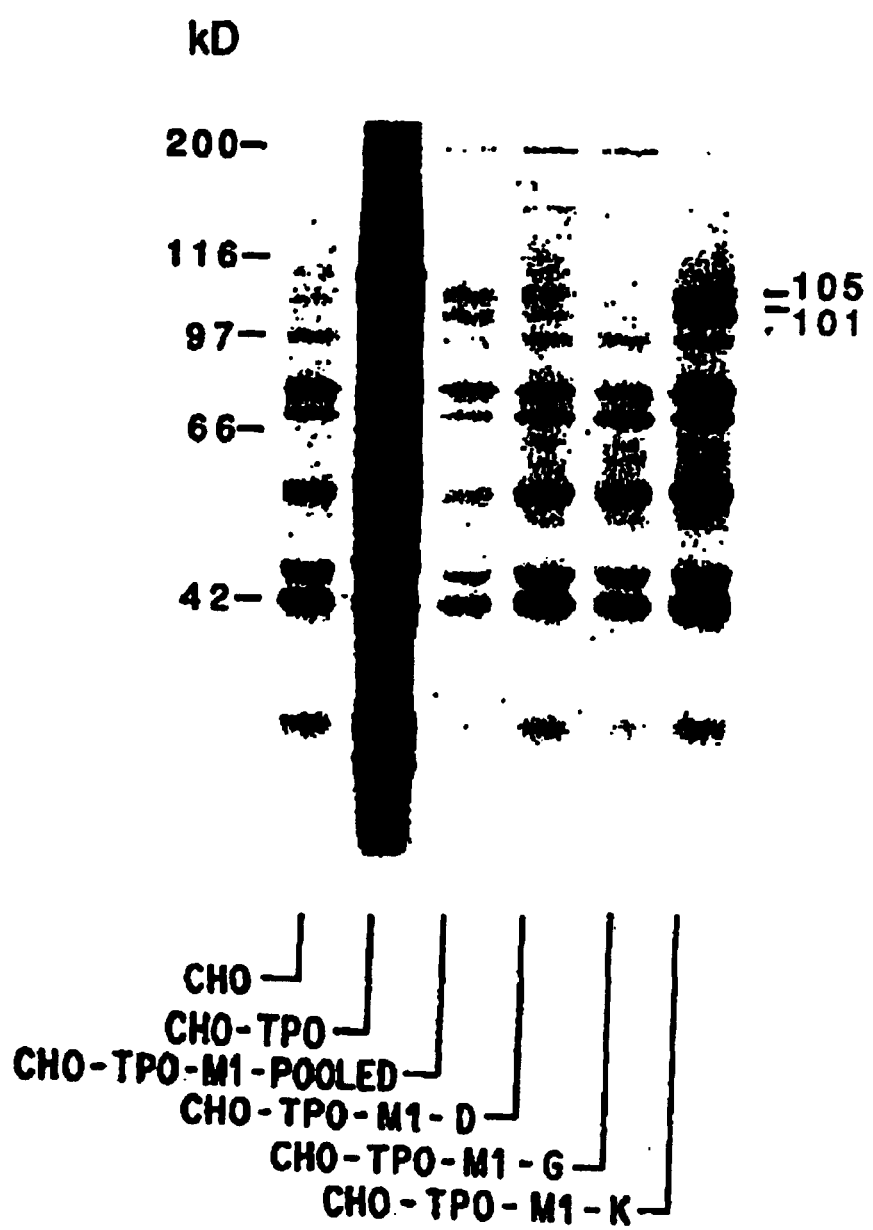

Because the kinetics of potentially-secreted hTPO-M1 protein were unknown, the expression of this protein was initially screened for in CHO cell lysates, since particulates TPO would be expected to be detectable even if the protein were, in large part, secreted. Randomly selected CHO-TPO-M1 clones showed evidence of variable cellular TPO expression (FIG. 14). A doublet of approximately 105–101 kD was specifically immunoprecipitated from lysates of these clones by serum from a patient with Hashimoto's thyroiditis. In CHO cells transfected with wild-type hTPO cDNA, Hashimoto's serum immunoprecipitated a doublet of larger size, 112–105 kD, and neither doublet was detected in non-transfected CHO cells (FIG. 14A), as previously observed (Kaufman, K. D., et al., *J. Clin. Invest.* 84:394–403 (1989)). Immunoreactive TPO was absent from the cell surface of the CHO-TPO-M1 cells, as demonstrated by the lack of immunofluorescence when these cells were pre-incubated with Hashimoto's thyroiditis serum and fluorescently-tagged goat anti-human IgG antibody, unlike CHO cells transfected with wild-type hTPO (Kaufman, K. D., et al., *J. Clin. Invest.* 84:394–403 (1989)).

Figure 14B:
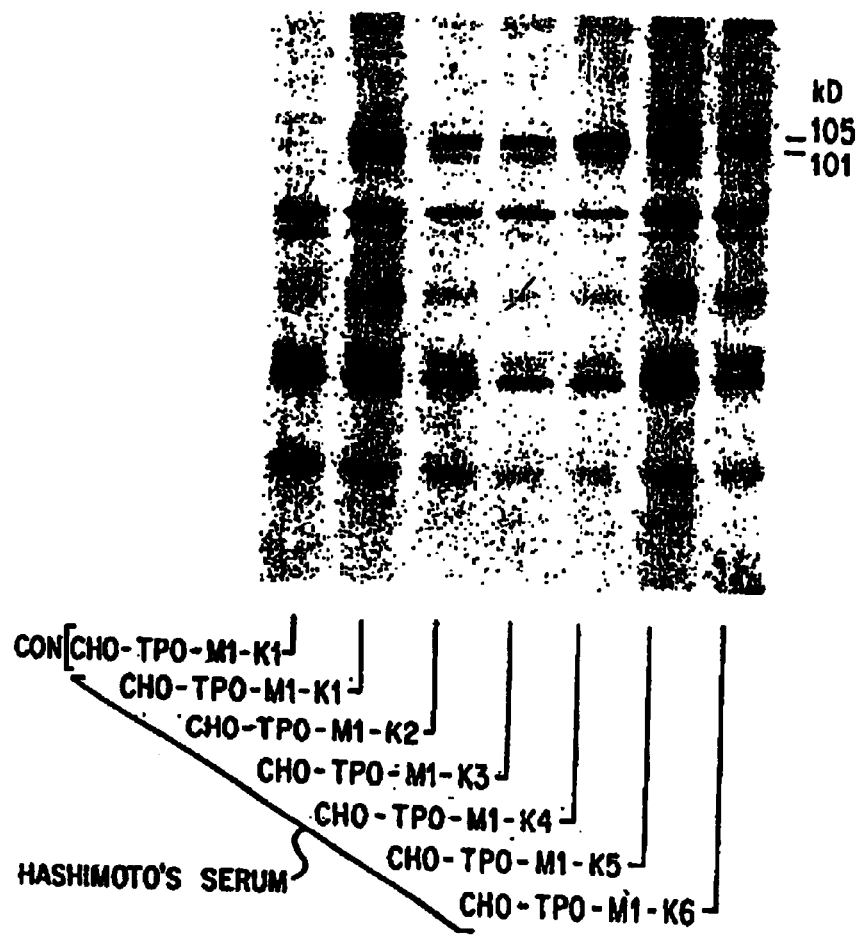

In order to determine whether mutated hTPO-M1 is a secreted protein, the biosynthesis and processing of both hTPO-M1 and wild-type hTPO was examined in pulse-chase experiments. First, clone CHO-TPO-M1-K, with the highest expression of truncated TPO (FIG. 14A), was subcloned by limiting dilution, and one cell line (CHO-TPO-M1-K1) was selected for further studies (FIG. 14B). Over a 24 hour chase period, radiolabeled hTPO-M1 protein was secreted by cells into the culture medium and detected by immunoprecipitation with Hashimoto's serum (FIG. 15). This secreted protein was present in the culture medium after 4 hours of chase, with levels accumulating progressively over a 24 hour period. Interestingly, the secreted, immunoprecipitable hTPO-M1 protein appeared as a single band of lesser electrophoretic mobility on the polyacrylamide gel, as compared with its cell-associated form. In contrast, CHO cells expressing wild-type hTPO secreted no detectable immunoprecipitable material into the culture medium. The cell-associated hTPO and hTPO-M1 proteins were similarly stable, with their radiolabeled immunoprecipitates increasing between 0 and 4 hours of chase. Amounts of radiolabeled, immunoprecipitable wild-type hTPO protein at 24 hours of chase were similar to baseline (0 hours). The observed decrease in signal in CHO-TPO-M1-K1 cell lysates from 4 to 24 hours is paralleled by an increase in signal in the medium of these cells, supporting the concept of a secreted protein, which, accordingly, comprises another embodiment of the present invention.

In order to prove that the immunoprecipitable material released into the culture media by CHO-TPO-M1-K1 cells was, indeed, TPO, conditioned media were tested for TPO enzymatic activity. TPO activity (1.0 guaiacol U/10 ml medium) was clearly present in the culture medium from the CHO cells expressing the mutated form of hTPO (FIG. 16). In contrast, there was no detectable enzymatic activity in conditioned media from CHO cells expressing wild-type hTPO (FIG. 16), despite strong TPO activity present in lysates of these cells, as previously described (Kaufman, K. D., et al., *J. Clin. Invest.* 84:394–403 (1989)).

TABLE I

Thyroid Peroxidase (TPO) Activity in CHO-TPO12 Cells and in TSH-Stimulated Graves' Disease Human Thyroid Cell Primary Cultures

| Cell Type | Guaiacol Peroxidase (units/mg protein) | Iodide Peroxidase (units/mg protein) |
|---|---|---|
| CHO-pECE (control) | 0 | 0 |
| CHO-pSV2-neo (control) | 0 | 0 |
| Human thyroid cells | 4.7 | 3.0 |
|  | 4.6 | 3.4 |
| CHO-HTPO12 | 3.6 | nd |
| CHO-HTPO12b | 4.0 | 3.1 |
| CHO-HTPO12g | 3.1 | 1.9 |

Summary of data from multiple determinations of guaiacol and iodide TPO activity measured in deoxycholate extracts, prepared from 100 mm diameter dishes of the indicated cells. Graves' disease-affected human thyroid cells were cultured for 3 days in 12.5 mU/ml human TSH.
nd - not done

EXAMPLE XII

TPO Specific T Cells Infiltrate Thyroid in Graves' Disease

Taking advantage of the availability of recombinant TPO, the occurrence of in vivo selection for T cells specific for this autoantigen in the intrathyroidal population has been examined.

A. METHODS

Infiltrating mononuclear cells were extracted from the thyroidectomy specimen of a 26 year old female (CX81:HLA-A1, 2; B8, 37; DR3; DRw52; DQw2) with persistently relapsing Graves' disease and a high titer of antithyroid microsomal antibodies (1:640) by enzyme digestion followed by overnight incubation and separation of the non-adherent cells as previously described (Londei, M. et al., *Science* 228:85–89 (1985)). The activated cells were selectively expanded by growth in recombinant IL-2 (Ajinomoto—20 ng/ml) and 10% human serum in RPMI-1640 (Gibco) for one week. Cells were further expanded, nonspecifically with the addition of irradiated autologous peripheral blood lymphocytes as feeder cells, OKT3 monoclonal antibody (30 ng/ml) and IL-2 for two weeks prior to cloning at limited dilution (0.5 cells/well) with OKT3/IL-2 and DR-matched antigen presenting cells (APC). Further expansion and maintenance of all clones was by 1–2 weekly restimulations with OKT3/IL-2 and HLA unmatched irradiated feeder cells. Cells were assayed at the end of the feeding cycle and a minimum of 5 days after their last exposure to IL-2.

Proliferation assays were performed over 3 days in triplicate microtiter wells. Irradiated autologous PBL ($2-5\times10^4$) were added to $10^4$ clone T cells in 200 µl of 10% human serum. 1 µl of neat microsome (protein concentration 5 mg/ml) was added per well. 1 µCi of [$^3$H]thymidine was added for the final 6 hours of the assay prior to harvesting onto glass fiber filters and scintillation counting.

Peripheral blood mononuclear cells purified by sucrose gradient centrifugation (Lymphoprep-Nycomed) were incubated at $10^5$ cells per well in microtiter wells containing 200 µl 10% human serum. Control or TPO microsomes in 1–2 µl were added per well as above. Cultures were incubated for 5–6 days and pulsed with [$^3$H]thymidine in the last 6–18 hours prior to harvesting and scintillation counting.

Transfection of CHO cells with the complete cDNA for Human TPO cloned into the expression vector pECE and the preparation of cell microsomes from transfected and untransfected CHO cells was as described above.

B. RESULTS

In vivo activated thyroid infiltrating T cells were selected by growth in recombinant IL-2. The resultant population was then further expanded non-specifically by stimulation with anti-C1B3 antibodies (OKT3) in combination with IL-2. Lines so derived consistently showed a marked response to autologous thyroid epithelial cells in the absence of added antigen-presenting cells (APC). For example, the following levels of T cell stimulation, measured as incorporation of radiolabeled thymidine, were observed:

T cells: 51±3 cpm;

Thyroid epithelial cells (TEC): 62±8 cpm;

T cells+TEC: 6108±1040 cpm.

T cell clones were obtained by plating the lines at limiting dilution (0.5 cells/well) followed by further expansion with IL-2 and OKT3. In this way, antigen-specific selection was avoided prior to screening of the clones.

Figure 17A:
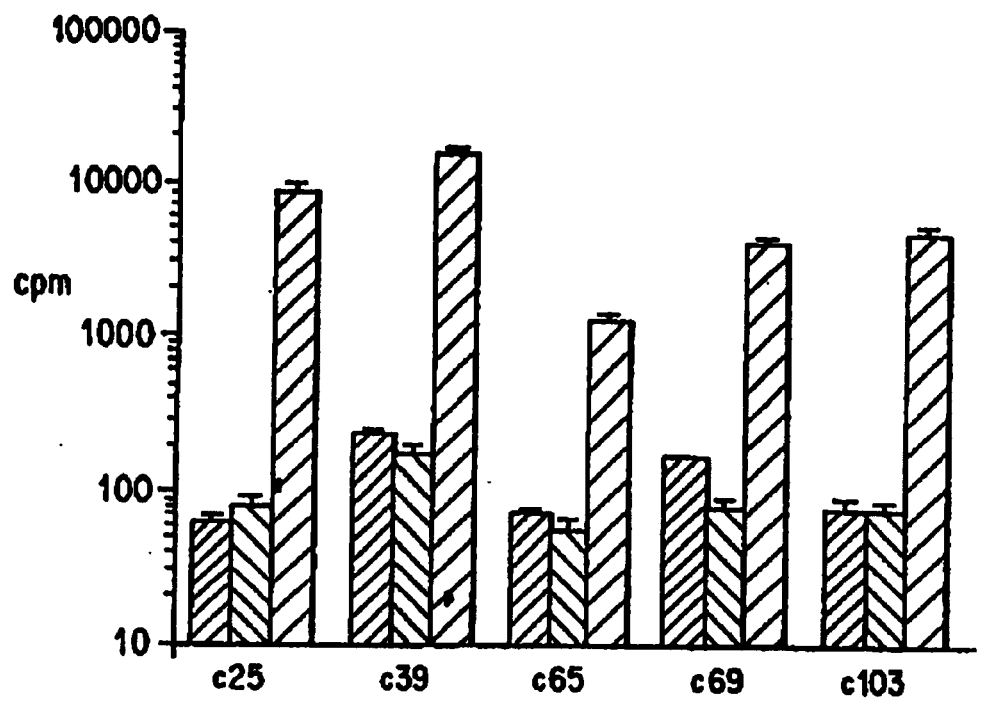

The complete sequence of human TPO cDNA was cloned into the mammalian expression vector pECE and transfected into Chinese Hamster Ovary (CHO) cells as described above. These transfected cells express high levels of immunoreactive and enzymatically active TPO. Microsomes prepared from transfected CHO cells were found to induce significant proliferation of 5 of 24 clones derived from the intrathyroidal population (FIG. 17A). These cells showed no response to untransfected CHO microsomes (FIG. 17A).

Figure 17B:
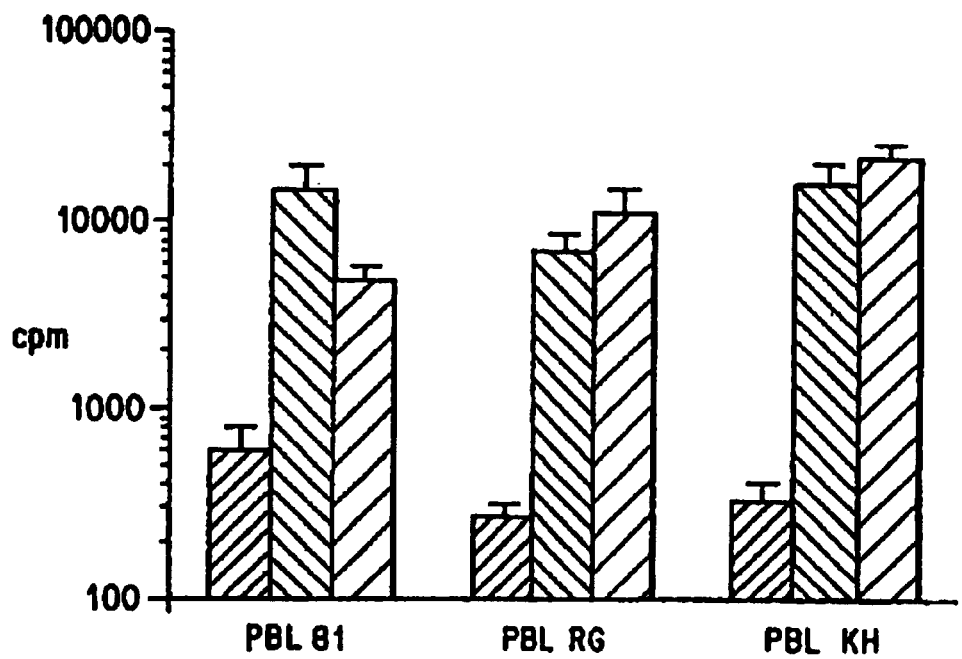

In contrast, peripheral blood T cells (PBL) from the same individual, from other Graves' patients, or from normal controls, responded to both transfected and untransfected preparations (FIG. 17B). PBL reactivity to CHO cell derived proteins is not unexpected as similar reactivity has been described with other xenogeneic cell extracts (Van Vliet, E. et al., *Europ. J. Immunol.* 19:213–216 (1989)). However, it demonstrates the difference in antigenic repertoire between thyroid infiltrating and peripheral blood T cells, as at no time was any response to untransfected CHO microsomes seen with thyroid-derived T cells (FIG. 17A and Table IV).

TABLE II

Sites Of NP Synthetic Peptides In Human TPO

| 1 | |
|---|---|
| —933 | |
| NP-1 | 111–131 |
| NP-2 | 116–131 |
| NP-3 | 187–204 |
| NP-4 | 234–250 |
| NP-6 | 426–440 |
| NP-7 | 535–551 |
| NP-8 | 669–686 |
| NP-9 | 693–716 |
| NP-10 | 724–739 |
| NP-13 | 487–504 |

Position of synthetic peptides used to screen T cells in human TPO sequence. Residues are numbered from the amino-terminus.

TABLE III

Responses of T Cell Clone c43 to NP Peptides

| Peptide | Concentration (μg/μl) | | |
|---|---|---|---|
| | 0.1 | 1.0 | 10 |
| NP-1 | 48 | 72 | 52 |
| NP-2 | 85 | 54 | 63 |
| NP-3 | 59 | 62 | 62 |
| NP-4 | 50 | 67 | 100 |
| NP-6 | 65 | 60 | 102 |
| NP-7 | 271 | 6190 | 16235 |
| NP-8 | 68 | 85 | 221 |
| NP-9 | 69 | 52 | 80 |
| NP-10 | 63 | 101 | 55 |
| NP-13 | 38 | 69 | 121 |

Responses (in counts per minute, cpm) of thyroid derived T cell clone c43 to the panel of synthetic peptides of Table II. Peptides were used at the concentrations shown. Response of c43 + autologous feeders alone was 101 ± 16 cpm. S.E.M. of responses was consistently less than 15% of the mean. The response of c43 to NP-7 was confirmed in 5 subsequent experiments with similar results.

TABLE IV

Response of T Cell Clones to TPO Microsomes and to NP-7

| | Antigenic Preparation | | | |
|---|---|---|---|---|
| Clone | Control Microsome | TPO Microsome | APC | APC + NP-7 (10 μg/μl) |
| c25 | 79 ± 13 | 8024 ± 1144 | 123 ± 32 | 78 ± 8 |
| c39 | 175 ± 22 | 13824 ± 1556 | 236 ± 19 | 276 ± 65 |
| c65 | 54 ± 11 | 1203 ± 111 | 70 ± 4 | 64 ± 6 |
| c69 | 78 ± 10 | 3757 ± 517 | 167 ± 4 | 232 ± 89 |
| c103 | 75 ± 12 | 4575 ± 479 | 76 ± 12 | 54 ± 5 |
| c43 | 654 ± 396 | 2121 ± 554 | 82 ± 12 | 17173 ± 1984 |
| c75 | 84 ± 15 | 151 ± 30 | 346 ± 107 | 2544 ± 135 |
| c104 | 44 ± 6 | 260 ± 26 | 68 ± 14 | 5015 ± 747 |
| c105 | 172 ± 30 | 1028 ± 141 | 599 ± 59 | 4455 ± 338 |
| c3 | 71 ± 11 | 78 ± 20 | 75 ± 11 | 60 ± 5 |
| c9 | 72 ± 4 | 452 ± 32 | 71 ± 4 | 258 ± 46 |
| c18 | 63 ± 3 | 62 ± 10 | 49 ± 6 | 51 ± 1 |
| c20 | 126 ± 21 | 704 ± 89 | 102 ± 9 | 106 ± 17 |
| c29 | 121 ± 27 | 156 ± 17 | 107 ± 7 | 86 ± 5 |
| c60 | 197 ± 110 | 345 ± 84 | 310 ± 53 | 536 ± 50 |
| c64 | 50 ± 3 | 160 ± 13 | 86 ± 20 | 228 ± 52 |
| c70 | 76 ± 17 | 138 ± 23 | 93 ± 20 | 154 ± 20 |
| c77 | 61 ± 8 | 645 ± 284 | 94 ± 11 | 242 ± 43 |
| c82 | 1844 ± 143 | 4246 ± 176 | 8318 ± 191 | 6632 ± 292 |
| c83 | 192 ± 44 | 139 ± 26 | 130 ± 13 | 77 ± 7 |
| c94 | 95 ± 8 | 114 ± 17 | 70 ± 6 | 92 ± 8 |
| c95 | 44 ± 6 | 89 ± 9 | 62 ± 25 | 274 ± 48 |
| c98 | 87 ± 9 | 96 ± 14 | 88 ± 8 | 70 ± 5 |
| c100 | 99 ± 15 | 81 ± 10 | 252 ± 10 | 166 ± 8 |

Responses of thyroid-derived T cell clones to TPO microsomes and peptide NP-7. NP-7 (10 μg/ml) or control or TPO microsomes (0.5 to 1 μl) were added per well as indicated. Autologous irradiated PBL or EBV-transformed B cells were used as antigen presenting cells (APC) at an APC:T cell ratio of between 2 and 5. Results are the man cpm (± S.E.M.) of triplicate wells. Positive results were confirmed in 2 to 7 different experiments.

Clones were further screened using a panel of 10 synthetic peptides based on the TPO sequence, selected using two T cell motif algorithms (Rothbard, J. B., *Ann. Inst. Pasteur* 137E:518–526 (1986); DeLisis, C. et al., *Proc. Natl. Acad. Sci. USA* 82:7048–7052 (1985)) as shown in Table II. Two clones (c43 and c105) which showed only a small response to TPO microsomes (Table IV) showed a specific response to a peptide (NP-7) corresponding to residues 535–551 of TPO (Table III and IV). Two additional clones (c75 and c104), unresponsive to the whole TPO microsome preparation, showed significant responses to NP-7. In contrast, the 5 clones highly reactive to TPO microsomes (c25, c39, c65, c69, c103) did not respond to NP-7 (Table IV). No response to NP-7 was seen with the patients' peripheral blood T cells (PBL alone=609±190 cpm; PBL+ NP-7 (10 μg/ml)=302±38 cpm).

C. DISCUSSION

The lack of recognition of NP-7 by TPO responsive clones suggests the presence of additional T cell epitopes on TPO distinct from NP-7. The observation that clones specific for an epitope derived from the TPO sequence (NP-7) are present at high frequency in the thyroid infiltrate, and yet respond poorly or not at all to whole TPO presented by APC of peripheral blood origin, is noteworthy.

These results provide the first clear evidence in human organ-specific autoimmunity that a significant proportion of activated T cells infiltrating the target tissue recognize an antigenic protein specific to that tissue. This is consistent with the finding of collagen type II-specific T cells in the joint in rheumatoid arthritis (Londei, M. et al., *Proc. Natl. Acad. Sci. USA* 86:636–640 (1989)). These results also define the site of a T cell epitope within TPO (residues 535–551) and provide evidence for the presence of at least two distinct epitopes on a single target molecule in the same individual. Such information is very important for the design of appropriate peptide-based immunotherapy, as discussed above.

EXAMPLE XIII

Molecular Determination of a B Cell Epitope of TPO

To determine precisely, at the amino acid level, the epitopes in human TPO that are recognized by antibodies in the sera of patients with autoimmune thyroid disease, a panel of mAbs generated against natural TPO was studied. The binding of some of these mAbs to TPO was inhibited by patients' sera, and determination of the TPO epitopes recognized by these mAb would, indirectly, define the disease-associated epitope(s).

This panel of 13 mAbs was used to screen a lambda-Zap library constructed to contain, exclusively, 200–500 bp random fragments of TPO cDNA. When expressed as bacterial fusion proteins, 1/6 of the 3.8×10$^6$ cDNA fragments would express random 66–166 amino acids fragments of TPO.

For screening, binding of murine anti-TPO mAb (1:40 dilution) was detected using peroxidase-conjugated goat anti-mouse immunoglobulin antibody. Positive plaques were revealed with only one of the thirteen mAb tested (mAb-47). MAb-47 bound TPO with high affinity but did not interfere with the enzymatic activity of TPO. Human anti-TPO autoantibodies strongly inhibited the binding of mAb-47 at 1:20 dilution.

The nucleotide sequences of seven randomly selected clones recognized by mAb-47 were determined. All the clones spanned the same region of the TPO cDNA, overlapping in the region of 2180–2171 bp. This region encodes 30 amino acids (at position 698–728) in the TPO protein.

Anti-TPO mAb-47 is unique among 13 mAbs tested in that it recognizes a continuous epitope on TPO. The other mAbs presumably recognize discontinuous epitopes. The competitive binding to TPO of mAb-47 and naturally occurring anti-TPO autoantibodies suggests that mAb-47 defines a natural, disease-associated TPO epitope.

To further elucidate the molecular and cellular basis for the pathogenesis of autoimmune thyroid disease, it will be very important to identify the sites (epitopes) on TPO recognized by the anti-TPO antibodies in Hashimoto's thyroiditis patients. Prior approaches to the examination of this question have included the use of immunological probes (polyclonal or monoclonal anti-TPO antisera) (Libert, F., et al., EMBO J. 6:4193–4196 (1987); Ludgate, M., et al., J. Clin. Endocrinol. Metab. 68:1091–1096 (1989); Doble, N. D., et al., Immunol. 64:23–29 (1988); Ruf, J., et al., Endocrinol. 125:1211–1218 (1989); Laing, P., J. Clin. Lab. Immunol. 19:19–23 (1986); Kohno, Y., et al., J. Clin. Endocrinol. Metab. 68:766–773 (1989)) and limited proteolytic digestion (Yokoyama, N., et al., J. Clin. Endocrinol. Metab. 68:766–773 (1989)). By these means, several distinct antibody binding regions appear to be present in TPO.

However, TPO is an extremely large antigen (approximately 107 kD), and these techniques have not allowed definition of the precise epitopes involved. The present inventor therefore undertook to screen, with sera from patients with Hashimoto's thyroiditis, a bacteriophage (lambda-Zap) human thyroid cDNA expression library containing large numbers of hTPO cDNA fragments.

Each of these fragments is 200–500 b.p. in length, coding for TPO polypeptides of 66–166 amino acids. The entire hTPO protein comprises 933 amino acids. These TPO polypeptide fragments are expressed as bacterial fusion proteins, so called because the protein is a hybrid of a 10 kD fragment of β-galactosidase linked to the thyroid protein component.

METHODS

TPO cDNA fragment library construction: A full-length (3.05 kb) cDNA clone as described above for human thyroid peroxidase was released from its Bluescript vector (Stratagene, San Diego, Calif.) by digestion with EcoRI (BRL Laboratories, Gaithersburg, Md.) and NotI (Boehringer, Mannheim, West Germany). Because both vector and insert are of similar length, the Bluescript was further digested with Sca1 (New England Biolabs, Beverly, Mass.). The TPO cDNA was purified by agarose gel electrophoresis and electroelution. The cDNA was then digested (6 minutes at room temperature) into small random-sized fragments with DNAase I (0.1 ng DNase/ug cDNA) (BRL) in 20 mM Tris-HCl, pH 7.5, 1.5 mM $MnCl_2$ and bovine serum albumin, 100 ug/ml. After electrophoresis in 2% SeaPlaque agarose (FMC Bio Products, Rockland, Me.), TPO cDNA fragments 200–500 b.p. in length were recovered by electroelution. The ends of the fragments were blunted with the Klenow fragment of DNA polymerase I, and ligated to EcoRI linkers (GAATTCGGCACGAG) (SEQ ID NO: 9) containing a nonphosphorylated EcoRI cohesive end and a phosphorylated blunt end (Pharmacia, Piscataway, N.J.). After phosphorylation with polynucleotide kinase, excess linkers were removed by electrophoresis in 2% SeaPlaque agarose. The linker-ligated cDNA was again size-selected (200–500 b.p.), electroeluted, ethanol precipitated and ligated into EcoRI-cut lambda-Zap vector (Stratagene). After packaging (Giga-Pak Gold, Stratagene), the library was amplified in XL1-blue cells (Stratagene). cDNA insert sizes were confirmed by the polymerase chain reaction (PCR) (Saiki, R. K., et al., Science 239:487–491 (1988)) using the Bluescript reverse and −20 primers. PCR analysis of the "C2" hTPO cDNA region (Libert, F., et al., EMBO J. 6:4193–4196 (1987); Ludgate, M., et al., J. Clin. Endocrinol. Metab. 68:1091–1096 (1989)) in the TPO cDNA fragment library was performed using two oligonucleotide 22-mer primers (5'-GGTTACAATGAGTGGAGGGAGT (SEQ ID NO: 10) and 5'-GTGGCTGTTCTCCCACCAAAAC) (SEQ ID NO: 11) spanning the region 1852–2112 b.p. in hTPO (17). PCR (30 cycles) was for 1 minute at 94° C., 2 minutes at 55° C. and 1 minute at 72° C. For screening the library, the PCR-generated DNA was labeled with $^{32}P$-αCTP to a specific radioactivity of $0.8 \times 10^9$ cpm/µg DNA using the random primer method (Multiprime; Amersham, Arlington Heights, Ill.). The screening procedure employed standard techniques (Maniatis, T., et al., Molecular Biology: A Laboratory Manual, Cold Spring Harbor Laboratory, Cold Spring Harbor, N.Y. (1982)), with final washes of 30 minutes (×2) at 55° C. in 0.1×SSC, 1% SDS buffer (1×SSC in 150 NaCl, 15 mM Na citrate, pH 7.5). Autoradiography of the nitrocellulose filters was performed with Kodak XAR-5 film.

Immunological screening of the TPO sub-library: The lambda-Zap library containing TPO cDNA fragments, plated in E. coli Y1090 at about $3 \times 10^4$ pfu per 150 mm diameter Petri dish, was screened as previously described (Seto, P., et al., J. Clin. Invest. 80:1205–1208 (1987)). In brief, after 3.5 hours at 42° C., nitrocellulose filters soaked in 10 mM isopropyl-thio-beta-D-galactopyranoside (IPTG) were overlayed for 3.5 hours at 37° C. Filters were removed, washed in TBS buffer (10 mM Tris HCl, pH 7.5, 150 mM NaCl) containing 0.05% Tween, incubated for 15 minutes at room temperature in TBS/Tween containing 2% Carnation milk, rinsed with TBS/Tween, and then incubated overnight at 4° C. with antibody. For immunological screening, mouse monoclonal antibody (#20.10) against the thyroid microsomal antigen (Portmann, L., et al., J. Clin. Invest. 81:1217–1224 (1988)) was used at a 1:200 dilution. Because of the very low background and strong signal achieved with monoclonal antibodies, pre-adsorption with bacterial proteins is not necessary prior to screening, as previously described (Seto, P., et al., J. Clin. Invest. 80:1205–1208 (1987)). Antisera from 13 Hashimoto's thyroiditis patients with high titer antimicrosomal antibodies were used under a variety of different conditions at a dilution of 1:200. In contrast to previous experience in screening lambda gt11 libraries with Hashimoto's sera (Hirayu, H., et al., J. Clin. Endocrinol. Metab. 64:578–584 (1987)), screening of the lambda-ZAP libraries provided very little background with such sera, and, in general, pre-adsorption was not required to reduce this non-specific background. When pre-adsorption was performed, Y1090 proteins were immobilized on nitrocellulose filters. In addition, affinity-purified anti-TPO antibodies, prepared using recombinant hTPO expressed on the surface of Chinese hamster ovary (CHO) cells also were used as immobilized antigen (Kaufman, K. D., et al., J. Clin. Invest. 84:394–403 (1989)). For this procedure, 1 ml of serum was diluted 1:10 in phosphate-buffered saline (PBS) containing 0.05% Na azide and 1 mM phenylmethyl sulfonylfluoride (PMSF). TPO-CHO cells (approximately $10^8$) were resuspended by light trypsinization, diluted in PBS containing 10% calf serum, pelleted (5 minutes at 1,000×g), and resuspended in the diluted antibody for 1 hour at 4° C. Unbound antibody was removed by pelleting the cells, followed by a rinse in ice-cold PBS. After recovery by centrifugation (5 minutes at 1,000×g), the cells were resuspended and incubated for 15 minutes at 4° C. in 150 mM acetic acid in PBS containing 0.05% Na azide and 1 mM PMSF. NaOH and 1 M Tris, pH 7.5, were added to neutralize the acetic acid, and the cells and particulate material were removed by centrifugation (5 minutes at 1,000×g, and then for 3 minutes at 100,000×g, 4° C.), leaving the affinity-purified antibody in the supernatant. The efficiency of the affinity purification was approximately 50%, as measured by ELISA (Schardt, C. W., et al., J. Immunol. Methods 55:155–168 (1982)).

The detection systems for antibody bound to fusion proteins were as previously described (Seto, P., et al., J. Clin.

*Invest.* 80:1205–1208 (1987)), using the following antisera: For the mouse antimicrosomal monoclonal antibody, peroxidase-conjugated, affinity-purified goat anti-mouse IgG (heavy and light chain specific) (Cappel, Organon, West Chester, Pa.) at a dilution of 1:300; For the polyclonal human antisera, anti-human IgG (Fc fragment, gamma chain specific) (Cappel) at a dilution of 1:300. Color was developed with 2.8 mM 4-chloro-1-naphthol (Sigma, St. Louis, Mo.). The quality of the immunological reagents used in the polyclonal antibody screening procedure was confirmed by their ability to generate a strong signal with eukaryotic recombinant hTPO on western blot analysis (Kaufman, K. D., et al., *J. Clin. Invest.* 84:394–403 (1989)). Positive clones were plaque-purified to homogeneity. Control screening of potentially positive plaques was performed by omitting the first (anti-TPO) antibody in the screening procedure.

Nucleotide sequence analysis of selected clones: Plaque-purified lambda-Zap phage were used to generate Bluescript plasmids containing the fragment of TPO cDNA whose respective fusion proteins had been detected by the antisera. This procedure used the helper phase R408 according to the protocol of the manufacturer (Stratagene). Rescued phagemids were used to infect XL1-blue bacteria (Stratagene). Plasmids were prepared from individual colonies (Maniatis, T., et al., *Molecular Biology: A Laboratory Manual*, Cold Spring Harbor Laboratory, Cold Spring Harbor, N.Y. (1982)), and the sizes of the cDNA inserts were assessed by digestion with EcoRI. Nucleotide sequencing of selected plasmid cDNA inserts was performed by the dideoxynucleotide termination method (Sanger, F., et al., *Proc. Natl. Acad. Sci. USA* 74:5463–5467 (1977)). Nucleotide sequence analysis was performed using the software provided by Bionet.

RESULTS

Localization of the epitope for a monoclonal antibody against thyroid peroxidase. In order to define the epitope(s) for anti-TPO antibodies in patients with autoimmune thyroid disease, it was first necessary to determine the validity of the immunological screening of a hTPO cDNA fragment sub-library (Mehra, V., et al., *Proc. Natl. Acad. Sci. USA* 83:7013–7017 (1986)). For this purpose, a monoclonal antibody generated against the thyroid microsomal antigen (Portmann, L., et al., *J. Clin. Invest.* 81:1217–1224 (1988)) that had been used successfully in the past to clone this antigen from a Graves' thyroid cDNA library (Hirayu, H., et al., *J. Clin. Endocrinol. Metab.* 64:578–584 (1987)) was used. The new TPO cDNA fragment sublibrary constructed contained $3.8 \times 10^6$ recombinant clones, with an effective (correct orientation and reading frame) size one-sixth of this number. The insert sizes were confirmed to be in the 200–500 b.p. range.

Screening of this library with the anti-microsomal antigen monoclonal antibody yielded 6–12 positive plaques per 1,000 plaques screened. Fourteen positive clones were randomly chosen for partial nucleotide sequencing to delineate the position of their TPO cDNA inserts relative to the entire TPO gene. Twelve of the 14 clones had cDNA inserts of 160–350 b.p. Two clones (U and V) that had cDNA inserts slightly larger than the expected 500 b.p. maximum were found, upon nucleotide sequencing, to have double cDNA inserts. As an indication of the success of the procedure, all 14 clones recognized by the monoclonal antibody spanned the same region (746–1,150 b.p.) of the hTPO gene (Magnusson, R. P., et al., *Mol. Endocrinol.* 1:856–861 (1987)) (FIG. 18). The maximum region common to all clones, and therefore an indication of a common epitope, was between bases 881 and 927 (AA AAC CCA TGT TTT CCC ATA CAA CTC CCG GAG GAG GCC CGG CCG GCC) (SEQ ID NO: 12), corresponding to a derived amino acid sequence of only 15 residues (Asn Pro Cys Phe Pro Ile Gln Leu Pro Glu Glu Ala Arg Pro Ala) (SEQ ID NO: 5). Therefore, the epitope recognized by the monoclonal antibody lies within this 15 amino acid span.

Epitope(s) for the antimicrosomal/TPO antibodies in autoimmune thyroid disease. Approximately forty screenings of the same TPO cDNA fragment sub-library described above with sera from patients from Hashimoto's thyroiditis did not yield any positive clones. The modifications that were tried included: 1) the use of different host bacteria (BB4, XL1 blue and Y1090) in which to express the TPO fusion proteins; 2) variation in the antibody binding detection system, including the use of anti-human IgG antibody or protein A from different vendors, as well as different incubation times and temperatures; and 3) the use of thirteen different patients' sera with potent anti-TPO activity. The sera were tested in multiple ways: without bacterial pre-adsorption; following adsorption with bacterial lysate; or after affinity-purification with recombinant hTPO. As internal controls in the screening procedure, the monoclonal antibody always yielded the expected number of positive clones.

Quite surprisingly, it was not possible to detect the epitope expressed within the 86 amino acid C2 hTPO polypeptide fragment, as previously reported (Libert, F., et al., *EMBO J.* 6:4193–4196 (1987); Ludgate, M., et al., *J. Clin. Endocrinol. Metab.* 68:1091–1096 (1989)). Because of the possibility that the fragment library employed might lack the C2 region, C2 region presence was tested by PCR, using oligonucleotide primers complementary to each end of the C2 region. A fragment of the expected size (261 b.p.) was clearly detected. Further, by using this PCR-generated fragment as a probe to screen the library, it was determined that approximately 10% of the plaques in the library contain C2 sequence.

Because of these negative results with the Hashimoto's thyroiditis sera in the hTPO cDNA fragment library, these sera also were used to screen lambda-Zap Graves' thyroid libraries (both oligo-dT and random-primed), constructed as described previously (Kaufman, K. D., et al., *J. Clin. Invest.* 84:394–403 (1989)). The oligo-dT-primed library contains numerous full-length copies of TPO cDNA (3.1 kb), as was demonstrated by the ability to express enzymatically active, antigenically intact TPO, when such cDNA was subcloned from the phage vector into a eukaryotic expression plasmid, and stably-transfected into eukaryotic Chinese hamster ovary cells (Kaufman, K. D., et al., *J. Clin. Invest.* 84:394–403 (1989)). Despite this, no specific signal was detected in screening this lambda-Zap library with 13 potent Hashimoto's sera that strongly react immunologically with TPO expressed in eukaryotic cells (Kaufman, K. D., et al., *J. Clin. Invest.* 84:394–403 (1989)). Many strongly reacting plaques were observed in these screenings, in which plaques reacted with the second antibody (anti-human IgG) even in the absence of patients' serum. Similar findings were obtained in the past with a Graves' thyroid cDNA library in lambda gt11 (Hirayu, H., et al., *J. Clin. Endocrinol. Metab.* 64:578–584 (1987)). These clones may represent IgG present in B-lymphocytes in the Graves' thyroid gland from which the library was made.

A potential difficulty with protein expression in a full-length cDNA phage library is that stop codons in the 5'-untranslated region of the cDNA insert may interrupt the translation of the foreign protein, which is inserted downstream of the β-galactosidase portion of the fusion protein.

To eliminate this possibility, two additional approaches were attempted. The first was screening of a random-primed human thyroid cDNA lambda-ZAP library, constructed in the same manner as the oligo-dT primed library, with the exception that random primers, rather than oligo-dT, were used for first strand cDNA synthesis. This library contains cDNA clones with a bias against full-length cDNA copies. The second approach was to delete the 5'-untranslated region from the full-length hTPO cDNA clone in the Bluescript plasmid generated from the lambda-Zap clone (Kaufman, K. D., et al., *J. Clin. Invest.* 84:394–403 (1989)). This deletion was accomplished by digestion of this plasmid with XhoI, thereby releasing 154 b.p. of the 5'-end of hTPO cDNA, leaving the entire TPO protein (minus the signal peptide) remaining in reading frame with the β-galactosidase component of the Bluescript plasmid. This new plasmid construct was transfected into XL1-Blue host bacteria for fusion protein generation (Stratagene, San Diego, Calif.) and western blot analysis. Neither the random-primed library nor the XhoI deletion mutant generated a hTPO protein that could be recognized by Hashimoto's antisera, or with anti-TPO antibody affinity-purified from these sera using recombinant hTPO.

DISCUSSION

The present data provide the first definition, at a precise molecular level, of an epitope recognized by an antibody against a thyroid autoantigen. Previous studies using polyclonal or monoclonal antibodies against human thyroglobulin (Male, D. K., et al., *Immunol.* 54:419–426 (1985); Fukuma, N., et al., *Immunol.* 67:129–131 (1989)) or TPO (Libert, F., et al., *EMBO J.* 6:4193–4196 (1987); Ludgate, M., et al., *J. Clin. Endocrinol. Metab.* 68:1091–1096 (1989); Doble, N. D., et al., *Immunol.* 64:23–29 (1988); ; Laing, P., *J. Clin. Lab. Immunol.* 19:19–23 (1986); Kohno, Y., et al., *J. Clin. Endocrinol. Metab.* 68:766–773 (1989); Yokoyama, N., et al., *J. Clin. Endocrinol. Metab.* 68:766–773 (1989)) have suggested that these antibodies recognize different regions of the antigen, but no study has been able to localize an epitope to a region of the molecule as small as 15 amino acid residues in size. The minimum size of a B-cell (antibody-recognized) epitope is under discussion, but is believed to be on the order of 5–10 amino acid residues (Van Regenmortel, M. H. V., et al., *Immunol. Lett.* 17:95–108 (1988)). Therefore, the 15 residue span of the present invention is very close of the size of the epitope itself.

A remarkable finding in this example is the striking contrast between the positive results with the antimicrosomal/TPO monoclonal antibody, and the inability of naturally-occurring, disease-associated anti-TPO antibodies to recognize the 66–166 amino acid TPO fragments expressed in the library employed. Unlike more linear T-cell epitopes, naturally occurring B-cell epitopes may be more conformational, and subject to influence by the secondary or even tertiary structure of the molecule. Disulfide bonds and contiguity of loops of the folded protein that may be far distant in its linear structure, may contribute to the formation of a B-cell epitope. The present data suggest that the epitope(s) for the disease-associated anti-TPO antibodies are highly conformational.

EXAMPLE XIV

Further Determination of the β Cell Epitope on TPO

This example provides an important step in understanding the pathogenesis of Hashimoto's thyroiditis by defining the epitope recognized by antithyroid peroxidase (anti-TPO) antibodies. In Example XIII, a human TPO cDNA sublibrary was constructed expressing random fragments of the protein (each 66–166 amino acids in length) (Mehra, V., et al., *Proc. Natl. Acad. Sci. USA* 83:7013–7017 (1986)). However, serum from patients with Hashimoto's disease with high titers of anti-TPO antibodies failed to recognize any of these TPO protein fragments. In contrast, TPO fragments in this library were recognized by a mouse monoclonal antibody (MAb) against denatured human TPO. These data support previous evidence (Hamada, N., et al., *J. Clin. Endocrinol. Metab.* 64:230–238 (1987); Nakajima, Y., et al., *Mol. Cell. Endocrinol.* 53:15–23 (1987)) that the disease-associated TPO epitopes are highly conformational and are likely to be formed by noncontiguous (discontinuous) regions of the linear amino acid sequence.

This example presents the determination of the disease-associated B-cell epitopes on TPO, using a panel of 13 MAb generated against nondenatured human TPO (Ruf, J., et al., *Endocrinology* 125:1211–8 (1989)). The binding of some of these MAb to native TPO is inhibited by anti-TPO antibodies in the serum of patients with autoimmune thyroid disease (Ruf, J., et al., *Endocrinology* 125:1211–8 (1989)), indicating that these particular MAb epitopes correspond to or are in the vicinity of the disease-associated epitopes. Determination of the epitopes for some of the TPO MAb in the panel could, therefore, delineate molecular domains of the autoimmune thyroid disease-associated B-cell epitopes.

MATERIALS AND METHODS

TPO Fragment Library: The construction of the TPO random fragment cDNA library ($3.8 \times 10^6$ plaque-forming units) has been described previously. Immunoscreening of the library was performed by standard techniques, as previously described, using 13 mouse MAb generated against native human TPO (Ruf, J., et al., *Endocrinology* 125:1211–8 (1989)). Positive clones were plaque-purified and used to generate Bluescript plasmids for nucleotide sequencing of the cDNA inserts (Sanger, F., et al., *Proc. Natl. Acad. Sci. USA* 74:5463–5467 (1977)). The DNA sequences of independent clones were aligned with the TPO cDNA sequence to localize the minimum region of overlap that encompasses the epitope (Mehra, V., et al., *Proc. Natl. Acad. Sci. USA* 83:7013–7017 (1986)).

Western Blots: Recombinant human TPO stably expressed by Chinese hamster ovary cells was used as antigen. Cells were cultured, scraped into buffer containing 10 mM Tris (pH 7.4), 0.25 M sucrose, 2 mg/mL bacitracin, 1 mM phenylmethylsulfonyl-fluoride, 0.1 mM N-α-p-tosyl-L-lysine-chloromethylketone, and 0.1 mM leupeptin (all from Sigma Chemical Co., St. Louis, Mo.), and a microsomal fraction was prepared, all as previously described. The protein concentration was determined by the method of Bradford (Bradford, M. M., *Anal. Biochem.* 72:238–254 (1976)). Samples (~100 µg protein) were treated with 2% sodium dodecyl sulfate and 5% β-mercaptoethanol (final concentrations) and subjected to 7.5% polyacrylamide gel electrophoresis (Laemmli, U. K., *Nature* 227:680–685 (1970)). Proteins were transferred to a ProBlot membrane (Applied Biosystems, Foster City, Calif.) using the MilliBlot transfer system (Millipore Co., Bedford, Mass.) according to the manufacturer's recommendations. Membranes were processed as previously described, with minor modifications. Incubations with MAb (1:1000 dilution) were performed overnight at 4° C. MAb binding was detected with horseradish peroxidase-linked sheep antimouse immunoglobulin G F(ab')2 (Amersham International, Aylesbury, Buckinghamshire, United Kingdom) diluted 1:1,000 using 0.5 mg/mL 4-chloro-1-naphthol, 0.57 mg/mL imidazole, 17% methanol, and 0.42% hydrogen peroxide as substrate.

RESULTS

Of the 13 mouse MAbs generated against nondenatured human TPO (Ruf, J., et al., *Endocrinology* 125:1211–8 (1989)), only 1 (no. 47) recognized TPO protein fragments expressed by the cDNA library. The nucleotide sequences were determined for 18 randomly selected cDNA clones. All cDNA inserts spanned the same region of the TPO cDNA sequence (FIG. 19). The minimal region common to all cDNA fragments was between basepairs 2219 and 2247 of the human TPO cDNA nucleotide sequence, coding for 9 amino acids (residues 713–721) in the protein. These nine amino acids thus represent at least a part of the epitope for anti-TPO monoclonal antibody 47. The inability of the other 12 TPO MAb to recognize TPO peptide fragments expressed by the library could not be attributed to technical difficulties in the screening procedure, because internal controls, TPO MAb 47 and TPO MAb 20.10 (Portmann, L., et al., *J. Clin. Invest.* 81:1217–1224 (1988)) all were strongly positive.

To compare the reactivity of the panel of 13 MAb to TPO fragments generated by the cDNA library (see above) with reactivity to the entire TPO protein, Western blot analyses were performed using these MAb as probes and recombinant human TPO expressed in CHO cells as antigen. For the TPO fragments, only MAb 47 reacted with the entire TPO molecule under denaturating and reducing conditions (FIG. 20). As a control, TPO MAb 20.10 (Portmann, L., et al., *J. Clin. Invest.* 81:1217–1224 (1988)), generated against the denatured protein and previously shown to recognize a linear epitope between TPO amino acids 266–281 (Finke, R., et al., *J. Clin. Endocrinol. Metab.* 71:53–59 (1990)), also detected a protein of similar size. Consistent with previous enzyme-linked immunosorbent assay data (Ruf, J., et al., *Endocrinology* 125:1211–8 (1989)), all 13 MAb against native TPO immunoprecipitated nondenatured recombinant human TPO.

DISCUSSION

The present data demonstrate that only one (no. 47) of a panel of 13 MAb generated against native human TPO reacts with random 66–166 amino acid fragments of the 933-amino acid TPO molecule. Consistent with this observation, only MAb 47 recognizes intact TPO after denaturation and reduction, although all 13 MAb in this panel recognize native nondenatured human TPO (Ruf, J., et al., *Endocrinology* 125:1211–8 (1989)). In agreement with our findings, MAb 47 is unique in this panel of TPO Mab, in that it was the only MAb whose binding to TPO could not be abolished by dithiothreitol treatment of the protein. The epitope for TPO MAb 47 (amino acids 713–721) is different from that for TPO MAb 20.10 (amino acids 266–281). Furthermore, TPO MAb 20.10 reacts only with denatured TPO (Portmann, L., et al., *J. Clin. Invest.* 81:1217–1224 (1988)).

Our findings reinforce the emerging concept that many B-cell epitopes are conformational and are likely to be discontinuous. By this it is meant that epitopes on globular proteins are dependent on 3-dimensional structure and consist of a number of different regions of the linear protein brought into apposition by protein folding. Thus, only 1 of 13 MAb generated by immunizing mice with native TPO recognizes a linear epitope expressed in a TPO fragment library or after unfolding of TPO by denaturation and reduction. Because MAb 47 also recognizes the native TPO protein, amino acids 713–721 must be situated on the surface of human TPO (unlike amino acids 266–281 recognized by TPO MAb 20.10). Other contiguous loops in the folded protein derived from different regions of the linear sequence may also contribute to the epitope for MAb 47. Amino acids 713–721 may be the minimum needed for recognition by the antibody.

The binding of TPO MAb 47 to human TPO is inhibited by anti-TPO antibodies in the serum of patients with autoimmune thyroid disease (Ruf, J., et al., *Endocrinology* 125:1211–8 (1989)). Therefore, the linear nine-amino acid (residues 713–721) epitope for MAb 47 either corresponds or is close to an autoantibody-associated TPO B-cell epitope. The present data define specific amino acids in a domain containing an epitope for thyroid autoantibodies. Competition studies with MAb 47 (Ruf, J., et al., *Endocrinology* 125:1211–8 (1989)) suggest that the idiotypic antibody in autoimmune thyroid disease serum that interacts with the MAb 47 epitope is uncommon.

EXAMPLE XV

Overexpression of Secreted hTPO in Non-Thyroidal Eukaryotic Cells

Previous examples describe expression of recombinant human TPO (hTPO) as both the native, membrane-associated enzyme and as a truncated, secreted protein. In the present example, the overexpression of the secreted form of recombination hTPO in eukaryotic cells is described. hTPO gene amplification was accomplished with a vector containing the mouse dihydrofolate reductase (dhfr) gene. Stably transfected Chinese hamster ovary (CHO) cells were grown in the presence of progressively increasing concentrations of methotrexate (MTX). TPO expression was measured immunologically in an enzyme-linked immunosorbant assay (ELISA) using anti-TPO antibodies. Attempts to also overexpress the wild-type, membrane-associated form of the enzyme were less successful. While some amplification of the native hTPO gene was observed, it was not possible to achieve a level of protein expression significantly higher than that observed in some high-producing cell lines prior to initiation of selective pressure by MTX. Indeed, above 100 nM MTX, the immunoreactive hTPO content of cells actually diminished. In contrast, progressive overexpression of the truncated, secreted form of hTPO up to a final MTX concentration of 10,000 nM was observed. Slot-blot analysis of genomic DNA from transfected cells revealed parallel amplification of the dhfr and truncated hTPO genes. High-level expression of secreted hTPO provides a means by which large amounts of biologically and immunologically active hTPO protein may be obtained.

MATERIALS AND METHODS

Construction of the expression plasmids pSV2-DHFR-ECE-hTPO and pSV2-DHFR-ECE-hTPO-M1: Full-length hTPO cDNA in the expression vector pECE was digested with PvuI and the ends blunted with the Klenow fragment of DNA polymerase I. The expression vector pSV2-dhfr (kindly provided by Dr. Gordon Ringold, Syntex, Palo Alto, Calif.) was digested with EcoRI, the ends blunted with Klenow fragment of DNA polymerase I, and the vector treated with bacterial alkaline phosphatase. The blunt-ended, linearized vector and cDNA were ligated together to form the recombinant plasmid pSV2-DHFR-ECE-HTPO. The cDNA coding for the secreted form of hTPO (hTPO-M1), generated in Bluescript by site-directed mutagenesis, was exchanged for wild-type hTPO cDNA in the plasmid pSV2-DHFR-ECE-HTPO to generate pSV2-DHFR-ECE-HTPO-M1.

Transfection of pSV2-DHFR-ECE-HTPO and pSV2-DHFR-ECE-HTPO-M1 into CHO dhfr- cells and amplification with methotrexate: CHO dhfr- cells (CHO-DG44; kindly provided by Dr. Robert Schimke, Stanford University, Palo Alto, Calif.) were maintained in Ham's F-12 medium supplemented with 10% fetal calf serum, penicillin (100 U/ml), gentamicin (40 ug/ml) and amphotericin B (2.5 ug/ml). Transfection with plasmid DNA (10 ug) was performed by the calcium phosphate precipitation method (Chen, C., et al., *Mol. Cell. Biol.* 7:2745–2752 (1987)). Transfected cells were selected for in thymidine-guanidine-, and hyposanthine-free Ham's F-12 medium supplemented with 10% dialyzed fetal calf serum and antibiotics as above. Individual clones were selected with cloning cylinders and 2 clones with high levels of TPO expression (clones CHO-HTPO-2B and CHO-HTPO-C4C) were subsequently used for amplification. Methotrexate (MTX) was added to this selective cell culture medium as an initial concentration of 3.3 nM and surviving cells were harvested and expanded. The methotrexate concentration was sequentially increased by 3.33-fold increments until a final concentration of 10,000 nm (100 μM) was reached.

ELISA of CHO-hTPO and CHO-hTPO-M1 cells: ELISA of human sera (kindly provided by Dr. Sandra McLachlan, Cardiff, Wales, UK) of control and MTX-treated CHO-hTPO cells was modified from the method of Schardt et al., (*J. Immunol. Methods* 55:155–168 (1982)), as described above, using cellular microsomes. Because the hTPO-M1 protein is secreted into the medium of CHO-hTPO-M1 cells, three-day conditioned media were collected from these cells. Proteins from these media were precipitated and treated, as described above. Antigen for ELISA of human sera was applied as 100 ul of the dialyzed protein precipitate per well, approximately 300 ug protein diluted 1:1 in 2× coating buffer (0.1 M sodium bicarbonate, pH 9.3+0.04% sodium azide). Because more than one ELISA was used for all MTX concentrations, values are reported as an ELISA index referenced to 1000 nM MTX values used across assays of each cell type. The same sera were used in ELISAs of each cell type.

Genomic DNA extraction of CHO-hTPO-M1 cells: Cells from confluent 100 mm diameter dishes of CHO-hTPO-M1 cells surviving at each MTX concentration were frozen and kept at −80° C. until replated (100 mm dish), grown to confluence, and used for extraction of genomic DNA. Cells were rinsed three times in 5 ml ice-cold Dulbecco's phosphate-buffered saline, calcium- and magnesium-free (PBS-CMF). The cells were then scraped from the dish, recovered by centrifugation for 10 minutes at 2000 rpm, 4° C. The pellet was resuspended in 2 volumes (100–200 ul) 320 mM sucrose, 10 mM Tris-Cl, pH 7.5, 5 mM $MgCl_2$, 1% Triton X-100, and kept on ice for 30 minutes. The suspension was centrifuged for 15 minutes at 2500 rpm (4° C.), and the pellet resuspended in 4.5 ml 10 mM NaCl, 10 mM Tris-Cl, pH 7.5, 10 mM EDTA. RNAse digestion (addition of 4.5 μl 10 mg/ml DNase-free RNase for 60 min at room temperature) was followed by proteinase K digestion overnight at 37° C. (addition of 0.5 ml 10% SDS+0.1 ml 10 mg/ml proteinase K). The DNA was then extracted two or three times (until the aqueous phase was clear) with 5 ml 0.1 M Tris-buffered phenol, pH 7.4:$CHCl_3$, 4% isoamyl alcohol (1:1), followed by an equal volume extraction with $CHCl_3$, 4% isoamyl alcohol. The DNA was precipitated with 0.1 volume 3 M sodium acetate, pH 5.2 and 2 volumes ethanol at −80° C. for 2 hours and the pellet resuspended in 0.5 ml TE (10 mM Tris, pH 8.0, 1 mM EDTA). Quality and quantity of genomic DNA samples were assessed by agarose gel electrophoresis and OD at 260 nm. Genomic DNA yield from a 100 mm dish of confluent cells was 40–160 μg.

Slot blot analysis of CHO-hTPO-M1 cells: Genomic DNA (15 ug) from CHO-hTPO-M1 cells was digested with EcoRI, ethanol-precipitated, resuspended in TE buffer, and requantified by OD at 260 nm. Aliquots of this DNA (1.0, 0.5, and 0.25 ug) were diluted in 0.5 ml 0.4 N NaOH, 10 mM EDTA, boiled for 10 minutes and placed on ice. Nylon membrane filters (Hybond-N RPN, 3050N, Amersham Corporation, Arlington Heights, Ill.), rinsed in 0.4 N NaOH, were applied to a slot-blot apparatus (Minifold II, Schleicher & Schuell, Keene, N.H.) and the wells were rinsed with 0.5 ml 0.4 N NaOH and vacuum dried. Individual 0.5 ml genomic DNA samples were added per well, vacuum was applied briefly, and the wells were rinsed with 0.5 ml 0.4 N NaOH and vacuum dried. The filters were removed, washed briefly in 2× SSC (0.3 M NaCl, 0.03 M sodium citrate, pH 7.0) and air dried. Genomic DNA was cross-linked to the filters by UV irradiation (UV Stratalinker 2400, Stratagene, La Jolla, Calif.), and the filters probed with a labeled, PCR-derived, 0.3 kb fragment of the mouse dhfr cDNA washed, and atuoradiograms performed. Following confirmed removal of first label after boiling in 0.1× SSC (0.015 M NaCl, 0.0015 M sodium citrate), 0.1% SDS for 1 hour, the filters were reprobed with a labeled 0.56 kb fragment of human TPO cDNA, washed, and photographed.

RESULTS

Recombinant plasmids pSV2-dhfr-ece-hTPO and pSV2-dhfr-ece-hTPO-M1 were transfected into CHO dhfr- cells to produce CHO-TPO and CHO-TPO-M1 cell lines, respectively. These cell lines were grown in progressively increasing (3.33 fold) MTX concentrations up to 1000 (membrane-associated hTPO) or 10,000 (secreted hTPO), each cycle taking a minimum of three weeks. Cells at each stage of amplification were cryo-preserved and were replated after the final amplification step for comparison of the levels of immunoreactive hTPO expression.

Content of wild type membrane-associated human TPO in microsomal fractions from cell lines CHO-HTPO-25 and CHO-HTPO-C4C was quantitated immunologically by ELISA using anti-TPO antibodies in Hashimato's thyroiditis serum. In both cell lines, some degree of amplification of TPO immunoreactivity was evident with increasing MTX concentrations, reaching a maximum at 100 nm MTX. This increase was followed by a gradual fall in immunoreactive TPO protein at higher MTX concentrations up to 1 uM. There was a minimal increase of TPO expression in CHO-HTPO-C4C, the cell line with the higher basal (pre-MTX) hTPO content. While there was a greater increment in TPO expression in CHO-HTPO-2B cells, the maximum level achieved was only slightly higher than that in the CHO-HTPO-C4C cells. During MTX-induced gene amplification of both the CHO-HTPO and CHO-HTPO-M1 cells, there appeared to be greater cell death at the 100 to 333 nM MTX step than at lower concentrations, with a delay in growth of surviving cells to confluence.

In contrast to the limited overexpression of TPO with the membrane-associated form of the enzyme, overexpression of the secreted form of hTPO by CHO-HTPO-M1 cells was much greater. In these cells, most of the TPO is secreted into the medium, with little remaining in the cells. TPO expression increased markedly over baseline beginning at 333 nM MTX, with progressive increments up to the highest concentration of used (10 uM). Slot-blot analysis of genomic DNA from CHO-HTPO-M1 cells using either a dhfr or hTPO DNA probe revealed similar amplification patterns parallel to that of the pattern of TPO protein expression.

A comparison was made of the amount of TPO available from the membrane-associated (CHO-HTPO-2B cells) and secreted protein (CHO-HTPO-M1 cells) for immunological detection in an ELISA. Three-day conditioned media from a single 100 mm dish of confluent CHO-HTPO-M1 cells (10 um MTX) yielded significantly more TPO protein than did microsomes prepared from a 100 mm confluent dish of CHO-HTPO-2B cells (100 nM MTX). Both of these cell lines represented their highest levels of TPO expression.

EXAMPLE XVI

The Role of Carbohydrate Moieties in Recognition of TPO by Anti-TPO Antibodies in Hashimoto's Thyroiditis Carbohydrate moieties on hTPO may contribute to the epitopes recognized by anti-hTPO antibodies in Hashimoto's thyroiditis. This is because bacterial fusion proteins unlike proteins expressed in eukaryotic cells, are not glycosylated. Very little is known about the carbohydrate moieties in hTPO. Human TPO (Ruf, J., et al., *Acta Endocrinal, Suppl.* 281:49–56 (1987)) and the microsomal antigen (Kajita, Y., et al., FEBS Lett. 187:334–338 (1985)) are bound to the lectin concanavalin A. The latter is also partially bound to lentil lectin (Kajita, Y., et al., *FEBS Lett.* 187:334–338 (1985)). It is unknown whether the hTPO carbohydrate structures are N-linked, O-linked, or both. In the present example, the nature of the carbohydrate components of hTPO was examined, and whether or not hTPO carbohydrate plays a role in the structure of naturally occurring epitopes in Hashimoto's thyroiditis.

METHODS AND MATERIALS

Cell culture, protein radiolabeling and hTPO immunoprecipitation: Chinese hamster ovary (CHO) cells stably expressing human hTPO (CHO-TPO 12 g) (Kaufman, K. D., et al., *J. Clin. Invest.* 84:394–403 (1989)) were cultured in 100 mm diameter dishes in F12 medium containing 10% fetal calf serum, 100 U/ml penicillin, 40 µg/ml gentamicin and 2.5 µg/ml amphotericin B. For radiolabeling, subconfluent cells were rinsed twice in phosphate-buffered saline without calcium and magnesium (PBS-CMF), and were then incubated for 15–20 minutes in methionine-free F12 medium (3 ml/dish) containing 10% dialyzed fetal calf serum. $^{35}$S-methionine (<1100 Ci/mmol; Amersham, Arlington Heights, Ill.) was then added to the medium (0.2 mCi/ml), and the incubation was continued for 2–4 hours at 37° C. The medium was removed and the cells were rinsed twice in PBS-CMF, scraped into ice-cold PBS-CMF, pelleted for 10 minutes at 1000× g (4° C.), washed once in 10 ml of the same buffer, and the cell pellet resuspended (0.3 ml/dish of cells) in homogenization buffer (50 mM Hepes, pH 7.5, 1% Triton X-100, 0.1 mM phenylmethylsulfonyl fluoride, 2 mg/ml bacitracin, 0.25 mM TLCK (N-p-tosyl-1-lysine chloro-methyl ketone) and 0.1 mM leupeptin (Sigma Chemical Co., St. Louis, Mo.). After shaking for 1 hour at room temperature, the mixture was centrifuged for 1 hour at 100,000× g (4° C.), and the supernatant was diluted to 1 ml in immunoprecipitation buffer (10 mM Na phosphate, pH 7.2, 1 M NaCl, 0.1% Na dodecylsulfate, 0.5% NP-40 and 2 mM EDTA).

The 1 ml of solubilized cellular proteins was pre-adsorbed twice for 10 minutes at room temperature with 80 ul of 10% IgG-Sorb (Staphylococcus A) (The Enzyme Center, Malden, Mass.), followed by removal of the IgG-Sorb by centrifugation for 3 minutes at 10,000× g in a microfuge. Hashimoto's thyroiditis sera with high titers (ELISA readings >1.5 O.D. units) of anti-hTPO antibodies were added to a final dilution of 1:200. Similar results were obtained with three separate sera. After incubation overnight at 4° C., 150 µl of IgG-Sorb were added, and the tubes rotated end over end for 2–4 hours at room temperature. The IgG-Sorb was recovered by centrifugation for 5 minutes at 10,000× g, washed 5 times with 1 ml of immunoprecipitation buffer, and then once with 10 mM Tris, pH 7.5, 2 mM EDTA and 0.5% Na dodecylsufate. Finally, the pellet was resuspended in Laemmli sample buffer (31), with 50 mM dithiothreitol (DTT), boiled for 3 minutes, and applied to 6% polyacrylamide gels. Molecular weight markers (Sigma; St. Louis, Mo.) were as follows: 205 kD myosin; 116 kD β-galactosidase; 97 kD phosphorylase b; 66 kD bovine serum albumin; 45 kD ovalbumin. Autoradiography was performed with Kodak XAR-5 film.

Enzymatic deglycosylation of immunoprecipitated human TPO: Recombinant, radiolabeled hTPO, immunoprecipitated and bound to IgG-Sorb, as described above, was recovered in enzymatic digestion buffers rather than in Laemmli sample buffer. Enzymatic digestions (18 hours at 37° C.) were as follows: endoglycanase F (Boehringer-Mannheim, West Germany, 30 U/ml; in 100 mM Na phosphate buffer, pH 6.0, 50 mM EDTA, 0.1T SDS, 1% beta-mercaptoethanol and 1% NP40); endoglycanase H (Boehringer, 0.2 U/ml; in the same buffer as for endo F, except that EDTA was omitted); O-glycanase (Boehringer, 2.5 U/ml; same buffer as for endo H); and neuraminidase (Sigma, 1 U/ml; in 100 mM Na acetate, pH 5.2, 5 mM EDTA and 1% β-mercaptoethanol). As a control, to monitor degradation of the hTPO, each experiment included a sample incubated in parallel without added enzyme.

Lectin affinity chromatography: Detergent extracts of CHO-TPO cells (5–7 100 mm diameter dishes) were radiolabeled with $^{35}$S-methionine (see above) and applied to 2 ml bed volume columns of Concanavalin A (Con A), peanut agglutinin (PNA), wheat germ agglutinin (WGA), Ricinus communis agglutin 1 (RCA1) and Ulex Europaeus (UEA-F) agarose-bound lectins (all purchased from Vector Laboratories, Burlingame, Calf.). For application to the columns, samples (0.3 ml) were diluted to 10 ml in Buffer A (20 mM Tris HCl, pH 7.4, 150 mM NaCl, 0.1% Triton X-100), supplemented with the following for each individual lectin: WGA and RCA1- 1 mM EDTA; Con A-1 mM CaCl$_2$, 1 mM MnCl$_2$; PNA-1 mM CaCl$_2$, 1 mM MgCl$_2$; UEA-F-1 mM CaCl$_2$. After application to the columns, the unbound proteins were removed by washing with 50 ml of the foregoing Buffer A's. Specifically adsorbed proteins were eluted with 25 ml of the following (all of 300 mM):- WGA, N-acetylglucosamine; PNA and RCA1, D-galactose; Con A, α-methyl-D-mannoside; and UEA-F, α-fucose. Fractions of 0.5 ml were collected and counted for radioactivity in a liquid scintillation counter. The two fractions containing the peak of the eluted radioactivity were pooled (1 ml) and subjected to immunoprecipitation with anti-hTPO antibodies in the sera of patients with Hashimoto's thyroiditis, followed by polyacrylamide electrophoresis and autoradiography (see above).

RESULTS

As described above, the derived amino acid sequence of human TPO (Magnusson, R. P., et al., *Mol. Endocrinol,* 1:856–861 (1987); Kimura, S., et al., *Proc. Natl. Acad, Sci. USA* 84:5555–5559 (1987); Libert, F., et al., *Nucl. Acids Res.* 15:6735 (1987)) suggests that there are 5 potential glycosylation sites in the extracellular domain of the enzyme. This is based on the tri-peptide algorithm for glycosylation sites of Asn-X-Ser/Thr (X refers to any amino acid; the third position can be either Ser or Thr). Carbohydrate chains can be linked to the Asn residue (N-linked), or to the Ser or Thr residues (O-linked).

To determine whether hTPO carbohydrate moieties were N-linked, O-linked, or both, and also to obtain information about the characteristics of the carbohydrate component(s), hTPO was digested with a number of deglycosylating enzymes of varying specificity. To prepare radiolabeled hTPO, proteins in Chinese hamster ovary (CHO) cells expressing recombinant hTPO were radiolabeled with $^{35}$S-methionine, followed by immunoprecipitation with anti-hTPO antibodies present in the serum of patients with Hasimoto's thyroiditis. As observed previously on western blot analysis (Kaufman, K. D. et al., *J. Clin. Invest.* 84:394–403 (1989)), recombinant hTPO was present as a doublet of approximately 115 kD and 110 kD, with the relative dominance of the 115 kD and the 110 kb bands varying from experiment to experiment. Digestion with endoglycosidase (endo) F, which removes both complex and polymannose (Thotakura, N. R., et al., *Meth. Enzymol.* 138:350–359 (1987)) N-linked glycans by cleaving the glycosidic linkage between the two N-acetyl glucosamine (GlcNac) residues in the chitobiose core, increased the electrophoretic mobility of the hTPO doublet to approximately 110 kD and 105 kD. Endo H, which acts similarly to endo F on polymannose but differently from endo F on complex glycans, also converted the mobility of hTPO to a 110 kD and 105 kD doublet. In contrast, O-glycanase and neuraminidase, which remove O-linked glycans and terminal neuraminic acid, respectively, did not alter the mobility of radiolabeled hTPO. These data suggest that human TPO contains only polymannose N-linked glycans.

Lectin affinity chromatography (Merkle, R. K., et al., *Meth. Enzymol,* 138:232–259 (1987)) provided further support for the polymannose nature of the hTPO carbohydrate moieties. Thus, radiolabeled, recombinant hTPO was retained only on concanavalin A-Sepharose, which bonds with high affinity to N-linked oligosaccharides in which at least two outer mannose residues are either unsubstituted, or are substituted only at position C-2 by another sugar. Bound hTPO could be eluted with 300 mM α-methyl-D-mannoside. TPO did not bind to wheat germ agglutinin (specificity for terminal and internal GlcNac and terminal neuraminic acid), Ricinus communis agglutinin 1 (RCA1) (highest affinity for bi- and tri-antennary N-linked oligosaccharides with terminal galactose residues), peanut agglutinin (terminal Gal-β-1,3-GalNac) or Ulex europaeus (terminal α-L-fucose).

Having determined the type of carbohydrate present in recombinant human TPO, the inventor investigated whether these residues play a role in the disease-associated epitopes on hTPO that are recognized by anti-hTPO antibodies in Hashimoto's thyroiditis.

Radiolabeled recombinant hTPO was first partially purified by concanavalin A-Sepharose affinity chromatography, next digested with three different glycanases, and finally subjected to immunoprecipitation with anti-hTPO antibody in Hashimoto's thyroiditis serum. Complete removal of the N-linked carbohydrate chains distal to the chitobiose core with endo F and endo H did not prevent antibody binding. In view of the complexity of these experiments, it is important to note the completeness of N-glycanase treatment. Thus, after deglycosylation, all of the hTPO immunoprecipitated was as the smaller (110 kD and 105 kD) doublet. As a further control, digestion with O-glycanase led to the immunoprecipitation of an unaltered hTPO form (115 kD and 110 kD).

DISCUSSION

Previous studies have shown that the thyroid microsomal antigen (Kajita, Y., et al., *FEBS Lett.* 187:334–338 (1985)) and immunopurified, non-recombinant human TPO (Ruf, J., et al., *Acta Endocrinol, Suppl.* 281:49–56 (1987)) are bound by concanavalin A. However, the present inventor is not aware of other data on the nature of the oligosaccharide (glycan) moieties in human TPO. By taking advantage of the expression of recombinant human TPO in non-thyroidal eukaryotic cells as described hereinabove, the present data provide new information on this subject.

Thus, by both glycan enzymatic digestion and by differential lectin affinity chromatography, the data presented in this example provide strong evidence that all the carbohydrate moieties on hTPO are linked to Asn residues (N-linked) and not to Ser or Thr (O-linked). Furthermore, the selective deglycosylation with endo H (Thotakura, N. R., et al., *Meth. Enzymol,* 138:350–359 (1987)), as well as the selective adsorption to concanavalin A (Merkle, R. K., et al., *Meth. Enzymol.* 138:232–259 (1987)), suggests that these N-linked oligosaccharides are of the polymannose variety.

Most important from the perspective of the pathogenesis of Hashimoto's thyroiditis, the present data indicate that the oligosaccharides present in hTPO do not significantly influence the epitopes recognized by anti-hTPO antibodies in the sera of patients with autoimmune thyroid disease, primarily Hashimoto's thyroiditis.

An assumption inherent in the present example is that the glycan components of recombinant hTPO are structurally the same as those in TPO present in human thyroid cells in vivo. While it cannot be excluded that Chinese hamster ovary cells may glycosylate the hTPO polypeptide chain in a manner different from human thyroid cells, it is likely that any such differences would be minor. Thus, unlike the polypeptide glycosylation pattern in yeast and bacteria, glycosylation in eukaryotic Chinese hamster ovary cells would be very similar, if not identical, to that in human thyroid cells. Further support for this assumption is that recombinant hTPO in Chinese hamster ovary cells is functionally active, at the same level present in human thyroid cells in monolayer culture (Kaufman, K. D., et al., *J. Clin. Invest.* 84:394–403 (1989)). In addition, virtually all sera from patients with Hashimoto's thyroiditis that contain anti-microsomal antibodies can recognize this form of recombinant human TPO on western blot analysis (Kaufman, K. D., et al., *J. Clin. Invest.* 84:394–403 (1989)) or by ELISA. Thus, by definition, the recombinant human TPO of the present invention contains the relevant, disease-associated epitopes on hTPO.

The present findings that removal of the carbohydrate moieties on human TPO does not affect the antigenicity of the molecule with respect to recognition by anti-hTPO antibodies in Hashimoto's thyroiditis serum are consistent with data obtained with tunicamycin (see Example XI). However, the present data are much stronger.

The present data suggest that oligosaccharide components in hTPO are not part of the "natural" epitopes recognized by anti-hTPO antibodies in the sera of patients with autoimmune thyroiditis. However, it remains possible that the glycosylated portion of the molecule could influence the interaction of the antibody with its epitope(s), such as by altering the affinity of this interaction. Although not intending to be bound by any particular theory, there is increasing recognition that the majority of epitopes recognized by both polyclonal and monoclonal antibodies are discontinuous. That is, by folding of the polypeptide chain, the three-dimensional structure of a protein may bring into apposition, as an epitope, widely separated, "discontinuous" regions of the polypeptide chain. This three-dimensional configuration may be lacking in peptide fragments, or may be altered by the β-galactosidase component of the bacterial fusion protein.

The present data relate to the recognition of epitopes on TPO by antibodies (B-cell epitopes). These B-cell epitopes are now recognized to be distinct from epitopes presented to T-cells in a major histocompatibility antigen (MHC) restricted manner (Livingstone, A. M., et al., *Ann. Rev. Immunol*, 5:477–501 (1987)). B-cell epitopes are likely to be important in mediating damage by the immune system to the thyroid gland, while T-cell epitopes are likely to be relatively more important in the initiation of the autoimmune process.

EXAMPLE XVII

Identification and Sequencing of β-Cell Region Capable of Binding β-Cell Epitope on Thyroid Peroxidase The sequences disclosed by the invention in, inter alia, Examples XIII and XIV provide for a method of identifying the interaction responsible for the β-cell recognition of thyroid peroxidase.

In detail, using the sequences disclosed in Examples XIII and XIV of the preferred embodiments, it is possible to isolate the proteins which bind to these sequences. This is accomplished using methods, well known in the art, of purifying a protein which binds to a specific DNA sequence. Preferably, a protein which binds to a specific DNA sequence is purified using affinity chromatography. Specifically, the nine amino acid sequence corresponding to residues 713–721 of thyroid peroxidase is immobilized on an appropriate matrix, such as Sepharose, and used as an affinity matrix to purify the proteins which bind to the particular sequence (Arcangioli B., et al., *Eur. J. Biochem.* 179:359–364 (1989)).

Preferably, the DNA binding protein is extracted from human β cells. The protein extract, obtained from the β cell, is applied to a column which contains the immobilized DNA sequence of interest. Proteins which are not capable of binding to the DNA sequence are washed off the column. Proteins which bind to the DNA sequence are removed from the column using a salt gradient. The proteins eluted from such a column are enriched for the proteins which bind to the specific DNA sequences immobilized on the matrix. The DNA binding protein is further purified using procedures well known in the art, such as ion exchange chromatography, high performance liquid chromatography, size exclusion chromatography, and the like.

During the purification of the DNA binding protein, the protein is assayed, for example, using the well known gel retardation assay (Garner, M. M. et al., *Nucl. Acid Res.* 9:3047 (1981); Fried, M. et al., *Nucl. Acid Res.* 9:6506 (1981)), or other well known methods.

Once the DNA binding protein is purified, a partial amino acid sequence is obtained from the N-terminal of the protein. Alternatively, the protein is tryptically mapped and the amino acid sequence at one of the fragments is determined by methods known in the art.

The deduced amino acid sequence is used to generate an oligonucleotide probe. The encoding sequence can be based on codons which are known to be more frequently used by the organism. Alternatively, the probe can consist of a mixture of all the possible codon combination which could encode the polypeptide. Such methods are well known in the art.

A probe complementary to the amino acid sequence is used to screen either a cDNA or genomic library for the genomic sequences which encode the DNA binding protein. Once the gene encoding the DNA binding protein has been obtained, the sequence of the DNA is determined according to well known methods. The gene can be used to obtain large amounts of the protein from a recombinant host, or the sequence can be used in mutational analysis to further define the functional regions within the protein which interacts with the DNA.

Alternatively, proteins which bind to β-cell epitope (residues 713–712) are isolated by identifying a clone expressing the protein using well known techniques such as Southwestern blotting (Sharp, Z. D. et al., *Biochim Biophys Acta*, 1048:306–309 (1990); Gunther, C. V. et al., *Genes Dev.* 4:667–679 (1990); and Walker, M. D. et al., *Nucleic Acids Res.* 18:1159–1166 (1990)).

In a Southwestern blot, a labeled DNA sequence is used to screen a cDNA expression library whose expressed proteins have been immobilized on a filter via colony or plaque transfer. The labeled DNA sequences bind to colonies or plaques which express a protein capable of binding to the particular DNA sequence. Clones expressing a protein which bind to the labeled DNA sequence are purified and the cDNA insert which encodes the DNA binding protein is isolated and sequenced. The isolated DNA can be used to express large amounts of the protein for further purification and study, used in isolating the genomic sequences corresponding to the cDNA, or used to generate functional derivative of the binding protein.

The present invention is thus directed to DNA binding proteins which can bind to the β-cell epitope and to functional derivatives thereof.

EXAMPLE XVIII

Cloning of a Human Fab Fragment Specific for Human Thyroid Peroxidase

IgG autoantibodies to thyroid peroxidase (TPO) are characteristics of patients with Graves' and Hashimoto's diseases and are implicated in autoimmune thyroid destruction (reviewed in DeGroot, L. J., and Quintans, J., *Endocr.Rev.* VOL.10:537–562 (1989)). The availability of monoclonal human TPO autoantibodies of the same class and high affinity as those present in serum would contribute significantly towards an understanding of the pathogenesis of these common autoimmune diseases. Unfortunately, despite numerous attempts using EB virus infection and/or cell fusion, only one cell line secreting IgG class human autoantibody to TPO has been produced, and this human-mouse hybridoma was unstable (Fukuma, N., Sarsero, D., Furmaniak, J., Pegg, C.A.S., McLachin, S. M., and Rees Smith, B., "B and T cell epitopes on thyroid peroxidase," (P. Carayon and J. Ruf, eds.), *Colloque INSERM/John Libbey Eurotext Ltd.* 195–201 (1990)).

Recently a technique has been described for cloning heavy and light chain gene fragments in a bacteriophage expression library (Huse, W. D., Sastry, L., Iverson, S. A., Kang, A. S., Alting-Mees, M., Burton, D. R., Benkovic, S. J., and Lerner, R. A. *Science* VOL. 246:1275–1281 (1989)). In the present example the use of this approach to clone a human Fab fragment specific for human TPO is described.

MATERIALS AND METHODS

Construction of combinatorial H and L gene libraries: A cDNA library from the thyroid gland of a patient with Graves' disease, as described in Example I, was used as a source of cDNA coding for thyroid autoantibodies. The presence of thyroid autoantibody mRNA in this gland was previously suspected for two reasons. First, infiltrating thyroid lymphocytes are a major source of thyroid autoantibodies (McLachlan, S. M., McGregor, A., Rees Smith, B., and Hall, R. *Lancet* VOL.i:162–163 (1979); Atherton, M. C.

McLachlan, S. M., Pegg, C.A.S.., Dickinson, A., Baylis, P., Young, E. T., Proctor, S. J., and Rees Smith, B. *Immunology* VOL.55:271–279 (1985)). Second, proteins expressed by this library were recognized by antiserum to human IgG. A combinatorial library of heavy (H) chain fragments and kappa light chain genes was produced using oligonucleotides and vector in the Immunozap Cloning Kit (Stratacyte, La Jolla, Calif.). Bacteriophage DNA (Maniatis, T., Fritsch, E. F., and Sambrook, J. Cold Spring Harbor Laboratory, N.Y. (1982)) prepared from the Graves' thyroid cDNA library was used as template in the polymerase chain reaction (Saiki, R. K., Gelfand, D. N., Stoffel, S., Scharf, S. J., Higuchi, R., Horn, G. T., Mullis, K. B., and Erlich, H. A. *Science* VOL.239:487–491 (1988)). Heavy chain gene sequences were amplified in separate reactions using 4 different forward oligonucleotide primers corresponding to the relatively conserved amino terminus of the molecule and a reverse primer to the CH1 domain-hinge junction of IgG1. Kappa light chain genes were amplified using primers complementary to the sequence coding for the signal peptide/kappa light (L) chain junction and the carboxyl terminus. The combinatorial library was constructed according to the protocol of Stratacyte.

Screening for TPO binding: The unamplified combinatorial library was screened to XL1-Blue cells by conventional techniques (Maniatis et al., supra) using highly-purified, secreted recombinant human TPO, prepared as described above, labelled with $^{125}$I by the iodogen method (Salacinski, P. R. P., McLean, C., Sykes, J. E. C., Clement-Jones, V. V., and Lowry, P. J. *Anal.Biochem.* VOL.117:136–146 (1981)) to a specific activity of 10 uCi/ug. A plaque expressing a Fab fragment that bound radiolabeled TPO was identified by autoradiography and was cloned to homogeneity. The affinity of this TPO antibody was measured in a confluent plaque lysis assay (~100 plaques per spot) by the addition of unlabeled TPO ($10^{-10}$ M–$10^{-6}$ M) to the $^{125}$I-labeled TPO. Densitometry was performed (Biorad 620 videodensitometer) on duplicate spots at each TPO concentration and expressed as arbitrary OD (optical density) units.

Nucleic acid sequencing of H and L genes coding for human TPO specific Fab fragment: The nucleotide sequence of the cDNA of the TPO-positive clone (SP2) was determined (Sanger, F., Nicklen, S., and Coulson. A. R. *Proc. Natl. Acad. Sci. USA* VOL.74:5463–5467 (1977)) in both directions following its recovery in Bluescript using the helper phage R408 (Stratacyte).

RESULTS

Screening ~$2\times10^5$ plaques yielded one (SP2) that bound radiolabeled TPO. After cloning to homogeneity, the affinity for TPO of the Fab fragment expressed by SP2 was determined by competition studies with unlabeled recombinant TPO and was found to be ~$10^{-9}$ M (FIG. 21). The specificity of this interaction was evident by the inability of the Fab fragment to bind radiolabeled thyroglobulin, another major thyroid autoantigen.

Comparison of the nucleotide sequence of the IgG heavy (H) chain (FIG. 22) and light (L) chain (FIG. 23) with known germline sequences characterizes this TPO binding Fab fragment. Specifically, the VH gene belongs to the VHI family with 91.2% homology to the 1—1 germline gene (Pascual, V., and Capra, J. D. *Adv. Immunol.* VOL.49:1–74 (1991)). The D segment contains three of the 5 nucleotide motifs shared by $D_M$, $D_N$ and $D_{LR}$ (GGTAT) and $D_{LR}$ (TACTA, GTATG) (Pascual et al., supra). Because of very low homology with reported D region nucleotide sequences, it is difficult to assign the D region of SP2 to a particular gene family. The J segment is a JH3 which appears to be truncated at its 5' end (P). The light chain is coded for by a VKI which is 89.6% homologous with the germline gene HUMIGKLVJ (GenBank accession number D90158). The light chain J segment is a JK2 (Kipps, T. J., Tomhave, E., Chen, P. P., and Fox, R. I. *J.Immun.* VOL.142:4261–4268 (1989)).

DISCUSSION

The expression in bacteria of random combinations of heavy and light chain immunoglobulin cDNA genes has previously been used to generate human Fab fragments which bind tetanus toxoid using cDNA from individuals immunized with this antigen (Mullinax, R. L., Gross, E. A., Amberg, J. R., Hay, B. N., Hogrefe, H. H., Kubitz, M. M., Greener, A., Alting-Mees, M., Ardourel, D., Short, J. M., Sorge, J. A., and Shoper, B. *Proc. Natl. Acad. Sci. USA* VOL.87:8095–8099 (1990); Persson, M. A. A., Caothien, R. H., and Burton, D. R. *Proc. Natl. Acad. Sci. USA* VOL.88:2432–2436 (1991)). However, thre are no previous reports on the production of disease-associated human autoantibodies using this system. In the present sutdy, a human Fab fragment has been generated which binds a major thyroid autoantigen, TPO. The cDNA used for this purpose was transcribed from mRNA prepared from Graves' thyroid tissue which is enriched in B-lymphocytes capable of producing thyroid autoantibodies (McLachlan et al., supra; Atherton et al., supra).

Antibodies to TPO in patients with autoimmune thyroid disease are frequently of subclass IgG1 and/or IgG4, with kappa light chains predominating (Parkes, A. B., McLachlan, S. M., Bird, P., and Rees Smith, B. *Clin. Exp. Immunol.* VOL.57:239–243 (1984)). For this reason the initial approach undertaken was to construct and screen an IgG1-kappa combinatorial cDNA library. On the basis of available information, the VH and VL genes of SP2 appear to be moderately mutated forms of germline gene families VHI and VKI. The D region, which does not resemlbe any reported germline sequence, is likely to contribute further to recognition of TPO by SP2. It is not known whether this particular heavy and light chain combination reflects the in vivo situation. However, the high affinity of SP2 is comparable to reported affinities of TPO autoantibodies present in patients with autoimmune thyroid disease ($1.1\times10^{-9}$ M–$9.4\times10^{-8}$ M) (Beever, K., Bradbury, J., Phillips, D., McLachlan, S. M., Pegg, C., Goral, A., Overbeck, W., Feifel, G., and Rees Smith, B. *Clin. Chem.* VOL.35:1949–1954 (1989)). Therefore, the present example is belived to provide the first characterization at a molecular level of a human thyroid peroxidase antibody associated with autoimmune thyroid disease.

EXAMPLE XIX

Recogntion by Recombinant Autoimmune Thyroid Disease-Derived Fab Fragments of a Dominant Conformational Epitope on Human Thyroid Peroxidase Definition of the epitopes recognized by TPO autoantibodies is an important goal in understanding the pathogenesis of autoimmune thyroid disease. TPO autoantibodies appear to interact with different regions of the molecule. For example, some, but not all, TPO autoantibodies inhibit TPO enzymatic activity (Kohno, Y., Y. Hiyama, N. Shimojo, H. Niimi, H. Nakajima, and T. Hosoya, "Autoantibodies to thyroid peroxidase in patients with chronic thyroiditis: Effect of antibody binding on enzyme activities, *Clin. Exp. Immunol.* VOL.65:534–541 (1986)) and cross-react with myeloperoxidase or lactoperoxidase (Banga, J. P., N. Doble, R. W. s. Tomlinson, E. Odell, and A. M. McGregor, "Thyroid microsomal/thyroid peroxidase autoantibodies show discrete patterns of cross-reactivity to myeloperoxidase lactopeoxidase and horseradish peroxidase," *Immunology* VOL.67:197–204, (1989)). At the molecular level, a linear epitope for serum TPO autoantibodies was defined in the precedding example.

Human, disease-associated monoclonal TPO autoantibodies will be invaluable in defining TPO epitopes. However, as described above, such monoclonal antibodies are exceptionally difficult to generate by conventional techniques. The preceeding example describes the obtension of a human Fab fragment (designated "SP2" therein and also designated herein as "SP1.2") specific for TPO from B-cells infiltrating Graves' thyroid tissue. In the present example, the isolation of two additional TPO-specific Fab fragments (designated herein as "SP4" and "SP5," the same fragments also designated herein as "SP1.4" and "SP1.5," respectively) from a bacteriophage lambda library is described, as well as the expression and characterization of all three Fab fragments. The data indicate that TPO autoantibodies represented by these Fab fragments are present in all patients studied, constitute a high proportion of serum TPO autoantibodies in individual patients and interact with a conformational epitope on TPO.

MATERIALS AND METHODS

Molecular cloning of TPO-binding Fab fragments: Construction of the IgG1/kappa Fab fragment combinatorial cDNA library in the vector Immunozap (Stratacyte, La Jolla, Calif.) has been described above. The source of the mRNA was Graves' thyroid tissue, known to contain IgG secreting cells. The unamplified combinatorial library ($3\times10^6$ recombinants) was screen in XL1-Blue cells by conventional techniques (Maniatis, T., E. F. Fritsch, and J. Sambrook, "Molecular cloning. A laboratory manual," Cold spring Harbor Laboratory, Cold Spring Harbor Laboratory, N.Y., (1988)) using secreted recombinant human TPO as described in a preceding example, affinity purified with mouse monoclonal anti-TPO, labeled with $^{125}$I to a specific activity of ⁻10 uCi/ug protein by the iodogen method (Salacinski, P. R. P., C. McLean, J. E. C. Sykes, V. V. Clement-Jones, and P. J. Lowry, "Iodination of proteins, glycoproteins, and peptides using a solid-phase oxidizing agent, 1,3,4,6-tetrachloro-3 alpha, 6 alpha-diphenyl Glycoluril (Iodogen)," *Anal. Biochem.* VOL.117:136–146 (1981)). TPO-binding plaques were cloned to homogeneity and plasmids (Bluescript SK-) were excised from the Immunozap bacteriophage using the helper phage R408, according to the Stratacyte protocol. Nucleotide sequences were determined in both directions (Sanger, F., S. Nicklen, and A. R. Coulson, "DNA sequencing with chain terminating inhibitors," *Proc. Natl. Acad. Sci. USA* VOL.74:5463–5467 (1977)).

Preparation of soluble Fab fragments: Plasmid-bearing XL1 Blue cells were incubated overnight at 37 C in LB medium containing 1% glucose. After dilution in LB medium without glucose, cultures were further incubated at 37 C until the optical density of the cells reach 0.5 (600 nm). Protein synthesis was induced with 1 mM isopropyl b-D-thiogalacto-pyranoside (Sigma Chemical Co., St. Louis, Mo.) for 1 h at 37 C. The cells were then pelleted, frozen, at -20 C, resuspended in 0.02 volumes of 10 mM Tris pH 8.0 containing 2 ug/ml aprotinin, 1 ug/ml leupeptin, 1 ug/ml pepstatin, 0.1 mM phenylmethylsulfonyl fluoride (all from Sigma). The suspension was sonicated, membranes pelleted by centrifugation at 4000× g and the Fab fragments affinity purified from the supernatant using a Protein G sepharose column (Pharmacia, Piscataway, N.J.). The Fab proteins were ⁻99% pure as determined by SDS polyacrylamide gel electrophoresis (Laemmli, U.K., "Cleavage of structural proteins during the assembly of the head of bacteriophage T4," *Nature* VOL.227:680–685 (1970)).

Fab fragment binding to radiolabeled TPO: The interaction of the Fab fragments with $^{125}$I-TPO was investigated as previously described for thyroglobulin monoclonal autoantibodies (Fukuma, N., S. M. McLachlan, V. B. Petersen, P. Kau, J. Bradbury, M. Devey, K. Bleasdale, P. Grabowski, and B. Rees Smith, "Human thyroglobulin autoantibodies of subclasses IgG2 and IgG4 bind to different epitopes on thyroglobulin," *Immunology* VOL.67:129–131 (1989)). Briefly, duplicate aliquots of SP1.2, SP1.4 or SP1.5, serially diluted in assay buffer (0.15 M NaCl containing 10 mM Tris-HCl pH7.5 and 0.5% bovine serum albumin), were incubated with $^{125}$I-TPO (⁻25,000 cpm) and mouse monoclonal antibody to human kappa light chains (QELL, Recongition Sciences, Birmingham, U.K.) in a total volume of 200 ul. After 1 hour at room temperature, 100 ul donkey anti-moue Sac-cel (IDS, Boldon, Tyne and Wear, U.K.) was added, and the incubation continued for 30 minutes. After vortexing, the mixture was centrifuged for 5 minutes at 1000× g to sediment the immune complexes which were then counted to determine the percentage of radiolabeled TPO bound. The specificity of this interaction was assessed by the addition of increasing amounts ($10^{-12}$ M–$10^{-8}$ M) of unlabeled recombinant human TPO, human myeloperoxidase (Calbiochem, La Jolla, Calif.) or bovine lactoperoxidase (Sigma). The affinities of the Fab fragments for TPO were determined by Scatchard analysis (Scatchard, G., "The attractions of proteins for small molecules and ions," *Ann. NY Acad. Sci.* VOL.51:660–672 (1949)).

Competition studies between Fab fragments and serum TPO autoantibodies: Sera from 11 patients with autoimmune thyroid disease were studied. All sera contained high levels of TPO autoantibodies [detectable by ELISA (Schardt, C. W., S. M. McLachlan, J. Matheson, and B. Rees Smith, "An enzyme-linked immunoassay for thyroid microsomal antibodies, *J. Immunol. Methods* VOL.55:155–168 (1982)) at dilutions of 1:1000 or greater]. Binding of $^{125}$I-TPO by serum autoantibodies was measured by precipitating the antigen-antibody complex with Protein A (Pansorbin, Calbiochem)(Beever, K., J. Bradbury, D. Phillips, S. M. McLachlan, C. Pegg. A. Goral, W. Overbeck, G. Feifel, and B. Rees Smith, "Highly sensitive assays of autoantibodies to thyroglubulin and to thyroid peroxidase," *Clin. Chem.*, VOL.35, 1949–1954, (1989)) in the presence of increasing concentrations of Fab fragments. The Fab fragment-TPO complex, lacking the CH2 domain of the Fc region, is not precipitated by Pansorbin. Duplicate aliquots of sera were incubated for 1 hr at room temperature with $^{125}$I-TPO, alone or with Fab fragments. Pansorbin (100 ul) was added and the incubation continued for 30 min. After addition of 1 ml assay buffer (see above), the mixture was vortexed, centrifuged for 30 min at 1000× g (4 C), supernatants removed by aspiration and TPO remaining in the pellets counted. In preliminary experiments, serum dilutions needed to provide binding values of ⁻20% in the absence of Fab fragments were determined. These dilutions ranged from 1:600–1:2000. Non-specific $^{125}$I-TPO binding in the presence of control serum without TPO antibodies was 2–5% of total cpm added. This value was subtracted from the values obtained with patients' sera in calculating the percentage inhibition by the SP Fab fragments.

Competition studies between Fab fragments and serum TPO antibodies of different IgG subclasses: An ELISA was used for this purpose, similar to that previously described for TPO autoantibodies measured using thyroid microsomal antigen (Parkes, A. B., S. M. McLachlan, P. Bird, and B. Rees Smith, "The distribution of microsomal and thyroglobulin antibody activity among the IgG subclasses," *Clin. Exp. Immunol.* VOL.57:239–243 (1984)), with some modifications. Conditioned medium (50 ul per well) from CHO cells overexpressing a secreted form of TPO (described in a previous example), was used to coat ELISA plates (Immulon 4, Dynatech Laboratories, Chantilly, Va.) by incubation overnight at 4 C with an equal volume of bicarbonate buffer (pH 9.3). Serum TPO autoantibodies of different IgG subclasses were detected with murine monoclonal antibodies (Jefferis, R., et al., "Evaluation of monoclonal antibodies having specificity for human IgG sub-classes: results of an IUIS/WHO collaborative study," *Immunol. Letters* VOL.10:223–252 (1985)) to human IgG1 and IgG4 (HP6012 and HP6011, respectively; Unipath Inc., Nepean, Ontario, Canada) and IgG2 (HP6014; Sigma). Serum TPO autoantibodies with lambda light chains were detected using murine monoclonal anti-human lambda (312H, Recognition Sciences). The signal was developed with affinity-purified anti-mouse IgG conjugated to horse radish peroxidase (Sigma) and o-phenylene diamine+$H_2)_2$ as substrate and optical densities (O.D.) read at 492 nm. None of these murine monoclonal antibodies bound to the Fab fragments. Competition studies were performed by incubating sera (appropriately diluted) with or without increasing concentrations of SP1.2 Fab fragment.

Screening of TPO cDNA fragment library: Construction of the library and the method used for screening has been described above. Reactivity of Fab fragment SP1.2 was assessed using the murine anti-kapps antibody (QE11; Recognition Sciences) followed by affinity-purified anti-mouse IgG horse-radish peroxidase conjugate (Cappel, West Chester, Pa.), As a positive control, a murine monoclonal antibody (#40.28), generated against denatured TPO (Portman, L., F. W. Fitch, W. Havran, N. Hamada, W. A. Franklin, and L. J. DeGroot, "Characterization of the thyroid microsomal antigen, and its relationship to thyroid peroxidase, using monoclonal antibodies," *J. Clin. Invest.* VOL.81:1217–1224 (1988)) was used which recognizes a linear epitope expressed in this library.

Interaction between Fab fragments and denatured TPO: TPO in conditioned culture medium (described above) was reduced and alkylated using dithiothreitol and iodoacetamide (Nakajima, Y., R. D. Howells, C. Pegg, E. Davies Jones, and B. Rees Smith, "Structure activity analysis of microsomal antigen/thyroid peroxidase," *Molec. Cell. Endocrinal.*, VOL.53, 15–23, (1987)). ELISA plates were coated with native or denatured TPO, as described above. Binding of SP1.2, SP1.4 and SP1.5 ($10^{-9}$ M) was detected, as described above for serum TPO lambda autoantibodies, using monoclonal anti-kappa (QE11). Mouse monoclonal antibody (#40.28, diluted 1:100) and control ascites (NS-1, diluted 1:50; Cappel) were included as positive and negative controls respectively.

RESULTS

Nucleotide and derived amino-acid sequences of TPO-binding Fab fragments: Further screening of the Fab fragment combinatorial cDNA library for radiolabeled TPO binding yielded two additional Fab fragments (SP1.4 and SP1.5). The heavy chains of SP1.4 and SP1.5 were identical to that of previously isolated SP1.2. The light chains of SP1.4 and SP1.5, although closely related to that of SP1.2, differed in their nucleotide (FIGS. 24 and 26) and derived amino acid (FIGS. 25 and 26) sequences. All 3 light chains are coded for by VK1 and JK2, the closest germ-line genes being HUMIGKLV (GenBank accession #D90158) and KV312 (Kipps, T. J., E. Tomhave, P. P. Chen, and R. I. Fox, "Molecular characterization of a major autoantibody-associated cross-reactive idiotype in Sjogren's Syndrome," *J. Immun.* VOL.142:4261–4268 (1989), respectively.

Regarding the VK region, the SP1.4 and SP1.5 amino acid sequences are more homologous (90%) to HUMIGKLV than SP1.2 (83%). Only the kappa chain of SP1.2 has a potential glycosylation site, N—X—S, in the CDR1 (FIG. 25). Unlike SP1.2, in which the J segment is identical to the germline gene KV312, SP1.4 and SP1.5 (which are identical to each other) have 4 nucleotide substitutions, one of which results in a L to V change (FIG. 26).

Figure 27B:
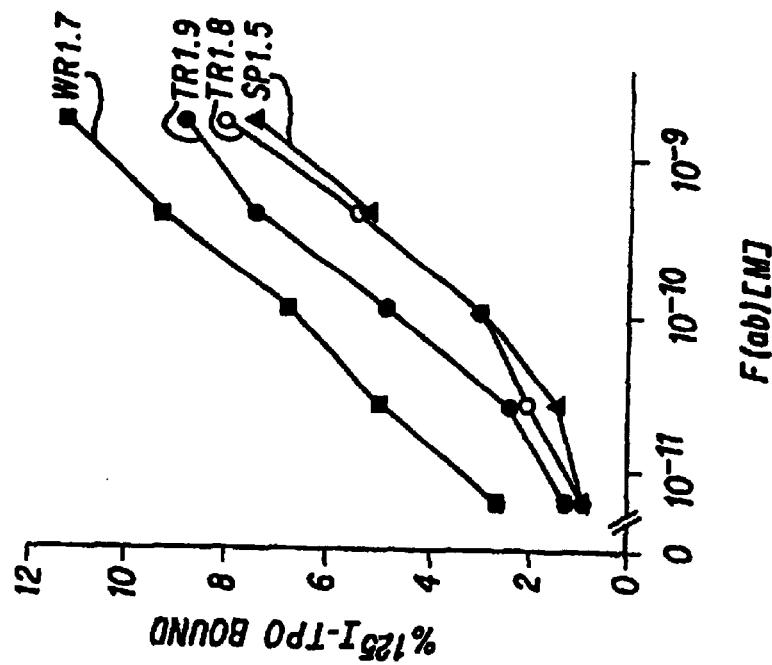
Figure 27A:
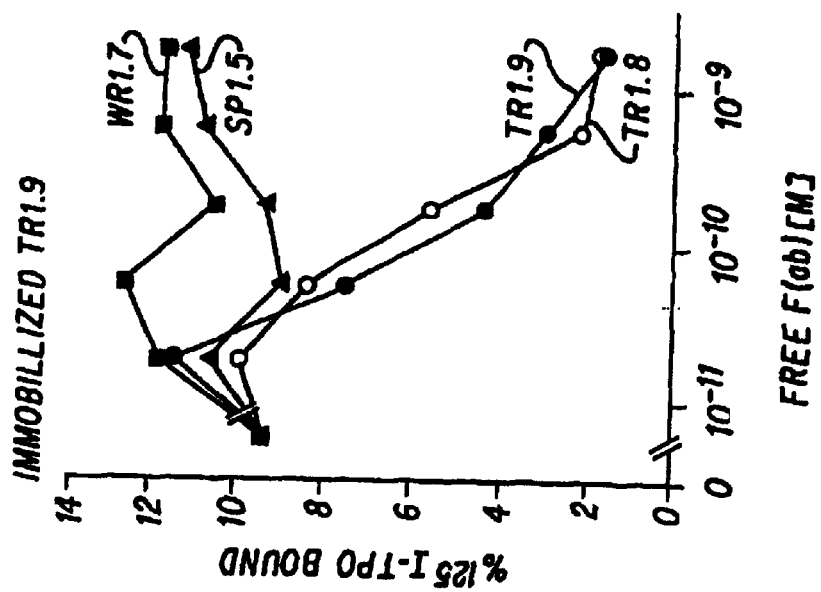

Specificity and affinity of TPO-binding Fab fragments: Binding of the SP1.2 Fab fragment to $^{125}$I-TPO was readily displaced by unlabeled TPO but not by myeloperoxidase or lactoperoxidase (FIG. 27A). SP1.4 and SP1.5 displayed the same specificity for TPO. As determined by Scatchard analysis, the affinities for TPO of all 3 Fab fragments were remarkably high (FIG. 27B). SP1.2 and SP1.5 displayed similar affinities (Kd $^-$6–8×$10^{-11}$ M). The affinity of SP1.4 was slightly lower ($^-$2×$10^{-10}$ M).

Competition studies between Fab fragments and serum TPO autoantibodies: We determined the abilities of SP1.2, SP1.4 or SP1.5 to compete with TPO autoantibodies in patients' sera for binding to $^{125}$I-TPO. Increasing amounts of SP1.2 ($10^{-10}$ to $10^{-7}$ M) progressively inhibited the binding to TPO by all of 11 sera from patients with autoimmune thyroid disease that were tested (FIG. 28). In the individual 11 sera, maximum inhibition ranged from 36% to 72%. The results obtained for 5 of these sera were similar with all 3 Fab fragments: 55±2% (mean % inhibition± S.E.M.) for SP1.2, 49±8% for SP1.5 and 43±6% for SP1.4. Because SP1.2, SP1.4 and SP1.5 have identical heavy chains and similar light chains belonging to the same VK gene family, it is reasonable to assume that they bind to the same, or closely related, epitope. This assumption is supported by studies in mice demonstrating that high affinity binding to a specific epitope is usually achieved by re-combination of the same heavy chain with light chains of the same family (Smith-Gill, S. J., P. A. Hamel, T. B. Lovoie, and K. J. Dorrington, "Contributions of immunoglobulin heavy and light chains to antibody specificity for lysozyme and two haptens," *J. Immun.* VOL. 139:4135–4144 (1987)).

Competition studies between Fab fragments and serum TPO autoantibodies of different subclasses and lambda light chain: Sera from individual patients contain different proportions of TPO antibodies of subclasses IgG1 and IgG4 and, in some patients, IgG2 (Parkes et al, Weetman, A. P., C. M. Black, S. B. Cohen, R. Tomlinson, J. P. Banga, and C. B. Reimer, "Affinity purification of IgG subclasses and the distribution of thyroid auto-antibody reactivity in Hashimoto's thyroiditis," *Scand. J. Immunol.* VOL. 30:73–82 (1991)). Therefore, the effect of SP1.2 (as a representative Fab) on the inhibition of TPO binding to serum TPO autoantibodies of different subclasses was investigated. Data illustrating 3 different inhibition patterns among the 9 sera analyzed are shown (FIG. 28). In one patient (FIG. 28A), IgG4 TPO antibody was inhibited to a greater extent (77%) than IgG1 TPO antibody (14%). In contrast, in another patient (FIG. 28B), IgG1 TPO antibody binding was inhibited to a greater extent (62%) than IgG4 TPO antibody (13%). Data on a third patient are shown (FIG. 28C) because this serum was one of three with detectable IgG2 TPO antibodies. A small degree of inhibition of IgG2 was observed (29%). The predominant inhibition for this patient was in the TgG1 subclass.

As reported previously (Parkes et al., supra), the serum TPO autoantibodies studies were predominantly of kappa light chain type. Because SP1.2 is a kappa Fab fragment, it was not possible to assess inhibition of serum kappa autoantibody binding to TPO. However, it was possible to investigate whether or not SP1.2 could compete with serum lambda TPO autoantibody binding to TPO. The extent of this inhibition was small, ranging from 12–18% in 4 sera.

Studies on the nature of the epitope recognized by TPO-specific Fab fragments: SP1.2 failed to recognize any plaques when used to screen a library of TPO cDNA fragments (66–166 amino acids in length) expressed in bacteria, as described above. In contrast, the positive control, murine monoclonal antibody #40.28, reacted with 5/⁻2000 plaques. These data suggested that the epitope recognized by SP1.2 is non-linear.

Confirmation that the epitope recognized by SP1.2 (and also by SP1.4 and SP1.5) is conformational was obtained in ELISA studies using native recombinant TPO and TPO denatured by reduction and alkylation. The three Fab fragments bound less well to denatured than to native TPO (FIG. 29). In contrast, binding of mouse monoclonal #40.28 was higher to denatured than to intact TPO.

DISCUSSION

The TPO-specific Fab fragments SP1.2, SP1.4 and SP1.5 all have the heavy chain variable region sequence described in a previous example dor SP1.2. The VH region is a member of the VHI family (91.2% homologous to the 1—1 germ-line gene) and the J segment is a JH3 with a truncation at its 5' end (Pascual, V., and J. D. Capra, "Human immunoglobulin heavy chain variable region genes: Organization, polymorphism and expression," *Advances in Immunology* VOL. 49:1–74 (1991)). Because of its contribution to CDR3, the D region of these high affinity antibodies, which is not a member of any families reported, is of interest. The SP D region does not appear to result from homologous recombination (Sanz, I., "Multiple mechanisms participate in the generation of diversity of human H chain CDR3 regions," *The Journal of Immunology* VOL. 14786:1720–1729 (1991)) of known D segments. However, there is modest homology with a portion of the very long D segment of a cytomegalovirus antibody (Newkirk, M. M., H. Gram, G. F. Heinrich, L. Ostberg, J. D. Capra, and R. L. Wasserman, "Complete protein sequences of the variable regions of the cloned heavy and light chains of a human anti-cytomegalovirus antibody reveal a striking similarity to human monoclonal rheumatoid factors of the Wa idiotypic family," *J. Clin. Invest.* VOL. 81:1511–1588 (1988)) and SP D shares the motif GGTAT in families $D_M$, $D_N$ and $D_{LR}$ and the motifs TACTA and GTATG in $D_{LR}$ (Pascual et al., supra).

The light chains of SP1.2, SP1.4 and SP1.5, though not identical, are closely related, moderately mutated members of the VKI and JK2 families. There is no relationship between the extent of mutation from the germline gene and their affinities for TPO. Overall, in accordance with previous data (Kabat, E. A., and T. T. Wu., "Identical V region amino acid sequences and segments of sequences in antibodies of different specificities," *J. Immuno.* VOL. 147:1709–1719 (1991)), the sequence information for both SP heavy and light chains suggests that one chain, in this case the heavy chain, is primarily responsible for SP specificity.

The SP Fab fragments were isolated from a library containing random combinations of heavy and light chain gene fragments. Therefore, it is not possible to determine whether or not the heavy and light chain combinations of the SP Fab fragments were present in vivo in the patient whose thyroid infiltrating B-cells were used to construct the combinatorial library. Nevertheless, the Fab fragments, particularly SP1.5 and SP1.2, have very high affinities for TPO, comparable to the highest affinity TPO autoantibodies reported for serum (Beever et al., supra). For this reason, as well as because of their derivation from a patient with autoimmune thyroid disease, the SP Fab fragments are suitable for investigating the interaction between TPO and serum TPO autoantibodies.

The ability of the SP Fab fragments to inhibit the binding to TPO of serum autoantibodies demonstrates identity or overlap between the Fab epitope and an epitope recognized by serum autoantibodies. Because this inhibition was observed for all 11 patients' sera examined, the epitope is very common in the TPO autoantibody repertoire. The present data indicate that the SP epitope is recognized by 36–72% of the TPO autoantibodies present in the sera of individual patients. The present data also indicate that patients' autoantibodies against the SP epitope are not restricted to a single IgG subclass. Thus, in some patients the SP epitope is predominantly IgG1, in others IgG4 and in a few IgG2. In terms of light chain type, the SP epitope is recognized poorly by TPO autoantibodies with lambda light chains. The SP epitope-recognizing antibodies in the patient population are, therefore, likely to contain kappa light chains, like the SP Fab fragments themselves.

Techniques previously available to study TPO epitopes, such as the use of synthetic peptides, proteolytic fragments and recombinant TPO fragments generated by cDNA libraries, are only capable of identifying linear epitopes. The present example provides surprising and significant evidence that the SP epitope, recognized by very common and abundant TPO autoantibodies, is not linear but is conformational. Crystallization of the complex between recombinant TPO-specific Fab fragments and recombinant TPO will ultimately permit the definition of the amino acids involved in the highly conformational epitope on TPO.

EXAMPLE XX

Lack of Promiscuity in Autoantigen-Specific H and L Chain Combinations as revealed by Human H and L Chain "Roulette"

A hallmark of autoimmune thyroid destruction in man is the presence in serum of high affinity IgG class autoantibodies to thyroid peroxidase (TPO), the primary enzyme involved in thyroid hormone synthesis (reviewed in McLachlan, S. M., and B. Rapoport, "The molecular biology of thyroid peroxidase: cloning, expression and role as autoantigen in autoimmune thyroid disease," *Endocr. Rev.* VOL. 13:192 (1992), incorporated herein by reference as though set forth in full). As described above, TPO is a glycoprotein of ⁻107 kD expressed on the surface of thyroid cells. Human autoantibodies to TPO are not monoclonal as evident by the contribution of different IgG subclasses and light chain types in the same patient (Parkes, A. B., S. M. McLachlan, P. Bird, and B. Rees Smith, "The distribution of microsomal and thyroglobulin antibody activity among the IgG subclasses," *Clin. Exp. Immunol.*, VOL. 57:239 (1984); Weetman, A. P., C. M. Black, S. B. Cohen, R. Tomlinson, J. P. Banga, and C. B. Reimer, "Affinity purification of IgG subclasses and the distribution of thyroid auto-antibody reactivity in Hashimoto's thyroiditis," *Scand. J. Immunol.* VOL. 30:73 (1989)).

The preceding examples descibe the cloning of three human IgG1/kappa autoantibodies (SP1.2, SP1.4 and SP1.5; also designated SP2, 4 and 5, respectively) which bind TPO specifically and with high affinity. These autoantibodies were obtained by expressing random combinations of H and L chain Ig genes as antigen binding fragments, ("F(ab)s"), in a bacteriophage lambda library, the cDNA of which library was prepared from B cells infiltrating the thyroid gland in a patient with autoimmune thyroid disease. The three TPO autoantibody F(ab)s share the identical Ig H chain. The L chains are not the same, but are derived from the same V kappa germline gene (HUMIGKLVJ) as described herein.

Because of the random nature of the H and L chain combinations in this cDNA library, the question arose as to whether or not the SP F(ab) autoantibody H chain (or L chain) could combine with a variety of other L chains (or H chains) in the parent library and still bind to TPO.

Recently it has been reported that there is notable promiscuity in the H and L chain combinations of murine F(ab)s which bind the hapten NPN (Kang, A. S., T. M. Jones, and D. R. Burton, "Antibody redesign by chain shuffling from random combinatorial immunoglobulin libraries," *Proc. Natl. Acad. Sci. USA* VOL. 88:11120 (1991)). In contrast to this promiscuity, the "roulette" experiments described in the present example demonstrate more restriction in the H and L chain combinations for high affinity binding to a human autoantigen, TPO.

MATERIALS AND METHODS

Library construction and screening: The plasmid of clone SP1.2 was digested with Xho I and Spe I to release the H chain cDNA insert. Similarly, the L chain cDNA fragment was obtained by Xba I and Sac I digestion. The inserts were gel-purified and ligated into Immunozap H and L arms (Stratacyte, La Jolla, Calif.), respectively, to generate a clonal SP1.2 H and a clonal SP1.2 L chain library, respectively. These libraries were amplified and the DNA extracted as described above. The DNA from the SP1.2 heavy chain library was digested with HindIII followed by EcoR1 and ligated with the DNA prepared from the original L chain library described above. Similarly the DNA from the SP1.2 light chain library was digested with Mlu1 followed by EcoR1 and ligated with the DNA from the original H chain library described above. The original H and L libraries contained >80% inserts of the correct size. The combinatorial libraries were screened in XL1-Blue cells by conventional techniques (Maniatis, T., E. F. Fritsch, and J. Sambrook, "Molecular cloning: A laboratory Manual," Cold Spring Harbor Laboratory. *Cold Spring Harbor Laboratory, N.Y.* (1982)) using secreted recombinant human TPO as described above, labeled with $^{125}$I to a specific activity of 10–20 uCi/ug protein by the iodogen method (Salacinski, P. R. P., C. McLean, J. E. C. Sykes, V. V. Clement-Jones, and P. J. Lowry, "Iodination of proteins, glycoproteins, and peptides using a solid-phase oxidizing agent, 1,3,4,6-tetrachloro-3 alpha, 6 alpha-diphenyl Glycoluril (Iodogen)," *Anal. Biochem.* VOL. 117:136 (1981)). TPO-binding plaques were cloned to homogeneity and plasmids were excised from the Immunozap bacteriophase using the helper phase R408, according to the Stratacyte protocol. Nucleotide sequencing of the cDNA inserts was performed by the dideoxynucleotide chain termination method (Sanger, F., S. Nicklen, and A. R. Coulson, "DNA sequencing with chain terminating inhibitors," *Proc. Natl. Acad. Sci. USA* VOL. 74:5463 (1977)).

F(ab) expression: F(ab)s were expressed as soluble proteins in XL1-Blue cells, as described above. In brief, protein synthesis was induced with 1 mM isopropyl-thio-galactopyranoside (Sigma Chemical Co., St. Louis, Mo.) for 1 h at 37 C. The cells were then pelleted, frozen at –20 C., resuspended in 0.02 volumes of 10 mM Tris pH 8.0 containing 2 ug/ml aprotinin, 1 ug/ml leupeptin, 1 ug/ml peptatin, 0.1 mM phenylmethylsulfonyl fluoride (all from Sigma). The suspension was sonicated, membranes pelleted by centrifugation at 4000×g and the F(ab)s were affinity purified from the supernatant using a Protein G sepharose column (Pharmacia, Piscataway, N.J.).

F(ab) binding of $^{125}$I-TPO: As previously described, F(ab)s diluted in assay buffer (0.15 M NaCl containing 10 mM Tris-HCl pH7.5 and 0.5% bovine serum albumin) were incubated with $^{125}$I-TPO ($^-$25,000 cpm) and mouse monoclonal antibody to human kappa light chains (QE11, Recognition Sciences, Birmingham, U.K.) in a total volume of 200 ul. After 1 hour at room temperature, 100 ul donkey anti-mouse Sac-cel (IDS, Boldon, Tyne and Wear, U.K.) was added, and the incubation continued for 30 minutes. After addition of 1 ml assay buffer and vortexing, the mixture was centrifuged for 5 minutes at 1000×g to sediment the immune complexes which were then counted to determine the % radiolabeled TPO bound. The affinities of the F(ab)s for TPO were determined by Scatchard analysis (Scatchard, G, "The attractions of proteins for small molecules and ions," *Ann. NY Acad. Sci.* VOL. 51:660 (1949)) from values obtained in the presence of increasing concentrations of unlabeled TPO. The data presented are the mean ± SEM of triplicate determinations.

Competition between F(ab)s for binding to TPO: One F(ab) was immobilized by incubation (total volume of 200 ul) with murine mAb anti-human kappa (QE11) for 1 h at room temperature. After incubation with 100 ul of Sac-cel (30 min at room temperature), the complexes were diluted in assay buffer (see above) and centrifuged at 1000×g (5 min at 4 C.). The pellets were resuspended in normal human serum diluted 1:30 in assay buffer to saturate remaining anti-kappa binding sites. In a separate set of tubes, increasing concentrations of "free" F(ab) were preincubated with $^{125}$I-TPO for 1 h at room temperature. Aliquots (100 ul) were then incubated for 30 min with the immobilized F(ab) pellets, washed with assay buffer and radioactivity bound to the Sac-cel was counted. Non-specific binding ($^-$2% of total counts added) was substracted to provide values for specific binding to TPO.

RESULTS

Frequencies of $^{125}$I-TPO binding clones. Combining the L chain of SP1.2 with the SP parent H chain library yielded a combinatorial library of $^-10^7$ pfu (SP1.2 L×H library). Similarly, the combination of the SP1.2 H chain with the SP parent L chain library resulted in a library of $^-10^7$ pfu (SP1.2 H×L). As expected, this "roulette" with either the SP1.2 L or H chain led to a greater frequency of TPO-binding clones than was detected in the original screening of the parent library (Table V). Further, the frequency of TPO-binding was 10-fold greater in the SP1.2 H×L library than in the SP1.2 L×H library.

TPO binding clones from the SP1.2 L×H library. Determination of the nucleotide sequences of the 6 new TPO-binding clones isolated from the SP1.2 L×H library revealed that the VDJ regions of 5 (SP1.7–11) were almost identical to those of the original SP1.2. The VH of SP1.2 appears to be derived from the VH1 family germline gene 1—1 (Pascual, V., and J. D. Capra, "Human immunoglobulin heavy chain variable region genes: Organization, polymorphism and expression," *Advances in Immunology* VOL. 49:1 (1991)). In the VH region, 2 clones (SP1.7 and SP1.8) differed from the original SP1.2 H chain by only one amino acid (Pro and Leu for Ala 24, respectively). The D regions of SP1.7–11 are identical and differ from the SP1.2 D region by a single silent base substitution. The J regions of SP1.7–11 are of the JH6 family (Pascual et al., supra).

Reexamination of the SP1.2 DJ regions indicates that this clone, too, is a JH6 (rather than a JH3) combined with a very short D region.

One of the 6 new clones (SP4.6) from the SP1.2 L×H library differed more substantially from SP1.2 as well as from SP1.7–11. SP4.6 is a member of the VH1 family. However, it is more closely related to the germline gene hv1L1 (Olee, T., E. W. Lu, D-F. Huang, R. W. Soto-Gil, M. Deftos, F. Kozin, D. A. Carson, and P. P. Chen, "Genetic analysis of self-associating immunoglobulin G rheumatoid factors from two rheumatoid synovia implicates an antigen-driven response," *J. Exp. Med.* VOL. 1750:8310 (1992)) (88% homology) than to 1—1. The D region does not resemble any published D region sequence. The SP4.6 J region is a JH4 truncated at its 5' end. The most surprising finding was that the hinge region sequence indicates that SP4.6 is an IgG4, in contrast to SP1.2 and SP1.7–11 which are IgG1. The C region primer used for PCR in constructing the SP H chain library ("CH1"; Stratacyte, San Diego Calif.) is described as an IgG1 primer with the capacity to cross-prime with other IgG subclasses.

TPO binding clones from the SP1.2 H×L library. The nucleotide sequences of the L chains were determined in 11 TPO-binding clones in the SP1.2 H×L library. At the amino acid level, the V kappa regions of 9 clones were very similar to, and 2 clones (SP1.17 and SP1.19) were identical to, the original SP1.2 L chain. Four of the 9 clones (SP1.14, −15, −21 and −22) have identical V kappa regions. All 11 new L chain clones appear to be derived from the V kappa germline gene HUMIGKLVJ (GenBank accession number D90158), as described above for SP1.2. At the amino acid level, all 11 are more homologous with HUMIGKLVJ (83% for SP1.18 to 92% for SP1.20) than is SP1.2 (81%). The J kappa regions of 10 of the 11 new clones belong to JK1 or JK2 . The J kappa region of SP1.21 has not been assigned. SP1.14, SP1.15 and SP1.22 have identical V kappa and J kappa sequences. Because clones SP1.17 and SP1.19 have JK2 regions (like SP1.2) these clones are, overall, identical to SP1.2.

Affinities for TPO of selected F(ab)s. The proteins for two of the newly isolated F(ab) clones, SP4.6 and SP1.20, were expressed and purified. SP4.6 was selected in view of its distinctive H chain and SP1.20 because its L chain was the least mutated from the putative germline gene. Purified SP1.2 is described above. The affinities for TPO of the SP4.6 and SP1.20 F(ab)s, calculated by Scatchard analysis, are very similar to each other (kD $1.0\pm0.2\times10^{-10}$ M and $1.4\pm0.3\times10^{-10}$ M, respectively) and to SP1.2 ($0.8\pm0.1\times10^{-10}$ M) (means±SEM).

Binding domains on TPO for SP F(ab)s. To determine whether or not there was overlap in the domains on TPO recognized by SP4.6, SP1.20 and SP1.2, studies with an immobilized SP1.2 F(ab) were performed. As expected, pre-incubation of $^{125}$I-TPO with increasing concentrations of free SP1.2 inhibited the subsequent binding of the antigen to the immobilized SP1.2 (FIG. 26). The SP4.6 and SP1.20 F(ab)s were equally effective, indicating that the binding domains of all 3 F(ab)s overlapped. No competition was observed with another anti-TPO F(ab) cloned from another patient.

DISCUSSION

In the present example, a single H or L chain already known to confer high affinity ($^-10^{-10}$ M), specific binding for TPO was chosen. This H (or L chain) was used to search for other L (or H) chains that could form a F(ab) capable of binding TPO. That is, it was undertaken to "spin the wheel" of the H and L chain repertoire of activated B cells infiltrating the patient's thyroid gland. As expected, the frequency of TPO-binding clones in the libraries generated by this biased recombination was higher than in the original random combinatorial library. However, the frequency was surprisingly lower (Table V) than would be expected if promiscuous binding to a variety of H or L chain was compatible with specific antigen binding.

The antibody repertoire in thyroid tissue B cells of patients with autoimmune thyroid disease is relevant to this discussion. This tissue is enriched, compared with draining lymph nodes and peripheral blood, in B cells actively secreting autoantibodies to the three major thyroid autoantigens, TPO, thyroglobulin and the thyrotropin receptor (McLachlan, Rapoport et al., supra; McLachlan, S. M., A. McGregor, B. Rees Smith, and R. Hall, "Thyroid-autoantibody synthesis by Hashimoto thyroid lymphocytes," *Lancet* VOL. i:162 (1979)).

This bias makes even more remarkable the paucity of H and L chains from this patient capable of combining with the pre-selected L or H chain to form a functional TPO binding site. For example, frequencies of 1 in 50 for a functional H chain have been reported in libraries of a mouse immunized with influenza hemagglutinin or in a human immunized with tetanus toxoid (Kang et al., supra).

Nucleotide sequence analysis of the H and L chains of the new TPO binding clones reveals even more restriction. Thus, using the SP1.2 H chain, all 11 new clones utilized L chains from the same VK1 family germline gene. This germline gene was also used by the three other TPO F(ab)s described above. Amino acid substitutions predominate in the CDR regions. Overall, taking into account the V and J kappa regions of all 14 L chains, only 10 are distinct because several were identical to the SP1.2 L chain, or to each other.

Additional evidence for restriction was the very limited variety of H chains "captured" by the SP1.2 L chain in generating new TPO-binding clones. Five of the 6 clones were very closely related to the SP1.2 H chain, which is also shared by the previously identified SP1.4 and SP1.5 clones. However, in contrast to the L chains, one totally different H chain was isolated in SP4.6. This H chain differed from all others in the following respects: i) it is apparently derived from a different VH germline gene, although the same VH1 family; ii) the D region is totally distinct; iii) it uses a different J region; and iv) it belongs to the IgG 4 subclass. This heavy chain is clearly more rare than the SP1.2 and related H chains, possibly because the oligonucleotide primer used to obtain the H chain library is suboptimal for IgG4. It is likely that this H chain was only found because of the bias introduced by the roulette approach.

In addition to providing data on the frequency and characterization of TPO-binding H and L chain combinations, the present example illustrates important features with respect to antibody affinity and binding domains. These TPO autoantibodies have affinities for antigen several orders of magnitude above those reported for naturally occuring, polyreactive autoantibodies (Kd $10^{-3}$–$10^{-8}$ M) (Nakamura, M., S. E. Burastero, Y. Ueki, J. W. Larrick, A. L. Notkins, and P. Casali, "Probing the normal and autoimmune B cell repertoire with Epstein-Barr virus: frequency of B cells producing monoreactive high affinity autoantibodies in patients with Hashimoto's disease and systemic lupus erythematosus," *J. Immuno.* VOL. 141:4165 (1988)).

It is of interest that the affinity of SP1.20 is high (similar to SP1.2) even though its V kappa chain is less mutated than that of SP1.2 (92% and 81% homology to the germline gene, respectively). Assuming that both genes are, indeed, derived from HUMIGKLVJ, it is possible that affinity maturation of the light chain does not play a critical role in determining the affinity of the F(ab) for TPO.

A most surprising and unexpected finding in the present example concerns the TPO binding domains of the SP F(ab)s. Thus, in accordance with the data of Radic et al. (Radic, M. Z., M. A. Mascelli, J. Erikson, H. San, and M. Weigert, "Ig H and L chain contributions to autoimmune specificities," *J. Immun.* VOL. 146:176 (1991)) concerning murine autoantibodies to DNA, it was anticipated that both the SP1.2 and SP1.20 F(ab)s, which have the same H chain and have closely related L chains, would interact with overlapping epitopes and bind to the same domain on TPO. However, a similar domain on TPO was recognized by both SP4.6 and SP1.2 despite the fact that their V, D and J regions are quite different. This finding contrasts with the data of Martin et al. (Martin, T., S. F. Duffy, D. A. Carson, and T. A. Kipps, "Evidence for somatic selection of natural autoantibodies," *J. Exp. Med.* VOL. 175, 983 (1992)), who found that polyspecific autoantibody activity could only be generated with a specific D region.

The results obtained in the present example also were unexpected in view of the extensive analysis of V region H and L chain combinations by Kabat and Wu (Kabat, E. A., and T. T. Wu, "Identical V region amino acid sequences and segments of sequences in antibodies of different specificities," *J. Immun.* VOL. 147, 1709 (1991)), which suggested VH dominance in defining antibody specificity in many instances. However, the present findings raise the possibility that the L chain is critical in defining epitope specificity, even in the presence of completely different D regions and non-identical VH regions.

TABLE V

Frequencies of $^{125}$I-TPO binding clones in "roulette" of SP1.2 H and L chains.

| F(ab) Combinatorial Library | Frequency | Plaques Screened |
| --- | --- | --- |
| SP H Chain × SP L Chain | 1:60,000 | 180,000 |
| SP1.2 L Chain × SP H Chain | 1:5,000 | 30,000 |
| SP1.2 H Chain × SP L Chain | 1:500 | 15,000 |

EXAMPLE XXI

Human Organ-Specific Autoimmune Disease:
Molecular Cloning of an Autoantibody Repertoire for a Major Autoantigen Establishes an Immunodominant Region The most common organ-specific autoimmune disease in man involves the thyroid. Hashimoto's thyroiditis and Graves' disease, in their pure forms, represent two ends of a clinical spectrum ranging from glandular hypofunction to hyperfunction. In both diseases there is a breakdown in tolerance to a number of thyroid-specific autoantigens and the generation of a marked, high-affinity IgG antibody response. Thyrotropin receptor antibodies occur predominantly in Graves' disease and are responsible for hyperthyroidism (Nagayama, Y., and Rapoport, B., "The thyrotropin receptor twenty five years after its discovery: new insights following its molecular cloning, *Mol. Endocrinol.* VOL. 6:145–156 (1992). Autoantibodies to thyroglobulin, of uncertain pathogenetic importance, tend to be found in patients with Hashimoto's thyroiditis rather than Graves' disease.

Autoantibodies against thyroid peroxidase (TPO), however, are a sine qua non in patients with active autoimmune thyroid disease (Beever, K., Bradbury, J., Phillips, D., McLachlan, S. M., Pegg, C., Goral, A., Overbeck, W., Feifel, G., and Rees Smith, B., "Highly sensitive assays of autoantibodies to thyroglobulin and to thyroid peroxidase," *Clin. Chem.* VOL. 35:1949–1954 (1989)). There is evidence that TPO autoantibodies play a role in thyroid cell destruction (reviewed in McLachlan, S. M., and Rapoport, B., *Endocr. Rev.*, supra). TPO autoantibodies, which correlate well with thyroid inflammation on histological examination (Yoshida, H., Amino, N., Yagawa, K., Uemura, K., Satoh, M., Miyai, K., and Kumahara, Y., "Association of serum antithyroid antibodies with lymphocytic infiltration of the thyroid gland: Studies of seventy autopsied cases," *J. Clin. Edocrinol. Metab.* VOL. 46:859–862 (1978)), are present in up to 25% of the adult female population (Prentice, L. M., Phillips, D. I. W., Sarsero, D., Beever, K., McLachlan, S. M., and Rees Smith, B., "Geographical distribution of subclinical autoimmune thyroid disease in Britain: a study using highly sensitive direct assays for autoantibodies to thyroglobulin and thyroid peroxidase," *Acta Endocrinol.* VOL. 123:493–498 (1990)). In most cases the disease is sub-clinical, because of sufficient thyroid reserve and regeneration.

Information on the genes coding for organ-specific autoantibodies, as well as knowledge of the autoantibody epitopes, would be invaluable in understanding the pathogenesis of antibody-mediated autoimmune diseases. Among the major organ-specific human autoimmune diseases (thyroiditis, diabetes mellitus type I, pemphigus vulgaris, myasthenia gravis, pernicious anemia and Addison's disease), few IgG class monoclonal autoantibodies have been produced and even fewer cloned at the molecular level, as described in previous examples. In no disease have both the autoantibody repertoire and the autoantigenic domains been defined.

The present example reports the molecular cloning of the genes for 30 new organ-specific (TPO) human antiantibodies. These genes all code for high affinity, IgG autoantibodies. It is demonstrated that these TPO autoantibodies, which utilize a restricted number of H and L chain genes, encompass a restricted immunodominant region on TPO recognized by patients with autoimmune thyroid disease.

MATERIALS AND METHODS

Molecular cloning of TPO-binding Fab fragments: Five new human F(ab) combinatorial cDNA libraries were constructed in the vector Immunozap (Stratacyte, La Jolla, Calif.) as described in the preceding example, with some modifications as described herein. The source of the mRNA for cDNA synthesis was thyroid tissue from 3 different Graves' patients (WR, TR and JA). Two heavy (H) chain libraries were constructed from the WR and JA cDNA, one using the "IgG1" constant region primer of Stratacyte and the other using an IgG4 constant region primer based on nucleotide sequence data in the IgG4 hinge region (IgG 4 Sequence Prime, 1992). In an attempt to cover as wide a range of VH genes as possible, in addition to the VH region primers provided by Stratacyte we used upstream primers described by Persson et al. (Persson, M. A. A., Caothien, R. H., and Burton, D. R., "Generation of diverse high-affinity human monoclonal antibodies by repertoire cloning," *Proc. Natl. Acad. Sci. USA* VOL. 88:2432–2436 (1991)) or based on those of Marks et al. (Marks, J. D., Tristem, M., Karpas, A., and Winter, G., "Oligonucleotide primers for polymerase chain reaction amplification of human immunoglobulin variable genes and design of family-specific oligonucleotide probes," *Eur. J. Immunol.* VOL. 21:985–991 (1991)).

Preparation of soluble Fab fragments: F(ab)s were expressed as soluble proteins in XL1-Blue cells, as described above. In brief, protein synthesis was induced with 1 mM isopropyl-thio-galacto-pyranoside (Sigma Chemical Co., St. Louis, Mo.) for 1 h at 37 C. The cells were then pelleted, frozen at −20 C., resuspended in 0.02 volumes of 10 mM Tris pH 8.0 containing 2 ug/ml aprotinin, 1 ug/ml leupeptin, 1 ug/ml pepstatin, 0.1 mM phenylmethylsulfonyl fluoride (all from Sigma). The suspension was sonicated, membranes pelleted by centrifugation at 4000×g and the F(ab)s were affinity purified from the supernatant using a Protein G sepharose column (Pharmacia, Piscataway, N.J.).

F(ab) binding of $^{125}$I-TPO: As described above, F(ab)s diluted in assay buffer (0.15 M NaCl containing 10 mM Tris-HCl pH7.5 and 0.5% bovine serum albumin) were incubated with $^{125}$T-TPO ($^{18}$25,000 cpm) and mouse monoclonal antibody to human kappa light chains (QE11, Recognition Sciences, Birmingham, U.K.) in a total volume of 200 ul. After 1 hour at room temperature, 100 ul donkey anti-mouse Sac-cel (IDS, Boldon, Tyne and Wear, U.K.) was added, and the incubation continued for 30 minutes. After addition of 1 ml assay buffer and vortexing, the mixture was centrifuged for 5 minutes at 1000×g to sediment the immune complexes which were then counted to determine the % radiolabeled TPO bound. The affinities of the F(ab)s for TPO were determined by Scatchard analysis from values obtained in the presence of increasing concentrations of unlabeled TPO.

Competition between F(ab)s for binding to TPO: One F(ab) was immobilized by incubation (total volume of 200 ul) with murine mAb anti-human kappa (QE11) for 1 h at room temperature. After incubation with 100 ul of Sac-cel (30 min at room temperature), the complexes were diluted in assay buffer (see above) and centrifuged at 1000×g (5 min at 4 C.). The pellets were resuspended in normal human serum diluted 1:30 in assay buffer to saturate remaining anti-kappa binding sites. In a separate set of tubes, increasing concentrations of "free" F(ab) were preincubated with $^{125}$I-TPO for 1 h at room temperature. Aliquots (100 ul) were then incubated for 30 min with the immobilized F(ab) pellets, washed with assay buffer and radioactivity bound to the Sac-cel was counted. Non-specific binding (~2% of total counts added) was substracted to provide values for specific binding to TPO.

Competition studies between Fab fragments and serum TPO autoantibodies: Sera from 10 patients with autoimmune thyroid disease were studied. All sera contained high levels of TPO autoantibodies [detectable by ELISA (Schardt, C. W., McLachlan, S. M., Matheson, J., and Rees Smith, B., "An enzyme-linked immunoassay for thyroid microsomal antibodies," J. Immunol. Methods VOL. 55:155–168 (1982)) at dilutions of 1:1000 or greater]. Binding of $^{125}$I-TPO by serum autoantibodies was measured by precipitating the antigen-antibody complex with Protein A (Pansorbin, Calbiochem) as described above in the presence of increasing concentrations of Fab fragments. The Fab fragment-TPO complex, lacking the CH2 domain of the Fc region, is not precipitated by Pansorbin. Duplicate aliquots of sera were incubated for 1 h at room temperature with $^{125}$I-TPO, along or with Fab fragments. Pansorbin (100 ul) was added and the incubation continued for 30 min. After addition of 1 ml assay buffer (see above), the mixture was vortexed, centrifuged for 30 min at 1000×g (4 C.), supernatants removed by aspiration and TPO remaining in the pellets counted. In preliminary experiments, serum dilutions needed to provide binding values of ~20% in the absence of Fab fragments were determined. These dilutions ranged from 1:600–1:2000. Non-specific $^{125}$I-TPO binding in the presence of control serum without TPO antibodies was 2–5% of total cpm added. This value was subtracted from the values obtained with patients' sera in calculating the percentage inhibition by the SP Fab fragments.

RESULTS

Frequencies and subclass of TPO-specific F(ab)s: Screening 5 F(ab) combinatorial libraries from 3 new patients (WR, TR and JA) yielded 34 TPO-binding clones which were plaque-purified. The nucleotide sequences, determined for 32 clones, were used to classify these clones on the basis of their presumptive germline genes (Table VI). For completeness, TPO-specific F(ab)s from a fourth Graves' patient, as described in preceding examples, are also shown. The frequencies of TPO-binding F(ab)s differed markedly between patients. Far more TPO-specific F(ab)s were obtained from patients TR and WR than patients SP and JA.

For two patients, two different libraries were prepared. The WR I, TR I, JA I and the previously described SP I libraries used an "IgG1" primer (Stratacyte, San Diego) which has since been observed to crossprime with IgG4. The WR IV and JA IV libraries used an IgG4 specific primer as described above. Both IgG1 and IgG4 F(ab)s were isolated from the WR I and SP I libraries, whereas only IgG4 F(ab)s were obtained from the WR IV library and at a higher frequency. In contrast, the TR I library yielded only IgG1 F(ab)s. The large number of TPO-specific IgG4 F(ab)s obtained from the WR I library and the lack of such F(ab)s from the TR I library is consistent with the greater contribution of Ig4 to TPO autoantibodies in the serum of patient WR relative to patient TR.

TPO-specific F(ab) gene usage: Analysis of the presumptive germline genes used for 34 TPO human autoantibodies revealed the use of relatively restricted numbers and combinations of H and L chain genes (Table VI). In particular, L chain germline gene HUMIGKLVJ is used in TPO autoantibodies from all 4 patients. In 3 patients, HUMIGKLVJ was the only L chain obtained. In one patient (TR), 2 other TPO-specific L chains were obtained; A' is a VK1 (like HUMIGKLVJ) and A3 is a VK2. Of interest is an apparent association between JK VH gene usage (see below). For example, in 2 different patients (WR and TR), the association of JK1 with HUMIGKLVJ is seen only with VH gene 3-1.

The TPO-specific F(ab) H usage was less restricted than that of the L chain. Seven different H chains were used, involving 5 VHI, 1 VH3 and 1 VH4 germline genes. The D regions were all unique. Three of the H chains (1-1, HV1L1 and 3-1) are used in two patients. Each of these H chains is a member of the VH1 family and is used in combination with L chain germline gene HUMIGKLVJ. Four of the TPO-specific H chains were found only in individual patients (4.22, 8-1B, HV1263 and V35). Of these H chains, two were combined with L chain HUMIGKLVJ, 422 (a VH4) and 8-1B (a VH3). Out of a total of 7 H and L chain combinations, only 2 were unique for both their H and L chains (HV1263/A3 and V35/A').

F(ab) affinities for TPO: Recombinant F(ab)s representative of the different different H and L chain permutations were expressed (Table VII). With the exception of clone WR4.6, sufficient amounts (up to ~40 ug purified protein/liter) of purified protein were obtained for further studies. Calculation of the affinities (Kd) for human TPO revealed all F(ab)s to bind with high affinity ($^{-}10^{-10}$ M) (Table VII), comparable to autoantibodies in patients' sera (Beever et al., (1989) supra).

Domains on TPO recognized by F(ab)s: Competition between pairs of F(ab)s for binding to human TPO was used to define their respective binding domains. In this approach, increasing concentrations of one F(ab) were pre-incubated with radiolabelled TPO and then added to a second, immobilized F(ab). Representative experiments are shown in FIG. 27. For example (FIG. 27A), TR1.8 and TR1.9 each completely inhibited TPO binding to immobilized TR1.9. In contrast, pre-incubation of WR1.7 and SP1.5 with radiolabeled TPO did not prevent subsequent TPO binding to immobilized TR1.9. Despite these differences in their ability to compete for TPO binding to TR1.9, all free F(ab)s were capable of binding comparable amounts of radiolabeled TPO in separate, concurrent assays (FIG. 27B).

Figure 27D:
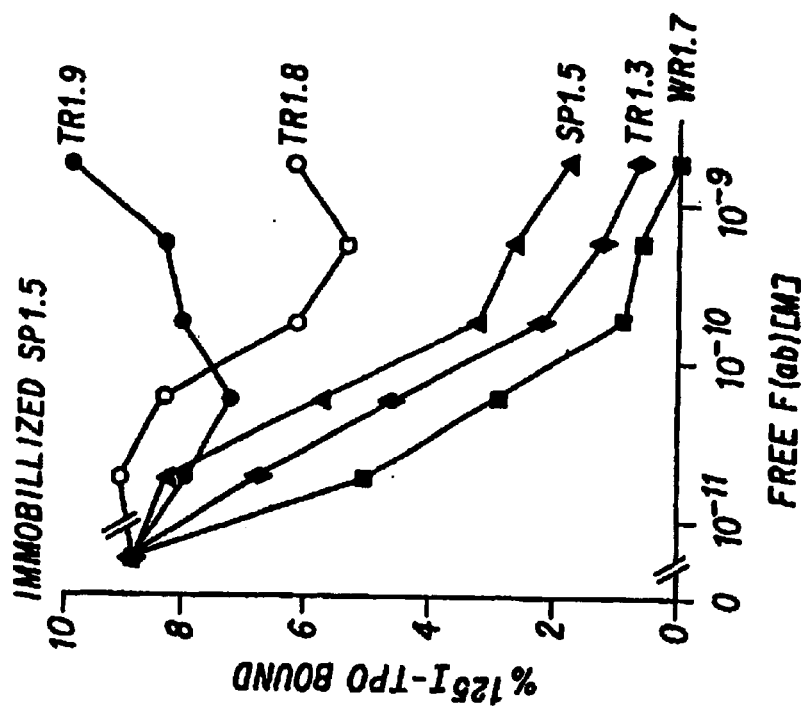
Figure 27C:
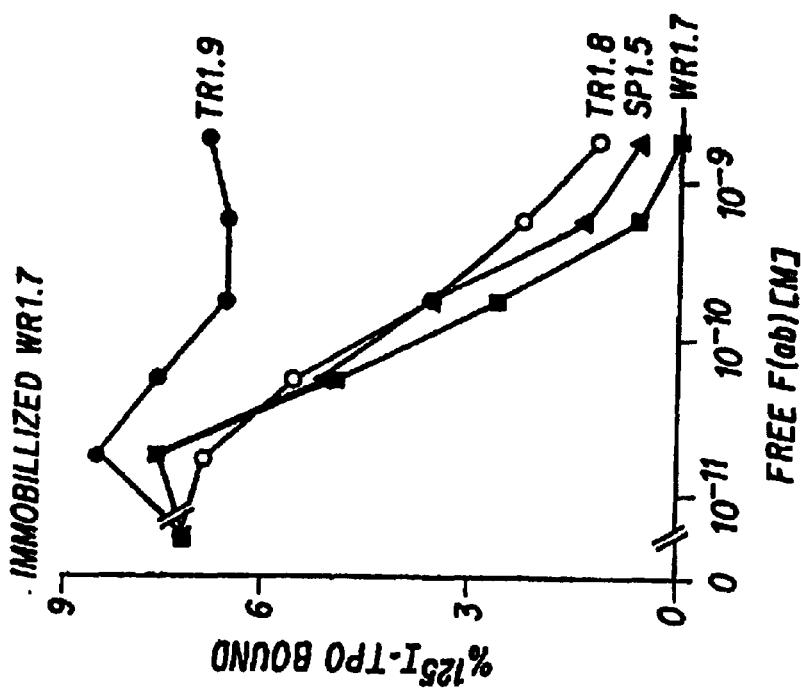

The above experiment (FIG. 27A and 27B) demonstrates overlap in the areas on TPO recognized by TR1.9 and TR1.8 but not between TR1.9 and WR1.7 or SP1.5. Similarly, there was overlap in the WT1.7 binding domain with those of TR1.8 and SP1.5 but not with TR1.9 (FIG. 27C). The SP1.5 binding domain overlapped that of TR1.3 and WR1.7 but not TR1.9 (FIG. 27D). The SP1.5 domain appeared to overlap to a small extent with that of TR1.8 (FIG. 27D). It is important to note that these differences between F(ab) binding domains are not related to differences in their affinities for TPO (Table VII).

Experiments covering all permutations of immobilized and free F(ab)s suggest that there are two domains, A and B, recognized on human TPO. The extent to which the F(ab)s interact with each domain is summarized in Table VIII and is shown schematically in FIG. 28. The binding sites of SP1.5 and WR4.5 lie completely within the TPO A domain. TR1.9 binds entirely to the B domain. TR1.8 interacts predominantly with the B domain but overlaps slightly with the A domain. Conversely, WR1.7 binds primarily to the A domain but also overlaps with TR1.8 (but not TR1.9) in the B domain. The binding site of TR1.3 spans the A and B domains equally.

Domains on TPO recognized by autoantibodies in patients' sera: The question arises as to what extent the TPO binding domains A and B reflect the binding domains of TPO autoantibodies in patients' sera. F(ab)s WR1.7 and TR1.9 were selected for competition studies with serum TPO autoantibodies because their binding sites do not overlap yet extensively cover the A and B domains. A spectrum of competition patterns was observed in 10 randomly selected sera of patients with autoimmune thyroid disease. In the representative examples shown, TPO autoantibodies in patients' sera were inhibited preferentially by WR1.7 (FIG. 29A), preferentially by TR1.9 (FIG. 29B) or in a more balanced proportion by both F(ab)s (FIG. 29C). Overall, of the 10 sera, 5 were inhibited preferentially by WR1.7, 2 by TR1.9 and 3 to approximately the same extent by WR1.7 and TR1.9. Of greater importance was the efficacy of the combination of the WR1.7 and TR1.9 F(ab)s in competing for serum TPO autoantibody binding. In the 10 sera, this combination inhibited TPO autoantibody binding by 83±5% (mean ± S.E.M.). These figures underestimate the full extent of the inhibition because of limitations to the highest concentrations of F(ab)s which could be used for competition.

DISCUSSION

The present example identifies and characterizes the genes coding for a comprensive panel of high affinity human autoantibodies to a major organ-specific autoantigen. These recombinant F(ab)s essentially cover the region of thyroid peroxidase recognized by all autoantibodies in the sera of patients with thyroiditis, the most common autoimmune disease. In the more intensively studied connective tissue diseases, genes for numerous autoantibodies have been characterized. Initially, the "natural" and disease-associated autoantibodies described were IgM, many of low affinity and with polyspecificity (Casali, P., Inghirami, G., Nakamura, N., Davies, T. F., and Notkins, A. L., "Human monoclonals from antigen-specific selection of B lymphocytes and transformation with EBV," Science VOL. 234:476 (1986); Sanz, I., Casali, P., Thomas, J. W., Notkins, A. L., and Capra, J. D., "Nucleotide sequences of eight human natural autoantibody VH regions reveals apparent restricted use of VH families," J. Immun. VOL. 142:4054–4061 (1989)). More recently, high affinity IgG-class rheumatoid factors and antibodies to double-stranded DNA have been produced and defined (Manheimer-Lory, A. J., Davidson, A., Watkins, D., Hanningan, N., and Diamond, B., "Generation and analysis of clonal IgM and IgG producing B cell lines expressing an anti-DNA associated idiotype, J. Clin. Invest. VOL. 87:1519 (1991)). However, the present example is believed to constitute the first definition of a complete autoantibody repertoire and its antigenic domain(s) in either organ specific or non-organ specific autoimmune disease in man. Those of skill will recognize the diagnostic and especially therapeutic implications of the present invention in the context of the level of skill in the art, when the teachings of the present invention are fully appreciated.

From thyroid tissue-infiltrating B cells from three patients with autoimmune thyroiditis, the nucleotide sequences of 30 new TPO-specific F(ab)s have been cloned and determined. Previous examples present information on four antibodies obtained from a fourth patient. A limited number of H (7) and L (3) chain genes code for this total of 34 F(ab)s. It is unlikely that this restriction can be attributed to limitations imposed by the primers used in the PCR to obtain the H and L chain genes. In the case of the H chains, a wide range of variable region primers were used as described above. In addition, the F(ab)s obtained used variable regions genes from more than one VH and VK family. Most important, the recombinant F(ab)s cover the entire antigenic domain on TPO recognized by autoantibodies in the serum of patients.

The most remarkable finding from analysis of the presumptive germline genes used for TPO human autoantibodies is the relatively restricted numbers and combinations of H and L chain genes. Overall, among the 34 recombinant F(ab)s a total of only 7 different H and L chain combinations were found involving 7 H chains and 3 L chains. In addition, the same combination of H and L chains was found in three pairs of patients. These combinations involved different H chains (HV1L1, 1-1 and 3-1) with the same L chain (HUMIGKLVJ). The same pairing of H and L chains was observed in murine monoclonal antibodies (specific for influenza hemagglutinin) generated by both conventional hybridoma technology and the combinatorial recombinant F(ab) approach (Huse, W. D., Sastry, L., Iverson, S. A., Kang, A. S., Alting-Mees, M., Burton, D. R., Benkovic, S. J., and Lerner, R. A., "Generation of a large combinatorial library of the immunoglobulin repertoire in phage lambda," Science VOL. 246:1275–1281 (1989). Further, our F(ab)s had very high affinities for TPO ($^-10^{-10}$ M), comparable with those of serum TPO autoantibodies (Beever et al., (1989) supra). Studies of "natural" autoantibodies and autoantibodies to erythrocyte antigens have shown overrepresentation of VH4 family genes (Sanz et al., (1989) supra; Capra, J. D., Scand. J. Immunol (1992)). In contrast, 5/7 of our TPO-specific F(ab) combinations were derived from VH1 family germline genes. The other 2 F(ab) utilized putative VH3 and VH4 germline genes. Among the VH1-encoded TPO F(ab)s, the most abundant were related to the recently described HV1L1 germline gene, which is utilized in a rheumatoid factor (Carson, D., HV1L1. J. Exp. Med (1992)). Further, the 1-1 germline gene apparently used by two other TPO F(ab)s ranks very close to HV1L1 in the VH1 family. Because of consistent amino acid differences between the TPO F(abs) described here and HV1L1, it is likely that the former are not derived from HV1L1 but from another, as yet undescribed, germline gene.

There is evidence that the ability to produce TPO anti-antibodies is inherited as an autosomal dominant trait in women with incomplete penetrance in men (Phillips, D., McLachlan, S., Stephenson, A., Roberts, D., Moffitt, S., McDonald, D., Ad'Hiah, A., Stratton, A., Young, E., Clark, F., Beever, K., Bradbury, J., and Rees-Smith, B., "Autosomal dominant transmission of autoantibodies to thyroglobulin and thyroid peroxidase," *J. Clin. Endocrinol. Metab.* VOL. 70:742–74 (1990); Phillips, D., Prentice, L., Upadhyaya, M., Lunt, P., Chamberlain, S., Roberts, D. F., McLachlan, S., and Rees Smith, B., "Autosomal dominant inheritance of autoantibodies to thyroid peroxidase and thyroglobulin—Studies in families not selected for autoimmune thyroid disease," *J. Clin. Endocrinol. Metab.* VOL. 72:973–975 (1991)). The location and nature of the gene or gene cluster responsible for this inheritance are unknown. Polymorphisms at the VH locus are associated with autoantibody production (Olee, T., Yang, P-M., Siminovitch, K. A., Olsen, N. J., Hillson, J., Wu, J., Kozin, F., Carson, D. A., and Chen, P. P., "Molecular basis of an autoantibody-associated restriction fragment length polymorphism that confers susceptibility to autoimmune diseases," *J. Clin. Invest.* VOL. 88:193–203, (1991); Shin, E. K., Matsuda, F., Nagaoka, H., Fukita, Y., Imai, T., Yokoyama, K., Soeda, E., and Honjo, T., "Physical map of the 3' region of the human immunoglobulin heavy chain locus: clustering of autoantibody-related variable segments in one haplotype, *EMBO J.* VOL. 10:3641–3645 (1991)). Comparison of the Figures of the present example shows that one of the TPO F(ab)s described here is encoded by a VH gene involved in one of these polymorphisms. Knowledge of the genetic background of TPO-specific autoantibodies may provide insight into the basis for the inheritance of thyroid autoimmunity, and will provide a basis for the development of relevant diagnostic and therapeutic compositions and methods.

TPO, the primary autoantigen in autoimmune thyroiditis, is a glycoprotein expressed on the surface of the thyroid follicular cells (reviewed in McLachlan and Rapoport, 1992). TPO autoantibodies in patients' sera are heterogeneous and the majority recognize a conformational epitope(s), (Gardas, A., and Domek, H., "The effect of sulphydryl reagents on the human thyroid microsomal antigen," *J. Endocrinol. Invest.* VOL. 11:382–388 (1988); Nakajima, Y., Howells, R. D., Pegg, C., Davies Jones, E., and Rees Smith, B., "Structure activity analysis of microsomal antigen/thyroid peroxidase," *Molec. Cell. Endocrinol.* VOL. 53:15–23 (1987); Portolano et al. 1992). Despite studies using different approaches (reviewed in McLachlan and Rapoport (1992) supra), the number of epitopes recognized by TPO autoantibodies, or even the number of antigenic domains involved, has been unknown.

Using a comprehensive repertoire of recombinant human F(ab)s, the present invention defines two major epitopic areas, A and B, on TPO. Essentially all serum TPO autoantibodies interact with the A and B domains. TPO is a large (933 amino acid, 107 kD) (Magnusson, R., Chazenbalk, G., Gestautas, J., Seto, P., Filetti, S., and Rapoport, B., "Sequences of interest: molecular cloning of the complementary deoxyribonucleic acid for human thyroid peroxidase," *Mol. Endocrinol.* VOL. 1.856–861 (1987)) globular protein relative to the size of the F(ab) binding site (Davies, D. R., and Padlan, E., "Antibody-Antigen Complexes," *Annu. Rev. Biochem.* VOL. 59:439–47 (1990)). For this reason and because a combination of only two different Fabs can compete for binding by all TPO autoantibodies, the autoimmunogenic region comprises a single, relatively small area (domains A+B). As described above, it is possible that serum TPO autoantibodies to other regions of TPO, including linear epitopes, exist, but these will comprise a very small proportion of the repertoire.

The present invention now permits analysis of the relationship between H and L chain genes and the antigenic domains on TPO recognized by TPO autoantibodies. Such an analysis has not previously been possible in an autoimmune disease. The clearest association is between the L chain gene HUMIGKLVJ and the A domain on TPO. In contrast, the B domain is most closely associated with the L chains A' and A3. The H chains are more diverse and may alter the fine specificity of the F(ab) binding site by interacting with antigenic areas adjacent to the L chain binding site. In some instances, exemplified by TR1.3 (VH 8-1b/VK HUMIGKLVJ), the H chain shifts the F(ab) binding from the A domain to cover both A and B domains.

Of interest is the observation that F(ab)s of both subclass IgG1 and IgG4 can interact with the A domain on TPO. Among these are F(ab)s encoded for by two closely related VHI genes, namely 1-1 in the case of IgG1 F(ab)s and HV1L1 in the case of IgG4 F(ab)s. This apparent difference in germline gene origin suggests that the IgG4 F(ab)s are not derived from the IgG1 F(ab)s by subclass switching. In rheumatoid factors, the same germline gene has clearly been shown to code for a low affinity IgM and subsequently for an affinity-matured IgG molecule (Randen, I., Brown, D., Thompson, K. M., Hughes-Jones, N., Pascual, V., Victor, K., Capra, J. D., Forre, O., and Natvig, J. B., "Clonally related IgM rheumatoid factors undergo affinity maturation in the rheumatoid synovial tissue," *J. Immun.* VOL. 148:3296–3301 (1992)). In constrast, observations of cross-reactive idiotypes in human antibodies to *H. influenzae* b polysaccharide indicate independent B cell lineages in IgG1 and IgG2 antibodies (Lucas, A. H., and Granoff, D. M., "A major crossreactive idiotype associated with human antibodies to the Haemophilus influenza b polysaccharide. Expression in relation to age and immunoglobulin G subclass," *J. Clin. Invest.* VOL. 85:1158–1166 (1990)). However, as mentioned above, it is possible that HV1L1 is not the germline gene from which the IgG4 TPO-specific F(ab)s were derived. Therefore, we cannot exclude the possibility that both IgG1 and IgG4 TPO-specific F(ab)s are derived by switching from the same, as yet undescribed, VH1 germline gene.

Studies in mice have provided evidence for (Shlomchik, M. J., Marshak-Rothstein, A., Wolfwicz, C. B., Rothstein, T. L., and Weigert, M. G., "The role of clonal selection and somatic mutation in autoimmunity," *Nature* VOL. 328:805–811 (1987); O'Keefe, T. L., Bandyopadhyay, S., Datta, S. K., and Imanishi-Kari, T., "V region sequences of an idiotypically connected family of pathogenic anti-DNA autoantibodies," *J. Immun.* VOL. 144:4275–4283 (1990); Eilat, D., and Fischel, R., "Recurrent utilization of genetic elements in V regions of antinucleic acid antibodies from autoimmune mice," *J. Immun.* VOL. 147:361–368 (1991)) and against (Panosian-Sahakian, N., Klotz, J. L., Ebling, F., Kronenberg, M., and Hahn, B., "Diversity of Ig V gene segments found in anti-DNA autoantibodies from a single (NZB×NZW)F1 mouse," *J. Immun.* VOL. 142:4500–4506

(1989)) restricted H and L chain usage in rheumatoid factors and DNA autoantibodies. Similarly, a diverse array of immunoglobulin genes occurs in IgM-class rheumatoid factors (Pascual, V., Victor, K., Randen, I., Thompson, K., Natvig, J. B., and Capra, J. D. "IgM rheumatoid factors in patients with rheumatoid arthritis derive from a diverse array of germline immunoglobulin genes and display little evidence of somatic variation," *J. Rheum.*, (1992)). A possible explanation for these divergent observations is that the autoantibodies are interacting with a wide range of epitopes. For example, thyroglobulin autoantibodies, induced by immunization in mice, interact with a wide range of epitopes and are derived from a large number of V region gene segments (Gleason, S. L., Gearhart, P., Rose, N. R., and Kuppers, R. C., "Autoantibodies to thyroglobulin are encoded by V-gene segments and recognize restricted epitopes," *J. Immun.* VOL. 145:1768–1775 (1990)). The limited antigenic region on TPO recognized by disease-associated autoantibodies simplifies this issue. Under these conditions, there is, indeed, restriction in H and L chain usage in human, organ-specific autoimmune disease.

TABLE VI

Summary of TPO-specific human F(ab)s obtained from 4 Graves' patients. Combinatorial libraries were constructed from mRNA prepared from intrathyroidal B cells as described.

| Library (Frequency) | Subclass | Clone | H Chain Germline[a] | VH | JH | L Chain Germline[a] | VK | JK |
|---|---|---|---|---|---|---|---|---|
| WR I (11/90,000) | 1 | 1.7; 1.9 | 3-1 | 1 | 4 | KLVJ | 1 | 1 |
| | 4 | 4.2–5; 4.8 4.10–12 | HV1L1 | 1 | 4 | KLVJ | 1 | 2 |
| | 4 | 4.6 | 4.22 | 4 | 5 | KLVJ | 1 | 2 |
| WR IV (15/30,000) | 4 | 4.21; 4.22; 4.25–35 | HV1L1 | 1 | 4 | KLVJ | 1 | 2 |
| TR I (7/90,000) | 1 | 1.3; 1.5 | 8-1B | 3 | 4 | KLVJ | 1 | 2 |
| | 1 | 1.6; 1.8 | HV1263 | 1 | 3 | A3 | 2 | 2 |
| | 1 | 1.9; 1.13 | V35 | 1 | 4 | A' | 1 | 4 |
| | 1 | 1.10 | 3-1 | 1 | 4 | KLVJ | 1 | 1 |
| JA I (1/200,000) | 1 | 1.9 | 1-1 | 1 | 6 | KLVJ | 1 | 4 |
| JA IV (0/200,000) | — | — | | | | | | |
| SP I[b] (3/180,000) | 1 | 1.2 | 1-1 | 1 | 6 | KLVJ | 1 | 2 |
| | | 1.4; 1.5 | 1-1 | 1 | 6 | KLVJ | 1 | 1 |
| | 4 | 4.6 | HV1L1 | 1 | 4 | KLVJ | 1 | 2 |

[a]Presumptive germline genes.
[b]Previously published. Clone SP4.6 was obtained by recombining the SP1.2 L chain with the parent SP I H chain library as described herein.

TABLE VII

Affinities for human TPC of expressed F(ab) fragments.

| H Chain | L Chain | Clone | Affinity (Kd) |
|---|---|---|---|
| HV1L1 | KLVJ | WR4.5 | 3.0, 3.2 × 10$^{-10}$ M |
| | | SP4.6[b] | 1.0 ± 0.2 × 10$^{-10}$ M |
| 3-1 | KLVJ | WR1.7 | 1.2, 2.9 × 10$^{-10}$ M |
| | | TR1.10 | 1.7, 1.4 × 10$^{-10}$ M |
| 8-1B | KLVJ | TR1.3 | 5.1 ± 0.1 × 10$^{-10}$ M |
| 1-1 | KLVJ | SP1.2[a] | 8.0 ± 1.0 × 10$^{-11}$ M |
| | | SP1.4[a] | 2.0; 2.0 × 10$^{-10}$ M |
| | | SP1.5[a] | 8.0 ± 1.0 × 10$^{11}$ M |
| HV1263 | A3 | TR1.8 | 2.7 ± 0.1 × 10$^{-10}$ M |
| V35 | A' | TR1.9 | 1.5 ± 0.2 × 10$^{-10}$ M |

Values from duplicate or triplicate experiments were calculated by Scatchard analysis. [a]; [b]previously described herein.

TABLE VIII:

Domains on TPO recognized by F(ab)s as determined by competition between pairs of F(ab)s for antigen binding.

| | TPO Domains | | | |
|---|---|---|---|---|
| Clone | A | B | H Chain | L Chain |
| SP1.5 | ++++ | – | 1-1 | KLVJ |
| WR4.5 | ++++ | – | HV1L1 | KLVJ |
| WR1.7 | ++++ | ++ | 3-1 | KLVJ |
| TR1.3 | ++++ | ++++ | 8-1B | KLVJ |
| TR1.8 | + | ++++ | HV1263 | A3 |
| TR1.9 | – | ++++ | V35 | A' |

"++++" Represents complete and "–" represents no overlap with the indicated domain. "+" or "++" indicate partial overlap.

What is claimed is:

1. A recombinant DNA sequence encoding a human thyroid peroxidase which is secreted from a cell, wherein the DNA has the sequence of SEQ ID NO: 2 with a stop codon at nucleotides.

2. A recombinant DNA sequence consisting of nucleotides 1–2628 of SEQ ID NO: 2.

3. A recombinant DNA sequence consisting of nucleotides 85–2628 of SEQ ID NO: 2.

4. A recombinant DNA sequence encoding a human thyroid peroxidase that consists of amino acids 1 to 848 of the amino acid sequence shown in SEQ ID NO: 3.

* * * * *

UNITED STATES PATENT AND TRADEMARK OFFICE
CERTIFICATE OF CORRECTION

PATENT NO. : 7,196,181 B1  Page 1 of 1
APPLICATION NO. : 08/482402
DATED : March 27, 2007
INVENTOR(S) : Basil Rapoport It is certified that error appears in the above-identified patent and that said Letters Patent is hereby corrected as shown below:

Column 91, line 24, insert --2629-2631-- after "nucleotides"

Signed and Sealed this

Seventeenth Day of June, 2008

JON W. DUDAS
*Director of the United States Patent and Trademark Office*

SEQUENCE LISTING

<160> NUMBER OF SEQ ID NOS: 12

<210> SEQ ID NO 1
<211> LENGTH: 104
<212> TYPE: DNA
<213> ORGANISM: Homo sapiens

<400> SEQUENCE: 1

```
aggctccctc gggtgacttg gatctccatg tcgctggctg ctctgctgat cgaggctccc    60
tcgggtgact tgaattccca gtagctggc tgctctgcta tcg                       104
```

<210> SEQ ID NO 2
<211> LENGTH: 3072
<212> TYPE: DNA
<213> ORGANISM: Homo sapiens
<220> FEATURE:
<221> NAME/KEY: CDS
<222> LOCATION: (85)..(2883)
<223> OTHER INFORMATION:

<400> SEQUENCE: 2

```
gaggcaattg aggcgcccat ttcagaagag ttacagccgt gaaaattact cagcagtgca    60
gttggctgag aagaggaaaa aaga atg aga gcg ctg gct gtg ctg tct gtc      111
                          Met Arg Ala Leu Ala Val Leu Ser Val
                          1               5 acg ctg gtt atg gcc tgc aca gaa gcc ttc ttc ccc ttc atc tcg aga    159
Thr Leu Val Met Ala Cys Thr Glu Ala Phe Phe Pro Phe Ile Ser Arg
 10              15                  20                  25 ggg aaa gaa ctc ctt tgg gga aag cct gag gag tct cgt gtc tct agc    207
Gly Lys Glu Leu Leu Trp Gly Lys Pro Glu Glu Ser Arg Val Ser Ser
             30                  35                  40 gtc ttg gag gaa agc aag cgc ctg gtg gac acc gcc atg tac gcc acg    255
Val Leu Glu Glu Ser Lys Arg Leu Val Asp Thr Ala Met Tyr Ala Thr
         45                  50                  55 atg cag aga aac ctc aag aaa aga gga atc ctt tct gga gct cag ctt    303
Met Gln Arg Asn Leu Lys Lys Arg Gly Ile Leu Ser Gly Ala Gln Leu
     60                  65                  70 ctg tct ttt tcc aaa ctt cct gag cca aca agc gga gtg att gcc cga    351
Leu Ser Phe Ser Lys Leu Pro Glu Pro Thr Ser Gly Val Ile Ala Arg
 75                  80                  85 gca gca gag ata atg gaa aca tca ata caa gcg atg aaa aga aaa gtc    399
Ala Ala Glu Ile Met Glu Thr Ser Ile Gln Ala Met Lys Arg Lys Val
 90                  95                 100                 105 aac ctg aaa act caa caa tca cag cat cca acg gat gct tta tca gaa    447
Asn Leu Lys Thr Gln Gln Ser Gln His Pro Thr Asp Ala Leu Ser Glu
                110                 115                 120 gat ctg ctg agc atc att gca aac atg tct gga tgt ctc cct tac atg    495
Asp Leu Leu Ser Ile Ile Ala Asn Met Ser Gly Cys Leu Pro Tyr Met
            125                 130                 135 ctg ccc cca aaa tgc cca aac act tgc ctg gcg aac aaa tac agg ccc    543
Leu Pro Pro Lys Cys Pro Asn Thr Cys Leu Ala Asn Lys Tyr Arg Pro
        140                 145                 150 atc aca gga gct tgc aac aac aga gac cac ccc aga tgg ggc gcc tcc    591
Ile Thr Gly Ala Cys Asn Asn Arg Asp His Pro Arg Trp Gly Ala Ser
    155                 160                 165 aac acg gcc ctg gca cga tgg ctc cct cca gtc tat gag gac ggc ttc    639
Asn Thr Ala Leu Ala Arg Trp Leu Pro Pro Val Tyr Glu Asp Gly Phe
170                 175                 180                 185 agt cag ccc cga ggc tgg aac ccc ggc ttc ttg tac aac ggg ttc cca    687
```

```
                                          -continued
Ser Gln Pro Arg Gly Trp Asn Pro Gly Phe Leu Tyr Asn Gly Phe Pro
            190                 195                 200 ctg ccc ccg gtc cgg gag gtg aca aga cat gtc att caa gtt tca aat      735
Leu Pro Pro Val Arg Glu Val Thr Arg His Val Ile Gln Val Ser Asn
            205                 210                 215 gag gtt gtc aca gat gat gac cgc tat tct gac ctc ctg atg gca tgg      783
Glu Val Val Thr Asp Asp Asp Arg Tyr Ser Asp Leu Leu Met Ala Trp
            220                 225                 230 gga caa tac atc gac cac gac atc gcg ttc aca cca cag agc acc agc      831
Gly Gln Tyr Ile Asp His Asp Ile Ala Phe Thr Pro Gln Ser Thr Ser
        235                 240                 245 aaa gct gcc ttc ggg gga ggg tct gac tgc cag atg act tgt gag aac      879
Lys Ala Ala Phe Gly Gly Gly Ser Asp Cys Gln Met Thr Cys Glu Asn
250             255                 260                 265 caa aac cca tgt ttt ccc ata caa ctc ccg gag gag gcc cgg ccg gcc      927
Gln Asn Pro Cys Phe Pro Ile Gln Leu Pro Glu Glu Ala Arg Pro Ala
                270                 275                 280 gcg ggc acc gcc tgt ctg ccc ttc tac cgc tct tcg gcc gcc tgc ggc      975
Ala Gly Thr Ala Cys Leu Pro Phe Tyr Arg Ser Ser Ala Ala Cys Gly
                285                 290                 295 acc ggg gac caa ggc gcg ctc ttt ggg aac ctg tcc acg gcc aac ccg     1023
Thr Gly Asp Gln Gly Ala Leu Phe Gly Asn Leu Ser Thr Ala Asn Pro
            300                 305                 310 agg cag cag atg aac ggg ttg acc tcg ttc ctg gac gcg tcc acc gtg     1071
Arg Gln Gln Met Asn Gly Leu Thr Ser Phe Leu Asp Ala Ser Thr Val
        315                 320                 325 tat ggc agc tcc ccg gcc cta gag agg cag ctg cgg aac tgg acc agt     1119
Tyr Gly Ser Ser Pro Ala Leu Glu Arg Gln Leu Arg Asn Trp Thr Ser
330             335                 340                 345 gcc gaa ggg ctg ctc cgc gtc cac ggc cgc ctc cgg gac tcc ggc cgc     1167
Ala Glu Gly Leu Leu Arg Val His Gly Arg Leu Arg Asp Ser Gly Arg
                350                 355                 360 gcc tac ctg ccc ttc gtg ccg cca cgc gcg cct gcg gcc tgt gcg ccc     1215
Ala Tyr Leu Pro Phe Val Pro Pro Arg Ala Pro Ala Ala Cys Ala Pro
                365                 370                 375 gag ccc ggc aac ccc gga gag acc cgc ggg ccc tgc ttc ctg gcc gga     1263
Glu Pro Gly Asn Pro Gly Glu Thr Arg Gly Pro Cys Phe Leu Ala Gly
            380                 385                 390 gac ggc cgc gcc agc gag gtc ccc tcc ctg acg gca ctg cac acg ctg     1311
Asp Gly Arg Ala Ser Glu Val Pro Ser Leu Thr Ala Leu His Thr Leu
        395                 400                 405 tgg ctg cgc gag cac aac cgc ctg gcc gcg gcg ctc aag gcc ctc aat     1359
Trp Leu Arg Glu His Asn Arg Leu Ala Ala Ala Leu Lys Ala Leu Asn
410             415                 420                 425 gcg cac tgg agc gcg gac gcc gtg tac cag gag gcg cgc aag gtc gtg     1407
Ala His Trp Ser Ala Asp Ala Val Tyr Gln Glu Ala Arg Lys Val Val
                430                 435                 440 ggc gct ctg cac cag atc atc acc ctg agg gat tac atc ccc agg atc     1455
Gly Ala Leu His Gln Ile Ile Thr Leu Arg Asp Tyr Ile Pro Arg Ile
                445                 450                 455 ctg gga ccc gag gcc ttc cag cag tac gtg ggt ccc tat gaa ggc tat     1503
Leu Gly Pro Glu Ala Phe Gln Gln Tyr Val Gly Pro Tyr Glu Gly Tyr
            460                 465                 470 gac tcc acc gcc aac ccc act gtg tcc aac gtg ttc tcc aca gcc gcc     1551
Asp Ser Thr Ala Asn Pro Thr Val Ser Asn Val Phe Ser Thr Ala Ala
        475                 480                 485 ttc cgc ttc ggc cat gcc acg atc cac ccg ctg gtg agg agg ctg gac     1599
Phe Arg Phe Gly His Ala Thr Ile His Pro Leu Val Arg Arg Leu Asp
490             495                 500                 505
```

-continued

| | |
|---|---|
| gcc agc ttc cag gag cac ccc gac ctg ccc ggg ctg tgg ctg cac cag<br>Ala Ser Phe Gln Glu His Pro Asp Leu Pro Gly Leu Trp Leu His Gln<br>      510                515                520 | 1647 |
| gct ttc ttc agc cca tgg aca tta ctc cgt gga ggt ggt ttg gac cca<br>Ala Phe Phe Ser Pro Trp Thr Leu Leu Arg Gly Gly Gly Leu Asp Pro<br>525                530                535 | 1695 |
| cta ata cga ggc ctt ctt gca aga cca gcc aaa ctg cag gtg cag gat<br>Leu Ile Arg Gly Leu Leu Ala Arg Pro Ala Lys Leu Gln Val Gln Asp<br>      540                545                550 | 1743 |
| cag ctg atg aac gag gag ctg acg gaa agg ctc ttt gtg ctg tcc aat<br>Gln Leu Met Asn Glu Glu Leu Thr Glu Arg Leu Phe Val Leu Ser Asn<br>555                560                565 | 1791 |
| tcc agc acc ttg gat ctg gcg tcc atc aac ctg cag agg ggc cgg gac<br>Ser Ser Thr Leu Asp Leu Ala Ser Ile Asn Leu Gln Arg Gly Arg Asp<br>570                575                580                585 | 1839 |
| cac ggg ctg cca ggt tac aat gag tgg agg gag ttc tgc ggc ctg cct<br>His Gly Leu Pro Gly Tyr Asn Glu Trp Arg Glu Phe Cys Gly Leu Pro<br>      590                595                600 | 1887 |
| cgc ctg gag acc ccc gct gac ctg agc aca gcc atc gcc agc agg agc<br>Arg Leu Glu Thr Pro Ala Asp Leu Ser Thr Ala Ile Ala Ser Arg Ser<br>605                610                615 | 1935 |
| gtg gcc gac aag atc ctg gac ttg tac aag cat cct gac aac atc gat<br>Val Ala Asp Lys Ile Leu Asp Leu Tyr Lys His Pro Asp Asn Ile Asp<br>      620                625                630 | 1983 |
| gtc tgg ctg gga ggc tta gct gaa aac ttc ctc ccc agg gct cgg aca<br>Val Trp Leu Gly Gly Leu Ala Glu Asn Phe Leu Pro Arg Ala Arg Thr<br>635                640                645 | 2031 |
| ggg ccc ctg ttt gcc tgt ctc att ggg aag cag atg aag gct ctg cgg<br>Gly Pro Leu Phe Ala Cys Leu Ile Gly Lys Gln Met Lys Ala Leu Arg<br>650                655                660                665 | 2079 |
| gac ggt gac tgg ttt tgg tgg gag aac agc cac gtc ttc acg gat gca<br>Asp Gly Asp Trp Phe Trp Trp Glu Asn Ser His Val Phe Thr Asp Ala<br>      670                675                680 | 2127 |
| cag agg cgt gag ctg gag aag cac tcc ctg tct cgg gtc atc tgt gac<br>Gln Arg Arg Glu Leu Glu Lys His Ser Leu Ser Arg Val Ile Cys Asp<br>685                690                695 | 2175 |
| aac act ggc ctc acc agg gtg ccc atg gat gcc ttc caa gtc ggc aaa<br>Asn Thr Gly Leu Thr Arg Val Pro Met Asp Ala Phe Gln Val Gly Lys<br>      700                705                710 | 2223 |
| ttc ccc gaa gac ttt gag tct tgt gac agc atc act ggc atg aac ctg<br>Phe Pro Glu Asp Phe Glu Ser Cys Asp Ser Ile Thr Gly Met Asn Leu<br>715                720                725 | 2271 |
| gag gcc tgg agg gaa acc ttt cct caa gac gac aag tgt ggc ttc cca<br>Glu Ala Trp Arg Glu Thr Phe Pro Gln Asp Asp Lys Cys Gly Phe Pro<br>730                735                740                745 | 2319 |
| gag agc gtg gag aat ggg gac ttt gtg cac tgt gag gag tct ggg agg<br>Glu Ser Val Glu Asn Gly Asp Phe Val His Cys Glu Glu Ser Gly Arg<br>      750                755                760 | 2367 |
| cgc gtg ctg gtg tat tcc tgc cgg cac ggg tat gag ctc caa ggc cgg<br>Arg Val Leu Val Tyr Ser Cys Arg His Gly Tyr Glu Leu Gln Gly Arg<br>765                770                775 | 2415 |
| gag cag ctc act tgc acc cag gaa gga tgg gat ttc cag cct ccc ctc<br>Glu Gln Leu Thr Cys Thr Gln Glu Gly Trp Asp Phe Gln Pro Pro Leu<br>      780                785                790 | 2463 |
| tgc aaa gat gtg aac gag tgt gca gac ggt gcc cac ccc ccc tgc cac<br>Cys Lys Asp Val Asn Glu Cys Ala Asp Gly Ala His Pro Pro Cys His<br>795                800                805 | 2511 |
| gcc tct gcg agg tgc aga aac acc aaa ggc ggc ttc cag tgt ctc tgc<br>Ala Ser Ala Arg Cys Arg Asn Thr Lys Gly Gly Phe Gln Cys Leu Cys<br>810                815                820                825 | 2559 |

-continued

```
gcg gac ccc tac gag tta gga gac gat ggg aga acc tgc gta gac tcc    2607
Ala Asp Pro Tyr Glu Leu Gly Asp Asp Gly Arg Thr Cys Val Asp Ser
            830                 835                 840 ggg agg ctc cct cgg gtg act tgg atc tcc atg tcg ctg gct gct ctg    2655
Gly Arg Leu Pro Arg Val Thr Trp Ile Ser Met Ser Leu Ala Ala Leu
            845                 850                 855 ctg atc gga ggc ttc gca ggt ctc acc tcg acg gtg att tgc agg tgg    2703
Leu Ile Gly Gly Phe Ala Gly Leu Thr Ser Thr Val Ile Cys Arg Trp
            860                 865                 870 aca cgc act ggc act aaa tcc aca ctg ccc atc tcg gag aca ggc gga    2751
Thr Arg Thr Gly Thr Lys Ser Thr Leu Pro Ile Ser Glu Thr Gly Gly
    875                 880                 885 gga act ccc gag ctg aga tgc gga aag cac cag gcc gta ggg acc tca    2799
Gly Thr Pro Glu Leu Arg Cys Gly Lys His Gln Ala Val Gly Thr Ser
890                 895                 900                 905 ccg cag cgg gcc gca gct cag gac tcg gag cag gag agt gct ggg atg    2847
Pro Gln Arg Ala Ala Ala Gln Asp Ser Glu Gln Glu Ser Ala Gly Met
                910                 915                 920 gaa ggc cgg gat act cac agg ctg ccg aga gcc ctc tgagggcaaa         2893
Glu Gly Arg Asp Thr His Arg Leu Pro Arg Ala Leu
            925                 930 gtggcaggac actgcagaac agcttcatgt tcccaaaatc accgtacgac tcttttccaa  2953
acacaggcaa atcggaaatc agcaggacga ctgttttccc aacacgggta aatctagtac  3013
catgtcgtag ttactctcag gcatggatga ataaatgtta tagctgcaaa aaaaaaaaa   3072

<210> SEQ ID NO 3
<211> LENGTH: 933
<212> TYPE: PRT
<213> ORGANISM: Homo sapiens

<400> SEQUENCE: 3

Met Arg Ala Leu Ala Val Leu Ser Val Thr Leu Val Met Ala Cys Thr
1               5                   10                  15

Glu Ala Phe Phe Pro Phe Ile Ser Arg Gly Lys Glu Leu Leu Trp Gly
            20                  25                  30

Lys Pro Glu Glu Ser Arg Val Ser Val Leu Glu Glu Ser Lys Arg
        35                  40                  45

Leu Val Asp Thr Ala Met Tyr Ala Thr Met Gln Arg Asn Leu Lys Lys
    50                  55                  60

Arg Gly Ile Leu Ser Gly Ala Gln Leu Leu Ser Phe Ser Lys Leu Pro
65                  70                  75                  80

Glu Pro Thr Ser Gly Val Ile Ala Arg Ala Ala Glu Ile Met Glu Thr
                85                  90                  95

Ser Ile Gln Ala Met Lys Arg Lys Val Asn Leu Lys Thr Gln Gln Ser
            100                 105                 110

Gln His Pro Thr Asp Ala Leu Ser Glu Asp Leu Leu Ser Ile Ile Ala
        115                 120                 125

Asn Met Ser Gly Cys Leu Pro Tyr Met Leu Pro Pro Lys Cys Pro Asn
    130                 135                 140

Thr Cys Leu Ala Asn Lys Tyr Arg Pro Ile Thr Gly Ala Cys Asn Asn
145                 150                 155                 160

Arg Asp His Pro Arg Trp Gly Ala Ser Asn Thr Ala Leu Ala Arg Trp
                165                 170                 175

Leu Pro Pro Val Tyr Glu Asp Gly Phe Ser Gln Pro Arg Gly Trp Asn
            180                 185                 190
```

```
Pro Gly Phe Leu Tyr Asn Gly Phe Pro Leu Pro Pro Val Arg Glu Val
        195                 200                 205

Thr Arg His Val Ile Gln Val Ser Asn Glu Val Val Thr Asp Asp Asp
        210                 215                 220

Arg Tyr Ser Asp Leu Leu Met Ala Trp Gly Gln Tyr Ile Asp His Asp
225                 230                 235                 240

Ile Ala Phe Thr Pro Gln Ser Thr Ser Lys Ala Ala Phe Gly Gly Gly
                245                 250                 255

Ser Asp Cys Gln Met Thr Cys Glu Asn Gln Asn Pro Cys Phe Pro Ile
            260                 265                 270

Gln Leu Pro Glu Glu Ala Arg Pro Ala Ala Gly Thr Ala Cys Leu Pro
        275                 280                 285

Phe Tyr Arg Ser Ser Ala Ala Cys Gly Thr Gly Asp Gln Gly Ala Leu
        290                 295                 300

Phe Gly Asn Leu Ser Thr Ala Asn Pro Arg Gln Gln Met Asn Gly Leu
305                 310                 315                 320

Thr Ser Phe Leu Asp Ala Ser Thr Val Tyr Gly Ser Pro Ala Leu
                325                 330                 335

Glu Arg Gln Leu Arg Asn Trp Thr Ser Ala Glu Gly Leu Leu Arg Val
            340                 345                 350

His Gly Arg Leu Arg Asp Ser Gly Arg Ala Tyr Leu Pro Phe Val Pro
        355                 360                 365

Pro Arg Ala Pro Ala Ala Cys Ala Pro Glu Pro Gly Asn Pro Gly Glu
        370                 375                 380

Thr Arg Gly Pro Cys Phe Leu Ala Gly Asp Gly Arg Ala Ser Glu Val
385                 390                 395                 400

Pro Ser Leu Thr Ala Leu His Thr Leu Trp Leu Arg Glu His Asn Arg
                405                 410                 415

Leu Ala Ala Ala Leu Lys Ala Leu Asn Ala His Trp Ser Ala Asp Ala
            420                 425                 430

Val Tyr Gln Glu Ala Arg Lys Val Val Gly Ala Leu His Gln Ile Ile
        435                 440                 445

Thr Leu Arg Asp Tyr Ile Pro Arg Ile Leu Gly Pro Glu Ala Phe Gln
450                 455                 460

Gln Tyr Val Gly Pro Tyr Glu Gly Tyr Asp Ser Thr Ala Asn Pro Thr
465                 470                 475                 480

Val Ser Asn Val Phe Ser Thr Ala Ala Phe Arg Phe Gly His Ala Thr
                485                 490                 495

Ile His Pro Leu Val Arg Arg Leu Asp Ala Ser Phe Gln Glu His Pro
            500                 505                 510

Asp Leu Pro Gly Leu Trp Leu His Gln Ala Phe Phe Ser Pro Trp Thr
        515                 520                 525

Leu Leu Arg Gly Gly Gly Leu Asp Pro Leu Ile Arg Gly Leu Leu Ala
        530                 535                 540

Arg Pro Ala Lys Leu Gln Val Gln Asp Gln Leu Met Asn Glu Glu Leu
545                 550                 555                 560

Thr Glu Arg Leu Phe Val Leu Ser Asn Ser Ser Thr Leu Asp Leu Ala
                565                 570                 575

Ser Ile Asn Leu Gln Arg Gly Arg Asp His Gly Leu Pro Gly Tyr Asn
            580                 585                 590

Glu Trp Arg Glu Phe Cys Gly Leu Pro Arg Leu Glu Thr Pro Ala Asp
        595                 600                 605

Leu Ser Thr Ala Ile Ala Ser Arg Ser Val Ala Asp Lys Ile Leu Asp
```

```
                    610                 615                 620
Leu Tyr Lys His Pro Asp Asn Ile Asp Val Trp Leu Gly Gly Leu Ala
625                 630                 635                 640

Glu Asn Phe Leu Pro Arg Ala Arg Thr Gly Pro Leu Phe Ala Cys Leu
                645                 650                 655

Ile Gly Lys Gln Met Lys Ala Leu Arg Asp Gly Asp Trp Phe Trp Trp
            660                 665                 670

Glu Asn Ser His Val Phe Thr Asp Ala Gln Arg Arg Glu Leu Glu Lys
            675                 680                 685

His Ser Leu Ser Arg Val Ile Cys Asp Asn Thr Gly Leu Thr Arg Val
            690                 695                 700

Pro Met Asp Ala Phe Gln Val Gly Lys Phe Pro Glu Asp Phe Glu Ser
705                 710                 715                 720

Cys Asp Ser Ile Thr Gly Met Asn Leu Glu Ala Trp Arg Glu Thr Phe
                725                 730                 735

Pro Gln Asp Asp Lys Cys Gly Phe Pro Glu Ser Val Glu Asn Gly Asp
                740                 745                 750

Phe Val His Cys Glu Glu Ser Gly Arg Arg Val Leu Val Tyr Ser Cys
            755                 760                 765

Arg His Gly Tyr Glu Leu Gln Gly Arg Glu Gln Leu Thr Cys Thr Gln
            770                 775                 780

Glu Gly Trp Asp Phe Gln Pro Pro Leu Cys Lys Asp Val Asn Glu Cys
785                 790                 795                 800

Ala Asp Gly Ala His Pro Pro Cys His Ala Ser Ala Arg Cys Arg Asn
                805                 810                 815

Thr Lys Gly Gly Phe Gln Cys Leu Cys Ala Asp Pro Tyr Glu Leu Gly
                820                 825                 830

Asp Asp Gly Arg Thr Cys Val Asp Ser Gly Arg Leu Pro Arg Val Thr
            835                 840                 845

Trp Ile Ser Met Ser Leu Ala Ala Leu Leu Ile Gly Gly Phe Ala Gly
            850                 855                 860

Leu Thr Ser Thr Val Ile Cys Arg Trp Thr Arg Thr Gly Thr Lys Ser
865                 870                 875                 880

Thr Leu Pro Ile Ser Glu Thr Gly Gly Thr Pro Glu Leu Arg Cys
                885                 890                 895

Gly Lys His Gln Ala Val Gly Thr Ser Pro Gln Arg Ala Ala Ala Gln
            900                 905                 910

Asp Ser Glu Gln Glu Ser Ala Gly Met Glu Gly Arg Asp Thr His Arg
            915                 920                 925

Leu Pro Arg Ala Leu
    930

<210> SEQ ID NO 4
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION:

<400> SEQUENCE: 4 aac cca tgt ttt ccc ata caa ctc ccg gag gag gcc cgg ccg gcc      45
Asn Pro Cys Phe Pro Ile Gln Leu Pro Glu Glu Ala Arg Pro Ala
1               5                   10                  15
```

```
<210> SEQ ID NO 5
<211> LENGTH: 15
<212> TYPE: PRT
<213> ORGANISM: Homo sapiens

<400> SEQUENCE: 5

Asn Pro Cys Phe Pro Ile Gln Leu Pro Glu Glu Ala Arg Pro Ala
1               5                   10                  15

<210> SEQ ID NO 6
<211> LENGTH: 29
<212> TYPE: DNA
<213> ORGANISM: Homo sapiens
<220> FEATURE:
<221> NAME/KEY: CDS
<222> LOCATION: (3)..(29)
<223> OTHER INFORMATION:

<400> SEQUENCE: 6 gc aaa ttc ccc gaa gac ttt gag tct tgt                           29
   Lys Phe Pro Glu Asp Phe Glu Ser Cys
    1               5

<210> SEQ ID NO 7
<211> LENGTH: 9
<212> TYPE: PRT
<213> ORGANISM: Homo sapiens

<400> SEQUENCE: 7

Lys Phe Pro Glu Asp Phe Glu Ser Cys
1               5

<210> SEQ ID NO 8
<211> LENGTH: 52
<212> TYPE: DNA
<213> ORGANISM: Artificial Sequence
<220> FEATURE:
<223> OTHER INFORMATION: A mutagenic primer to a human thyrodine
      peroxidase cDNA designed to generate two stop codons at
      nucleotides 2629-2631 and 2641-2643.

<400> SEQUENCE: 8
aggctccctc gggtgacttg aattcccatg tagctggctg ctctgctgat cg          52

<210> SEQ ID NO 9
<211> LENGTH: 14
<212> TYPE: DNA
<213> ORGANISM: Artificial Sequence
<220> FEATURE:
<223> OTHER INFORMATION: An EcoRI linker.

<400> SEQUENCE: 9
gaattcggca cgag                                                   14

<210> SEQ ID NO 10
<211> LENGTH: 22
<212> TYPE: DNA
<213> ORGANISM: Artificial Sequence
<220> FEATURE:
<223> OTHER INFORMATION: Human thyrodine peroxidase primer.

<400> SEQUENCE: 10
ggttacaatg agtggaggga gt                                          22

<210> SEQ ID NO 11
<211> LENGTH: 22
<212> TYPE: DNA
```

-continued

```
<213> ORGANISM: Artificial Sequence
<220> FEATURE:
<223> OTHER INFORMATION: Human thyrodine peroxidase primer.

<400> SEQUENCE: 11
gtggctgttc tcccaccaaa ac                                               22

<210> SEQ ID NO 12
<211> LENGTH: 47
<212> TYPE: DNA
<213> ORGANISM: Homo sapiens

<400> SEQUENCE: 12
aaaacccatg ttttcccata caactcccgg aggaggcccg gccggcc                    47
```